US008148093B2

(12) United States Patent
Simon et al.

(10) Patent No.: US 8,148,093 B2
(45) Date of Patent: Apr. 3, 2012

(54) PRO108 ANTIBODY COMPOSITIONS AND METHODS OF USE AND USE OF PRO108 TO ASSESS CANCER RISK

(75) Inventors: Iris Simon, San Francisco, CA (US); Laura Corral, San Francisco, CA (US); Charis Lawrenson, San Jose, CA (US); Nam Kim, Santa Clara, CA (US); Glenn Pilkington, Sorrento (AU); Robert L. Wolfert, Palo Alto, CA (US)

(73) Assignee: diaDexus, Inc., South San Francisco ( * ) Notice: Subject to any disclaimer, the term of this patent is extended or adjusted under 35 U.S.C. 154(b) by 989 days.

(21) Appl. No.: 11/866,475

(22) Filed: Oct. 3, 2007

(65) Prior Publication Data

US 2009/0232732 A1    Sep. 17, 2009

Related U.S. Application Data

(62) Division of application No. 10/919,215, filed on Aug. 16, 2004, now Pat. No. 7,294,704.

(60) Provisional application No. 60/556,465, filed on Mar. 25, 2004, provisional application No. 60/495,759, filed on Aug. 15, 2003.

(51) Int. Cl.
*G01N 33/53* (2006.01)
*G01N 33/574* (2006.01)
*G01N 33/60* (2006.01)

(52) U.S. Cl. ........ 435/7.23; 435/7.1; 435/7.2; 435/7.21; 435/7.6; 436/501; 436/503; 436/504; 436/63; 436/64

(58) Field of Classification Search ............ 435/7.1, 435/7.2, 7.21, 7.23, 7.6; 436/501, 503, 504, 436/63, 64
See application file for complete search history.

(56) References Cited

U.S. PATENT DOCUMENTS

| | | | |
|---|---|---|---|
| 5,279,966 A | 1/1994 | Jessell et al. | |
| 5,871,969 A | 2/1999 | Hastings et al. | |
| 6,287,777 B1 | 9/2001 | Sytkowski et al. | |
| 6,465,620 B1 | 10/2002 | Boyle et al. | |
| 6,569,662 B1 | 5/2003 | Tang et al. | |
| 6,586,390 B1 | 7/2003 | Haley et al. | |
| 6,682,902 B2 | 1/2004 | Harkins et al. | |
| 6,759,512 B1 | 7/2004 | Hastings et al. | |
| 6,916,648 B2 * | 7/2005 | Goddard et al. | 435/252.3 |
| 6,960,433 B1 * | 11/2005 | Ali et al. | 435/6 |
| 6,962,797 B2 | 11/2005 | Goddard et al. | |
| 6,972,325 B2 | 12/2005 | Fong et al. | |
| 6,974,696 B2 | 12/2005 | Botstein et al. | |
| 6,989,232 B2 | 1/2006 | Burgess et al. | |
| 7,019,115 B2 | 3/2006 | Desnoyers et al. | |
| 7,019,124 B2 | 3/2006 | Desnoyers et al. | |
| 7,029,874 B2 | 4/2006 | Baker et al. | |
| 7,033,790 B2 | 4/2006 | Patturajan | |
| 7,037,710 B2 | 5/2006 | Goddard et al. | |
| 7,067,301 B2 | 6/2006 | Haley et al. | |
| 7,067,628 B2 | 6/2006 | Desnoyers et al. | |
| 7,067,636 B2 | 6/2006 | Desnoyers et al. | |
| 7,074,593 B2 | 7/2006 | Goddard et al. | |
| 7,081,521 B2 | 7/2006 | Desnoyers et al. | |
| 2002/0004047 A1 | 1/2002 | Harkins et al. | |
| 2002/0068036 A1 | 6/2002 | Hevezi et al. | |
| 2002/0137135 A1 | 9/2002 | Sytkowski et al. | |
| 2002/0142953 A1 | 10/2002 | Ballinger et al. | |
| 2002/0146692 A1 | 10/2002 | Yamazaki et al. | |
| 2002/0156006 A1 | 10/2002 | Ashkenazi et al. | |
| 2002/0169284 A1 | 11/2002 | Ashkenazi et al. | |
| 2002/0177553 A1 | 11/2002 | Ashkenazi et al. | |
| 2002/0192706 A1 | 12/2002 | Ashkenazi et al. | |
| 2002/0197679 A1 | 12/2002 | Tang et al. | |
| 2003/0004102 A1 | 1/2003 | Ashkenazi et al. | |
| 2003/0032034 A1 | 2/2003 | Tang | |

(Continued)

FOREIGN PATENT DOCUMENTS

DE        100 50 274 A1    4/2002

(Continued)

OTHER PUBLICATIONS

Djavan, B., et al. Urology, 54: 603-606, 1999.*
Manda, R., et al. Genomics, 61: 5-14, 1999.*
Chevinsky, A.H., Semin. Surg. Oncol., 7(3): 162-166, 1991; abstract only.*
Ohshio, G., et al., Tumori, 81: 67-73, 1995.*
Mizushima, Y., et al., Oncology, 47: 43-48, 1990.*
Engelin, M. J. A., et al. Gynecologic Oncology, 78: 16-20, 2000.*
Lederman et al (Molecular Immunology 28:1171-1181, 1991).*
Li et al (Proc. Natl. Acad. Sci. USA 77:3211-3214, 1980).*
English Translation of DE 100 50 274 A1.

(Continued)

*Primary Examiner* — Alana Harris Dent
*Assistant Examiner* — Anne Holleran
(74) *Attorney, Agent, or Firm* — Licata & Tyrrell P.C.; Keith R. McCollum

(57) ABSTRACT

This invention relates to a method for assessing risk of prostate cancer. Specifically, it relates to utilizing both Pro108 and Prostate Specific Antigen (PSA) in combination to determine the risk of prostate cancer. In addition, it is directed to a method for assessing risk of ovarian, colon, breast or stomach cancer utilizing Pro108 or specific antibodies to Pro108. The invention provides isolated anti-prostate, ovarian, colon, breast or stomach cancer antigen (Pro108) antibodies that bind to Pro108 on a mammalian cell in vivo. The invention also encompasses compositions comprising an anti-Pro108 antibody and a carrier. These compositions can be provided in an article of manufacture or a kit. Another aspect of the invention is an isolated nucleic acid encoding an anti-Pro108 antibody, as well as an expression vector comprising the isolated nucleic acid. Also provided are cells that produce the anti-Pro108 antibodies. The invention encompasses a method of producing the anti-Pro108 antibodies. Other aspects of the invention are a method of killing an Pro108-expressing cancer cell, comprising contacting Pro108 present in the ECM with an anti-Pro108 antibody and a method of alleviating or treating an Pro108-expressing cancer in a mammal, comprising administering a therapeutically effective amount of the anti-Pro108 antibody to the mammal.

51 Claims, 8 Drawing Sheets

U.S. PATENT DOCUMENTS

| | | |
|---|---|---|
| 2003/0045462 A1 | 3/2003 | Ashkenazi et al. |
| 2003/0049633 A1 | 3/2003 | Ashkenazi et al. |
| 2003/0049684 A1 | 3/2003 | Ashkenazi et al. |
| 2003/0050239 A1 | 3/2003 | Ashkenazi et al. |
| 2003/0050240 A1 | 3/2003 | Ashkenazi et al. |
| 2003/0050241 A1 | 3/2003 | Ashkenazi et al. |
| 2003/0054405 A1 | 3/2003 | Ashkenazi et al. |
| 2003/0054986 A1 | 3/2003 | Ashkenazi et al. |
| 2003/0055216 A1 | 3/2003 | Ashkenazi et al. |
| 2003/0060406 A1 | 3/2003 | Ashkenazi et al. |
| 2003/0064369 A1 | 4/2003 | Taupier, Jr. et al. |
| 2003/0064407 A1 | 4/2003 | Ashkenazi et al. |
| 2003/0068648 A1 | 4/2003 | Ashkenazi et al. |
| 2003/0069178 A1 | 4/2003 | Ashkenazi et al. |
| 2003/0072745 A1 | 4/2003 | Ashkenazi et al. |
| 2003/0073131 A1 | 4/2003 | Ashkenazi et al. |
| 2003/0073624 A1 | 4/2003 | Ashkenazi et al. |
| 2003/0077700 A1 | 4/2003 | Ashkenazi et al. |
| 2003/0083248 A1 | 5/2003 | Ashkenazi et al. |
| 2003/0087245 A1 | 5/2003 | Gish et al. |
| 2003/0096744 A1 | 5/2003 | Ashkenazi et al. |
| 2003/0104529 A1 | 6/2003 | Zhou et al. |
| 2003/0104536 A1 | 6/2003 | Ashkenazi et al. |
| 2003/0104998 A1 | 6/2003 | Ashkenazi et al. |
| 2003/0108544 A1* | 6/2003 | Gurney et al. ............. 424/141.1 |
| 2003/0108963 A1 | 6/2003 | Schlegel et al. |
| 2003/0124579 A1 | 7/2003 | Mack et al. |
| 2003/0130181 A1 | 7/2003 | Ashkenazi et al. |
| 2003/0134280 A1 | 7/2003 | Munger et al. |
| 2003/0134324 A1 | 7/2003 | Munger et al. |
| 2003/0134785 A1 | 7/2003 | Ashkenazi et al. |
| 2003/0138439 A1 | 7/2003 | Ashkenazi et al. |
| 2003/0139328 A1 | 7/2003 | Ashkenazi et al. |
| 2003/0147901 A1 | 8/2003 | Ashkenazi et al. |
| 2003/0148373 A1 | 8/2003 | Ashkenazi et al. |
| 2003/0148376 A1 | 8/2003 | Ashkenazi et al. |
| 2003/0157615 A1 | 8/2003 | Ashkenazi et al. |
| 2003/0166152 A1 | 9/2003 | Haley et al. |
| 2003/0170254 A1 | 9/2003 | Ashkenazi et al. |
| 2003/0180310 A1 | 9/2003 | Ashkenazi et al. |
| 2003/0180311 A1 | 9/2003 | Ashkenazi et al. |
| 2003/0180867 A1 | 9/2003 | Ashkenazi et al. |
| 2003/0185815 A1 | 10/2003 | Padigaru et al. |
| 2003/0185841 A1 | 10/2003 | Ashkenazi et al. |
| 2003/0186365 A1 | 10/2003 | Ashkenazi et al. |
| 2003/0186368 A1 | 10/2003 | Ashkenazi et al. |
| 2003/0187241 A1 | 10/2003 | Ashkenazi et al. |
| 2003/0190321 A1 | 10/2003 | Ashkenazi et al. |
| 2003/0190640 A1 | 10/2003 | Faris et al. |
| 2003/0190701 A1 | 10/2003 | Ashkenazi et al. |
| 2003/0190703 A1 | 10/2003 | Ashkenazi et al. |
| 2003/0194410 A1 | 10/2003 | Ashkenazi et al. |
| 2003/0194744 A1 | 10/2003 | Ashkenazi et al. |
| 2003/0194780 A1 | 10/2003 | Ashkenazi et al. |
| 2003/0194781 A1 | 10/2003 | Ashkenazi et al. |
| 2003/0195148 A1 | 10/2003 | Ashkenazi et al. |
| 2003/0195333 A1 | 10/2003 | Ashkenazi et al. |
| 2003/0195344 A1 | 10/2003 | Ashkenazi et al. |
| 2003/0195345 A1 | 10/2003 | Ashkenazi et al. |
| 2003/0198994 A1 | 10/2003 | Ashkenazi et al. |
| 2003/0199021 A1 | 10/2003 | Ashkenazi et al. |
| 2003/0199435 A1 | 10/2003 | Ashkenazi et al. |
| 2003/0199436 A1 | 10/2003 | Ashkenazi et al. |
| 2003/0199437 A1 | 10/2003 | Ashkenazi et al. |
| 2003/0199674 A1 | 10/2003 | Ashkenazi et al. |
| 2003/0203402 A1 | 10/2003 | Ashkenazi et al. |
| 2003/0203433 A1 | 10/2003 | Ashkenazi et al. |
| 2003/0203434 A1 | 10/2003 | Ashkenazi et al. |
| 2003/0203435 A1 | 10/2003 | Ashkenazi et al. |
| 2003/0203436 A1 | 10/2003 | Ashkenazi et al. |
| 2003/0203441 A1 | 10/2003 | Ashkenazi et al. |
| 2003/0203442 A1 | 10/2003 | Ashkenazi et al. |
| 2003/0203443 A1 | 10/2003 | Ashkenazi et al. |
| 2003/0203444 A1 | 10/2003 | Ashkenazi et al. |
| 2003/0203445 A1 | 10/2003 | Ashkenazi et al. |
| 2003/0203446 A1 | 10/2003 | Ashkenazi et al. |
| 2003/0203843 A1 | 10/2003 | Pena et al. |
| 2003/0204052 A1 | 10/2003 | Herrmann et al. |
| 2003/0204055 A1 | 10/2003 | Ashkenazi et al. |
| 2003/0206915 A1 | 11/2003 | Ashkenazi et al. |
| 2003/0207394 A1 | 11/2003 | Alsobrook, II et al. |
| 2003/0207803 A1 | 11/2003 | Ashkenazi et al. |
| 2003/0211091 A1 | 11/2003 | Ashkenazi et al. |
| 2003/0211092 A1 | 11/2003 | Ashkenazi et al. |
| 2003/0211987 A1 | 11/2003 | Labat et al. |
| 2003/0212256 A1 | 11/2003 | Edinger et al. |
| 2003/0212257 A1 | 11/2003 | Spytek et al. |
| 2003/0215905 A1 | 11/2003 | Ashkenazi et al. |
| 2003/0215908 A1 | 11/2003 | Ashkenazi et al. |
| 2003/0216305 A1 | 11/2003 | Ashkenazi et al. |
| 2003/0216560 A1 | 11/2003 | Ashkenazi et al. |
| 2003/0216561 A1 | 11/2003 | Ashkenazi et al. |
| 2003/0218283 A1 | 11/2003 | Yasumura et al. |
| 2003/0219744 A1 | 11/2003 | Tang et al. |
| 2003/0224379 A1 | 12/2003 | Tang et al. |
| 2003/0232350 A1 | 12/2003 | Afar et al. |
| 2004/0005312 A1 | 1/2004 | Ashkenazi et al. |
| 2004/0005563 A1 | 1/2004 | Mack et al. |
| 2004/0005657 A1 | 1/2004 | Ashkenazi et al. |
| 2004/0006219 A1 | 1/2004 | Ashkenazi et al. |
| 2004/0009907 A1 | 1/2004 | Alsobrook, II et al. |
| 2004/0010119 A1 | 1/2004 | Guo et al. |
| 2004/0023307 A1 | 2/2004 | Harkins et al. |
| 2004/0029218 A1 | 2/2004 | Ashkenazi et al. |
| 2004/0030110 A1 | 2/2004 | Guo et al. |
| 2004/0039163 A1 | 2/2004 | Burgess et al. |
| 2004/0048249 A1 | 3/2004 | Tang et al. |
| 2004/0048332 A1 | 3/2004 | Ashkenazi et al. |
| 2004/0058338 A1 | 3/2004 | Agee et al. |
| 2004/0063921 A1 | 4/2004 | Ashkenazi et al. |
| 2004/0072227 A1 | 4/2004 | Jonak et al. |
| 2004/0076955 A1 | 4/2004 | Mack et al. |
| 2004/0096877 A1 | 5/2004 | Taupier, Jr. et al. |
| 2004/0146928 A1 | 7/2004 | Hastings et al. |
| 2004/0152139 A1 | 8/2004 | Harkins et al. |
| 2004/0209310 A1 | 10/2004 | Sudhof et al. |
| 2004/0219521 A1 | 11/2004 | Tang et al. |
| 2004/0223964 A1 | 11/2004 | Ashkenazi et al. |
| 2004/0253606 A1 | 12/2004 | Aziz et al. |
| 2005/0014226 A1 | 1/2005 | Ashkenazi et al. |
| 2005/0019845 A1 | 1/2005 | Harkins et al. |
| 2005/0026823 A1 | 2/2005 | Zankel et al. |
| 2005/0037458 A1 | 2/2005 | Ashkenazi et al. |
| 2005/0037463 A1 | 2/2005 | Ashkenazi et al. |
| 2005/0042227 A1 | 2/2005 | Zankel et al. |
| 2005/0079577 A1 | 4/2005 | Ashkenazi et al. |
| 2005/0084935 A1 | 4/2005 | Ashkenazi et al. |
| 2005/0124012 A1 | 6/2005 | Simon et al. |
| 2005/0124789 A9 | 6/2005 | Ashkenazi et al. |
| 2005/0130193 A1 | 6/2005 | Luxon et al. |
| 2005/0170374 A1 | 8/2005 | Tang et al. |
| 2005/0175994 A1 | 8/2005 | Haley-Vicente et al. |
| 2005/0191673 A1 | 9/2005 | Schlegel et al. |
| 2005/0192215 A1 | 9/2005 | Ghosh et al. |
| 2005/0208488 A1 | 9/2005 | Boyle et al. |
| 2005/0208500 A1 | 9/2005 | Erlander et al. |
| 2005/0227328 A1 | 10/2005 | Ashkenazi et al. |
| 2005/0227342 A1 | 10/2005 | Ashkenazi et al. |
| 2005/0233328 A1 | 10/2005 | Berghs et al. |
| 2005/0239060 A1 | 10/2005 | Tang et al. |
| 2006/0078964 A1 | 4/2006 | Ashkenazi et al. |
| 2006/0160090 A1 | 7/2006 | Macina et al. |

FOREIGN PATENT DOCUMENTS

| | | |
|---|---|---|
| DE | 100 50 274 AL | 4/2002 |
| EP | 1 130 094 A2 | 9/2001 |
| EP | 1 251 139 A2 | 10/2002 |
| EP | 1 251 139 A3 | 12/2003 |
| EP | 1 394 274 A2 | 3/2004 |
| EP | 1 396 543 A2 | 3/2004 |
| EP | 1 466 977 A1 | 10/2004 |
| EP | 1 484 338 A1 | 12/2004 |
| EP | 1 686 175 A2 | 2/2006 |
| EP | 1 686 175 A2 | 8/2006 |
| WO | WO 93/20196 | 10/1993 |
| WO | WO98/45442 | * 10/1998 |
| WO | WO 98/50073 | 11/1998 |

| | | |
|---|---|---|
| WO | WO 99/41412 | 8/1999 |
| WO | WO 99/46281 | 9/1999 |
| WO | WO 00/23108 | 4/2000 |
| WO | WO 00/37638 | 6/2000 |
| WO | WO 00/53756 | 9/2000 |
| WO | WO 00/053756 | 9/2000 |
| WO | WO 00/55199 | 9/2000 |
| WO | WO 01/44291 A2 | 6/2001 |
| WO | WO 01/47944 A2 | 7/2001 |
| WO | WO 01/49879 A2 | 7/2001 |
| WO | WO 01/53312 A1 | 7/2001 |
| WO | WO 02/10216 | 2/2002 |
| WO | WO 02/12440 A2 | 2/2002 |
| WO | WO 02/16599 A2 | 2/2002 |
| WO | WO 02/29038 A2 | 4/2002 |
| WO | WO 02/30268 A2 | 4/2002 |
| WO | WO 02/31496 A2 | 4/2002 |
| WO | WO 02/31496 A3 | 4/2002 |
| WO | WO 02/33087 A2 | 4/2002 |
| WO | WO 02/33807 A2 | 4/2002 |
| WO | WO 02/068652 A2 | 9/2002 |
| WO | WO 02/085922 A2 | 10/2002 |
| WO | WO 02/098358 A2 | 12/2002 |
| WO | WO 02/102235 A2 | 12/2002 |
| WO | WO 03/003906 A2 | 1/2003 |
| WO | WO 03/009814 A2 | 2/2003 |
| WO | WO 03/025138 A2 | 3/2003 |
| WO | WO 03/027633 A2 | 4/2003 |
| WO | WO 03/029405 A2 | 4/2003 |
| WO | WO 03/042661 A2 | 5/2003 |
| WO | WO 03/064624 A2 | 8/2003 |
| WO | WO 03/074654 A2 | 9/2003 |
| WO | WO 2004/005883 A2 | 1/2004 |
| WO | WO 2004/043361 A2 | 5/2004 |
| WO | WO 2004/048938 A2 | 6/2004 |
| WO | WO 2004/076614 A2 | 9/2004 |
| WO | WO 2004/078135 A2 | 9/2004 |
| WO | WO 2004/092338 A2 | 10/2004 |
| WO | WO 2005/002515 A2 | 1/2005 |
| WO | WO 2005/003766 A2 | 1/2005 |
| WO | WO 2005/010048 A2 | 2/2005 |
| WO | WO 2005/010213 A2 | 2/2005 |
| WO | WO 2005/024603 A2 | 3/2005 |
| WO | WO 2005/040418 A2 | 3/2005 |
| WO | WO 2005/040418 A3 | 5/2005 |
| WO | WO 2005/045044 A2 | 5/2005 |
| WO | WO 2005/082934 A2 | 9/2005 |
| WO | WO 2005/098032 A1 | 10/2005 |
| WO | WO 2005/117943 A2 | 12/2005 |
| WO | WO 2005/118641 A1 | 12/2005 |
| WO | WO 2005/122712 A2 | 12/2005 |
| WO | WO 2006/012451 A2 | 2/2006 |
| WO | WO 2006/028655 A2 | 3/2006 |
| WO | WO 2006/048263 A2 | 5/2006 |

OTHER PUBLICATIONS

NCBI Genbank Accession No. NM_012445 [gi:6912681] with Revision History Feb. 7, 2000-Aug. 22, 2004.
NCBI Genbank Accession No. NP_036577 [gi:6912682] with Revision History Feb. 7, 2000-Aug. 22, 2004.
Adams et al., "The Thrombospondin Type 1 Repeat (TSR) Superfamily:Diverse Proteins With Related Roles in Neuronal Development", Developmental Dynamics 2000 218:280-299.
Buckland, J., "Pathogens mind out!", Nature Reviews 2004 2:89.
Clark et al., "The Secreted Protein Discovery Initiative (SPDI), a Large-Scale Effort to Identify Novel Human Secreted and Transmembrane Proteins: A Bioinformatics Assessment", Genome Research 2003 13:2265-2270.
dePeredo et al., "C-Mannosylation and O-Fucosylation of Thrombospondin Type 1 Repeats", Molecular & Cellular Proteomics 2002 1:11-18.
Edwards et al., "Expression analysis onto microarrays of randomly selected cDNA clones highlights HOXBI3 as a marker of human prostate cancer", British Journal of Cancer 2005 92:376-381.
Feinstein et al., "F-spondin and mindin:two structurally and functionally related genes expressed in the hippocampus that promote outgrowth of embryonic hippocampal neurons", Development 1999 126:3637-3648.
Feinstein et al., "The neuronal class 2 TSR proteins F-spondin and Mindin:a small family with divergent biological activities", International Journal of Biochemistry & Cell Biology 2004 36:975-980.
Fernández-Llebrez et al., "Analysis and Quantification of the Secretory Products of the Subcommissural Organ by Use of Monoclonal Antibodies", Microscopy Research and Technique 2001 52:510-519.
Gobron et al., "SCO-spondin:a new member of the thrombospondin family secreted by the subcommissural organ is a candidate in the modulation of neuronal aggregation", Journal of Cell Sciences 1996 109:1053-1061.
He et al., "The extracellular matrix protein mindin is a pattern-recognition molecule for microbial pathogens", Nature Immunology 2004 5(1):88-97.
Higashijima et al., "Mindin/F-spondin Family:Novel ECM Proteins Expressed in the Zebrafish Embryonic Axis", Developmental Biology 1997 192:211-227.
Jia et al., "The extracellular matrix protein mindin serves as an integrin ligand and is critical for inflammatory cell recruitment", Blood 2005 106(12):3854-3859.
Kazanskaya et al., "R-Spondin2 Is a Secreted Activator of Wnt/B-Catenin Signaling and Is Required for Xenopus Myogenesis", Developmental Cell 2004 7:525-534.
Manda et al., "Identification of Genes (SPON2 and C20orf2) Differentially Expressed between Cancerous and Noncancerous Lung Cells by mRNA Differential Display", Genomics 1999 61:5-14.
McDonald et al., "Mindin the fort", Nature Immunology 2004 5(1):16-18.
Parry et al., "Identification of a Novel Prostate Tumor Target, Mindin/RG-1, for Antibody-Based Radiotherapy of Prostate Cancer", Cancer Res. 2005 65(18):8397-8405.
Pham et al., "Rapid on-membrane proteolytic cleavage for Edman sequencing and mass spectrometric identification of proteins", Electrophoresis 2005 26:4243-4251.
Shimeld, Sebastian M., "Characterization of AmphiF-spondin Reveals the Modular Evolution of Chordate F-spondin Genes", Mol. Biol. Evol. 1998 15(9):1218-1223.
Strausberg et al., "Generation and initial analysis of more than 15,000 full-length human and mouse cDNA sequences", Proc. Natl. Acad. Sci. USA 2002 99(26):16899-16903.
Tzarfaty-Majar et al., "Plasmin-mediated Release of the Guidance Molecule F-spondin from the Extracellular Matrix", J. Biol. Chem. 2001 276(30):28233-28241.
Umemiya et al., "M-Spondin, a Novel ECM Protein Highly Homologous to Vertebrate F-Spondin, Is Localized at the Muscle Attachment Sites in the Drosophila Embryo", Developmental Biology 1997 186:165-176.
English Translation of DE 100 50 274 A1, 2006.

* cited by examiner

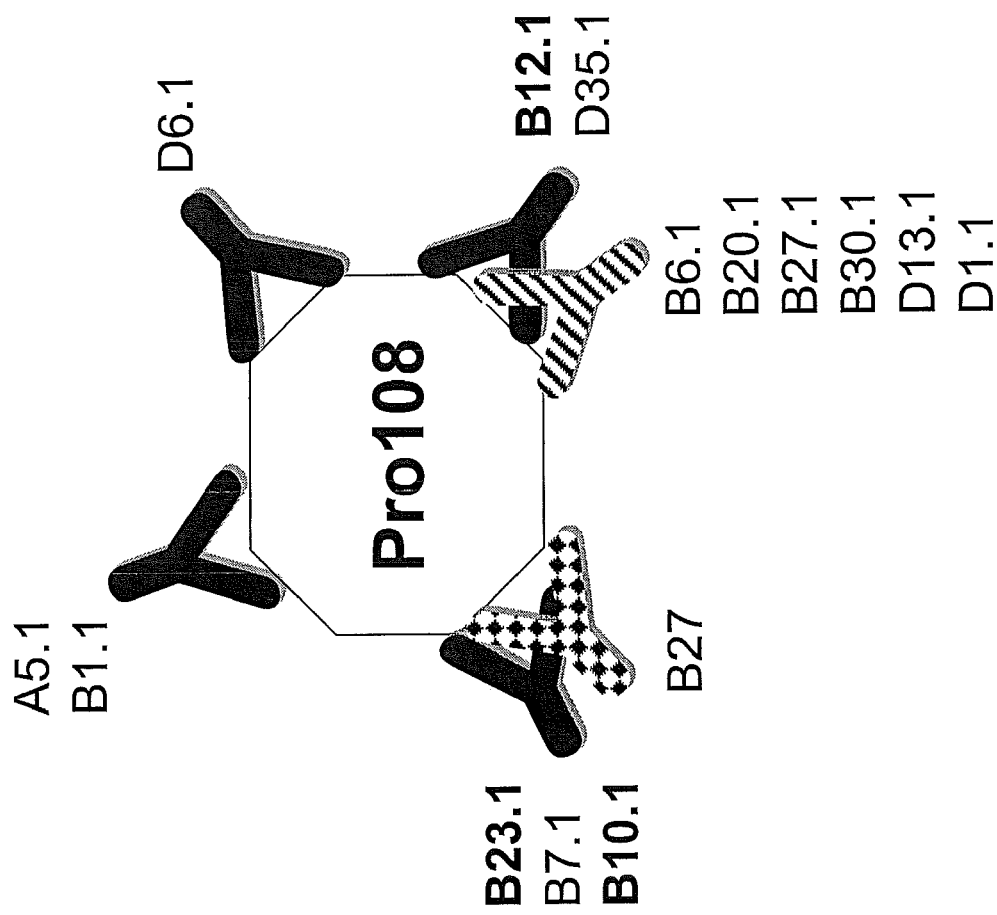

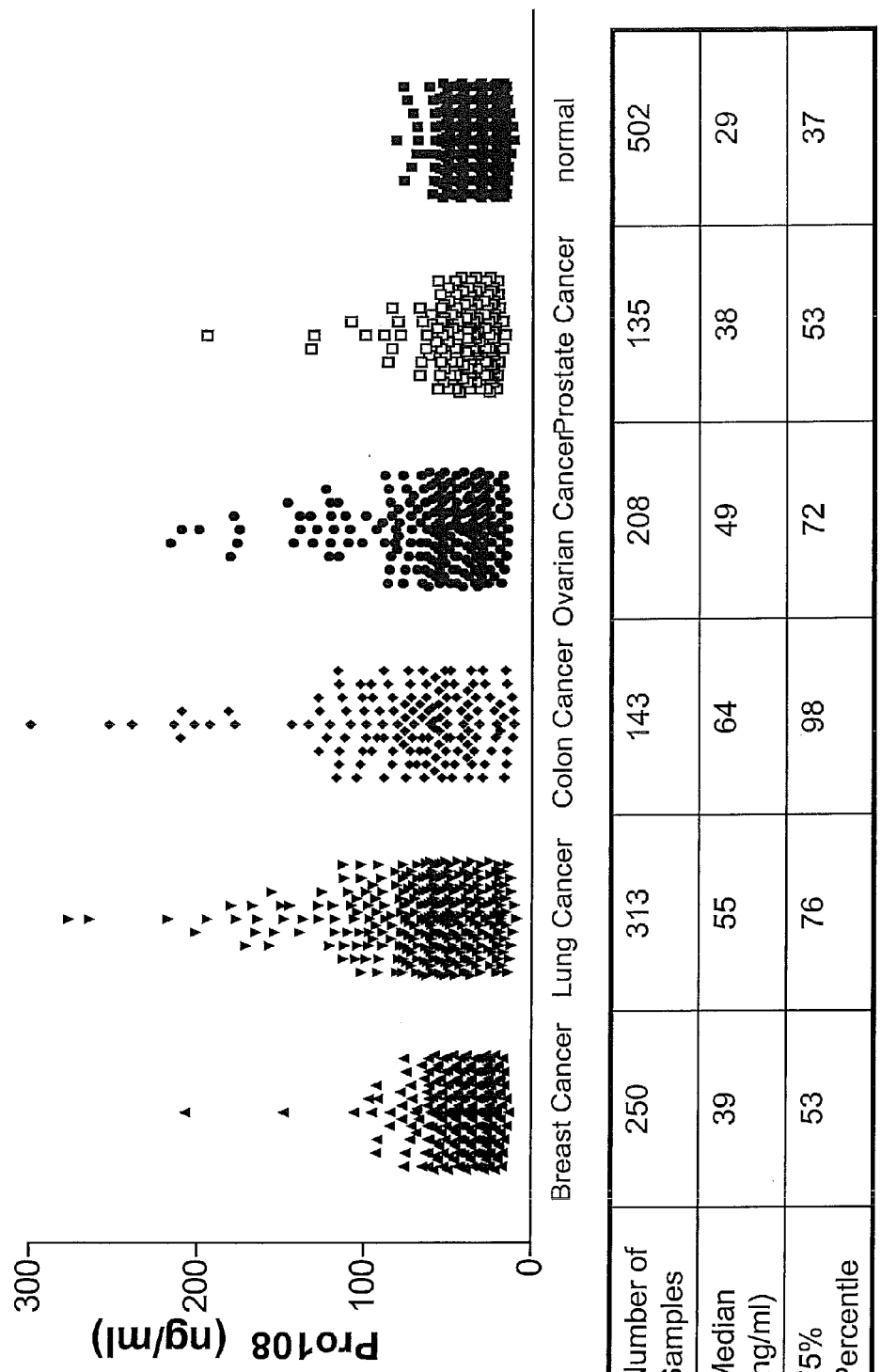
Figure 2: Pro108 serum levels in healthy subjects and subjects with various cancers.

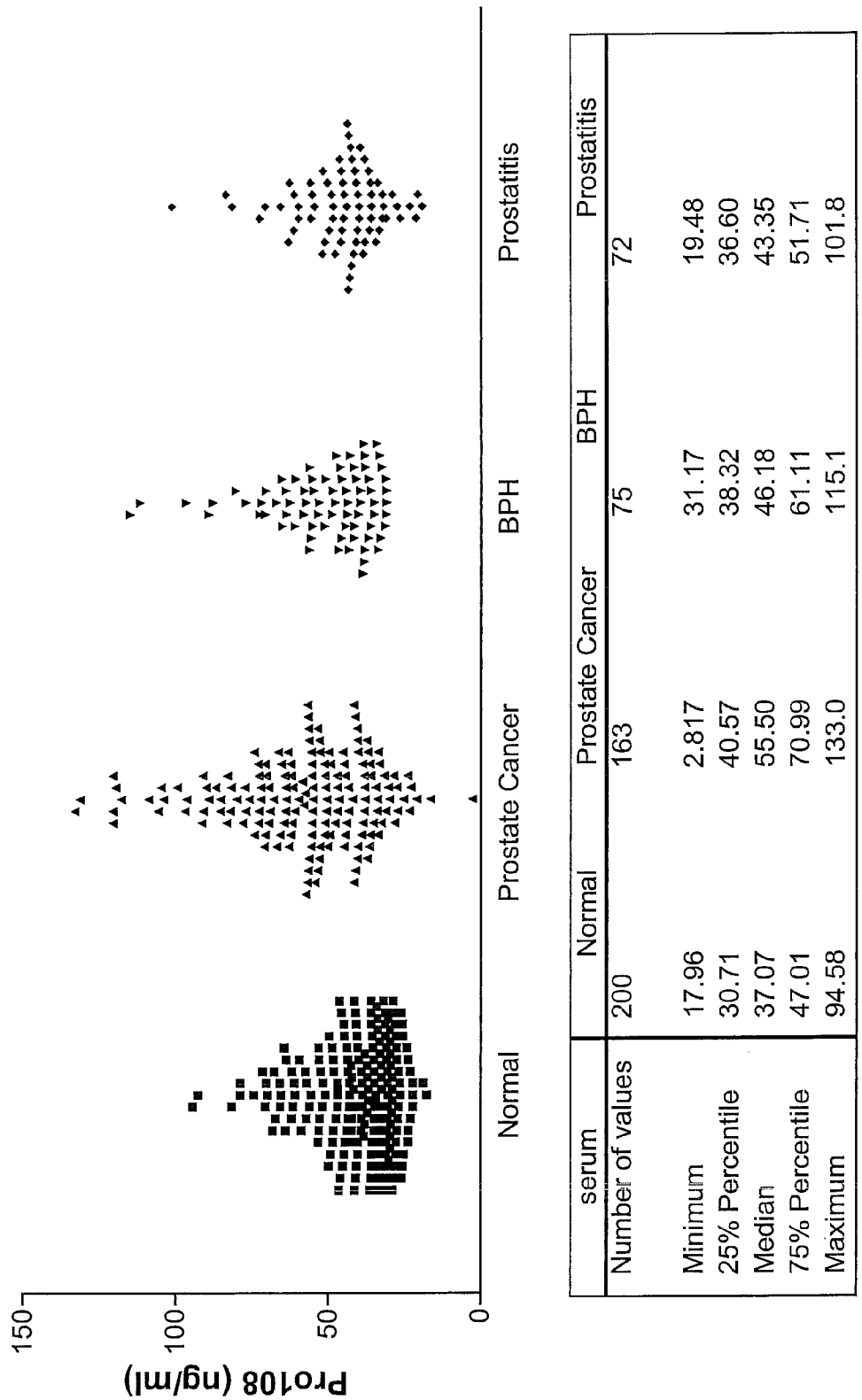
Figure 3: Pro108 levels in prostate cancer and benign prostate disease.

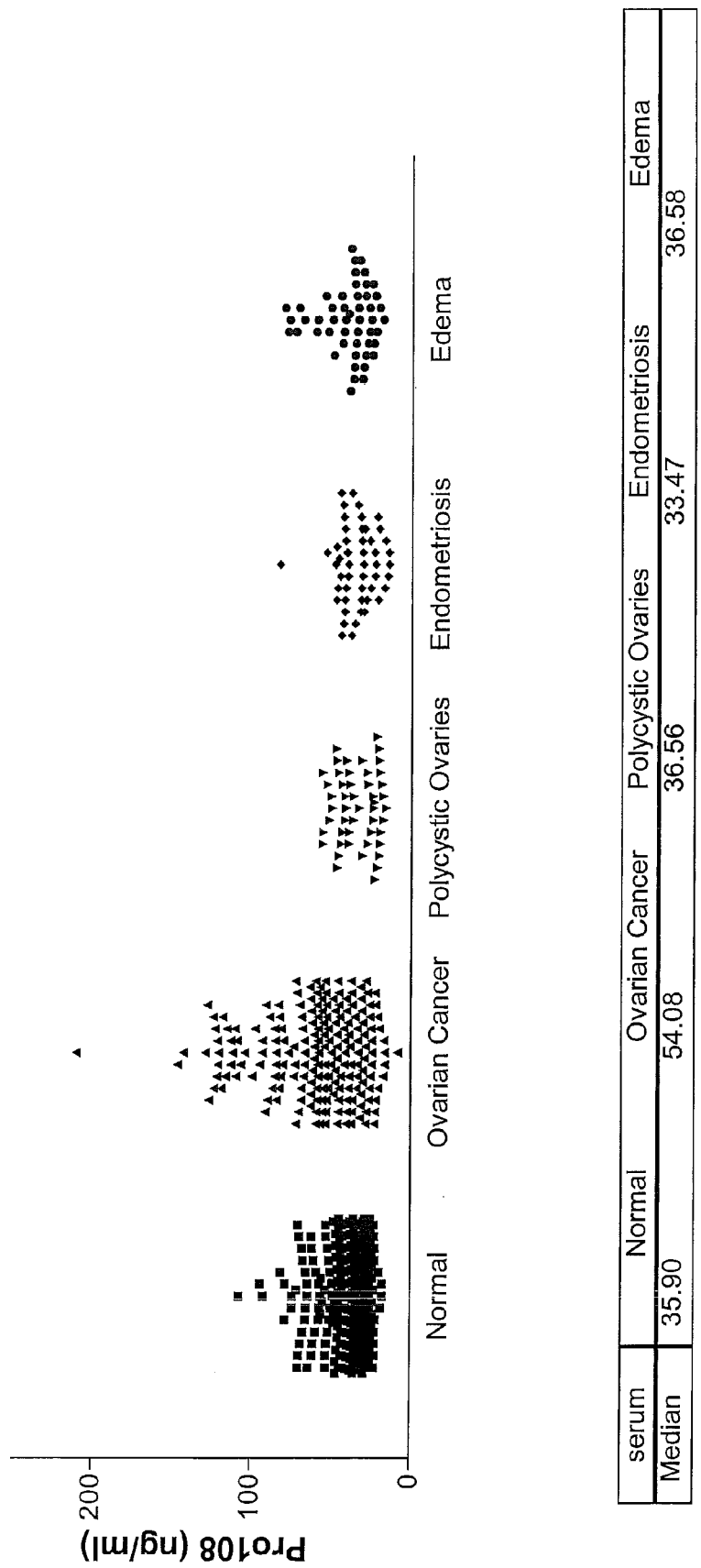
Figure 4: Pro108 levels in ovarian cancer and benign ovarian disease.
| serum | Normal | Ovarian Cancer | Polycystic Ovaries | Endometriosis | Edema |
|---|---|---|---|---|---|
| Median | 35.90 | 54.08 | 36.56 | 33.47 | 36.58 |

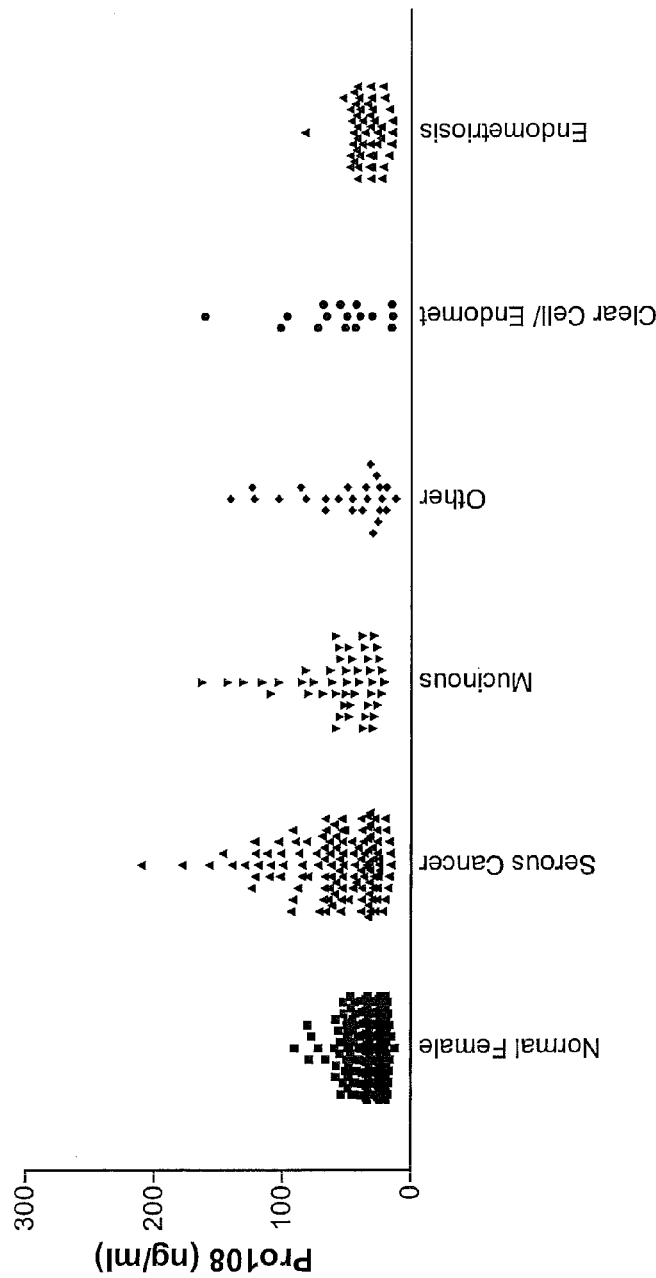
Figure 5: Pro108 levels in serous and mucinous ovarian cancer and in benign ovarian disease.
| X Labels | Normal Female | Serous Cancer | Mucinous | Other | Clear Cell/ Endomet | Endometriosis |
|---|---|---|---|---|---|---|
| Number of values | 192 | 123 | 48 | 25 | 16 | 50 |
| Minimum | 12.48 | 15.34 | 20.70 | 11.88 | 14.31 | 14.51 |
| 25% Percentile | 23.23 | 31.97 | 32.77 | 25.24 | 35.10 | 26.37 |
| Median | 29.85 | 53.10 | 48.88 | 38.22 | 51.17 | 33.47 |
| 75% Percentile | 39.78 | 71.88 | 62.85 | 74.68 | 70.93 | 43.07 |
| Maximum | 90.92 | 210.7 | 163.4 | 140.9 | 161.1 | 83.22 |

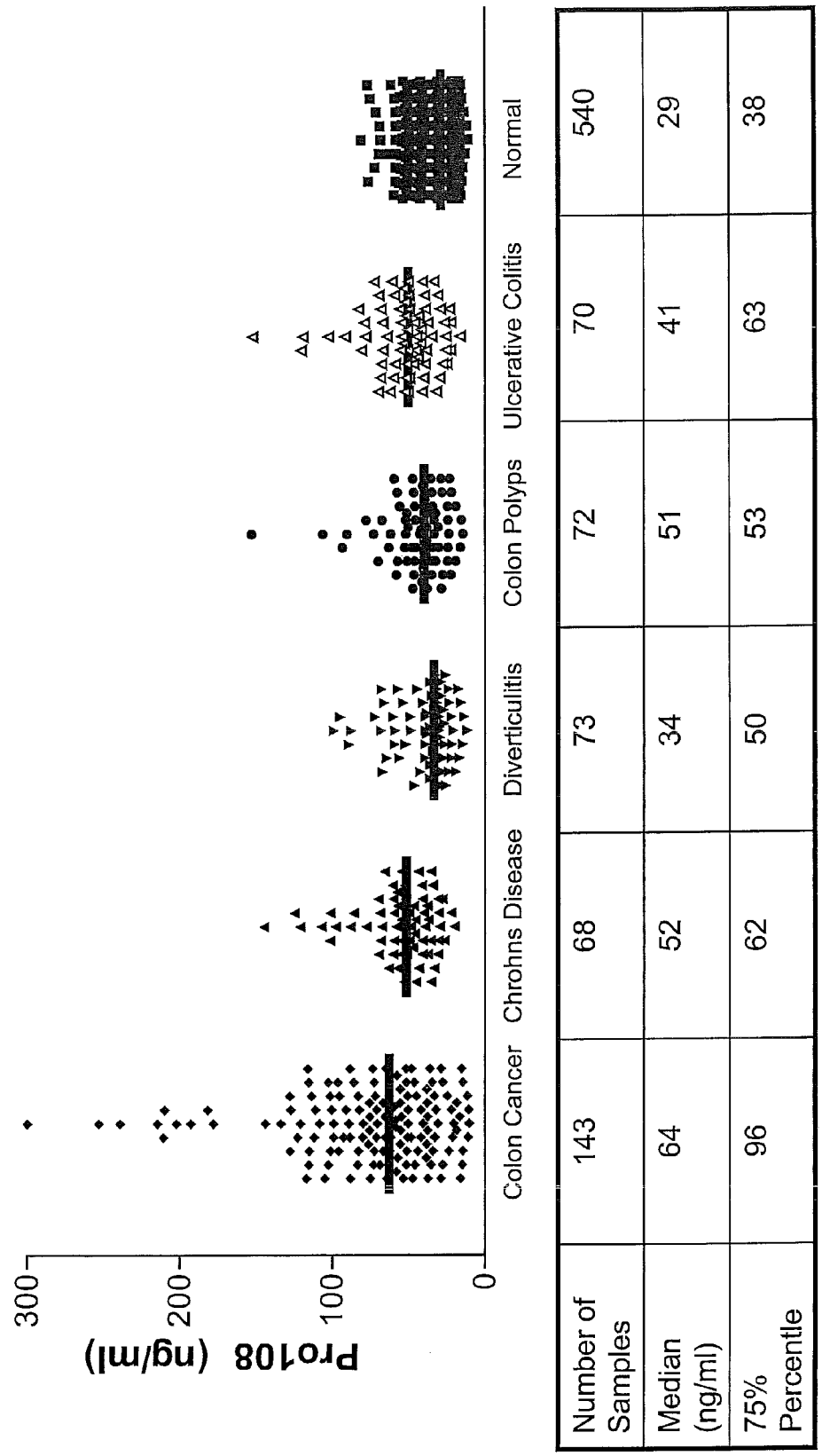
Figure 6: Pro108 levels in colon cancer and benign colon disease.

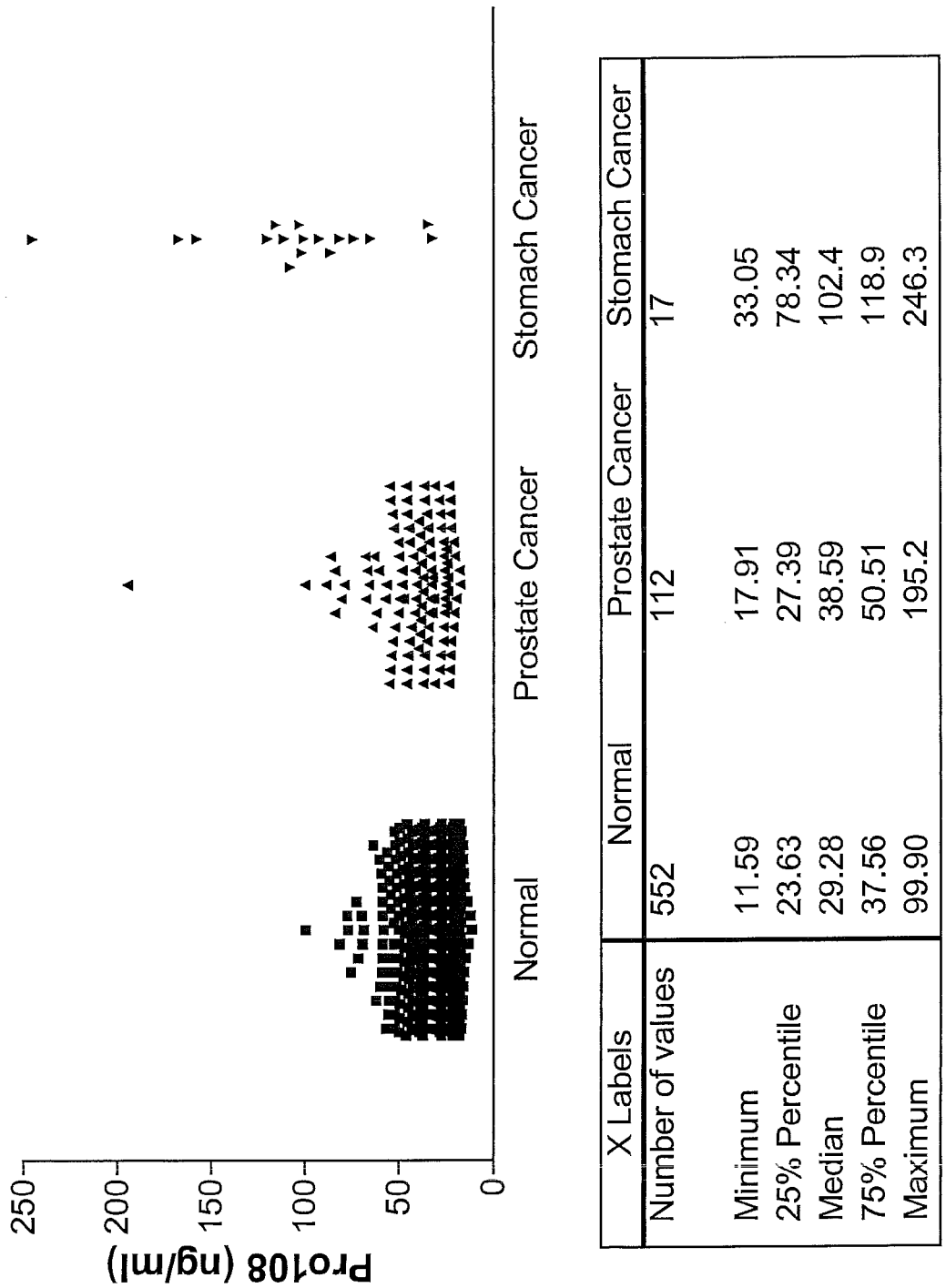
Figure 7: Pro108 levels in stomach cancer.

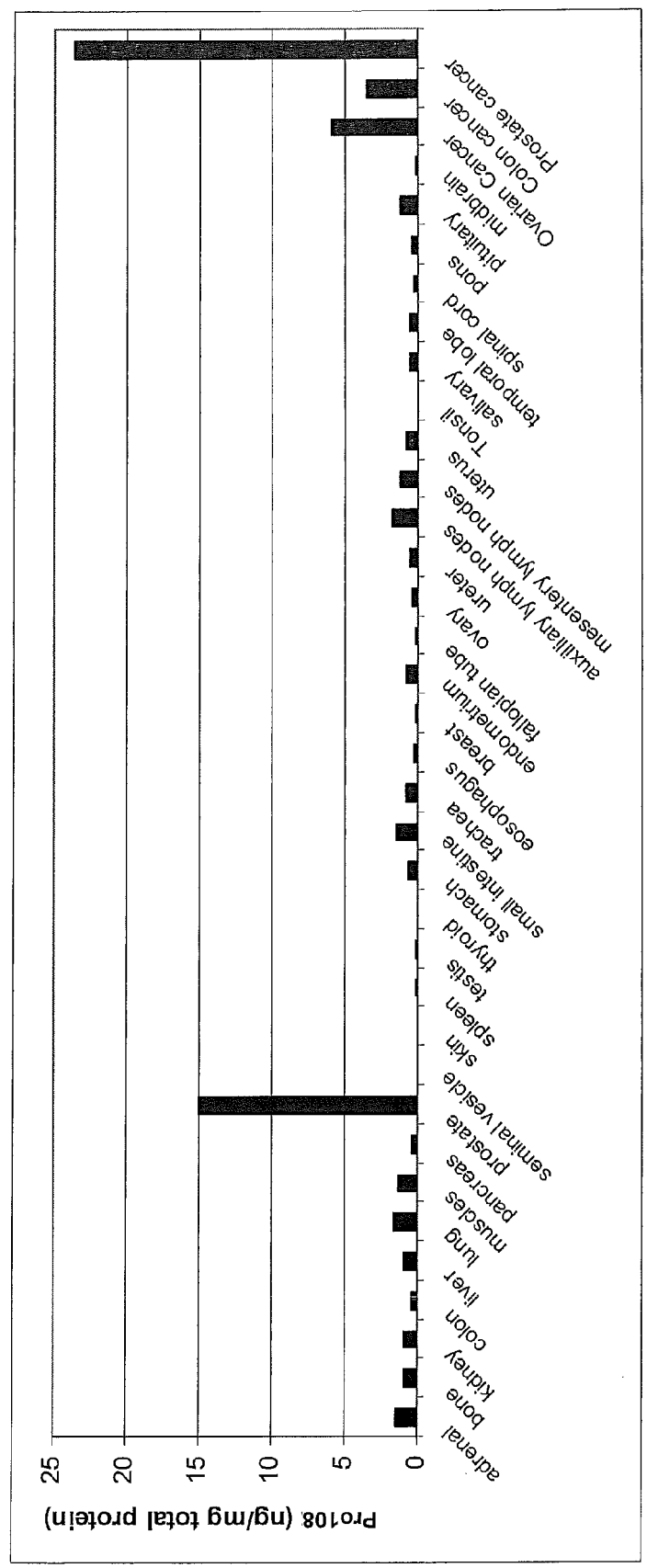
Figure 8: Detection of Pro108 in the lysate of normal somatic and cancer tissues.

SEQUENCE LISTING

```
<160> NUMBER OF SEQ ID NOS: 3

<210> SEQ ID NO 1
<211> LENGTH: 349
<212> TYPE: PRT
<213> ORGANISM: Artificial sequence
<220> FEATURE:
<223> OTHER INFORMATION: Synthetic

<400> SEQUENCE: 1

Met Glu Asn Pro Ser Pro Ala Ala Ala Leu Gly Lys Ala Leu Cys Ala
1               5                   10                  15

Leu Leu Leu Ala Thr Leu Gly Ala Ala Gly Gln Pro Leu Gly Gly Glu
            20                  25                  30

Ser Ile Cys Ser Ala Arg Ala Pro Ala Lys Tyr Ser Ile Thr Phe Thr
        35                  40                  45

Gly Lys Trp Ser Gln Thr Ala Phe Pro Lys Gln Tyr Pro Leu Phe Arg
    50                  55                  60

Pro Pro Ala Gln Trp Ser Ser Leu Leu Gly Ala Ala His Ser Ser Asp
65                  70                  75                  80

Tyr Ser Met Trp Arg Lys Asn Gln Tyr Val Ser Asn Gly Leu Arg Asp
                85                  90                  95

Phe Ala Glu Arg Gly Glu Ala Trp Ala Leu Met Lys Glu Ile Glu Ala
            100                 105                 110

Ala Gly Glu Ala Leu Gln Ser Val His Glu Val Phe Ser Ala Pro Ala
        115                 120                 125

Val Pro Ser Gly Thr Gly Gln Thr Ser Ala Glu Leu Glu Val Gln Arg
    130                 135                 140

Arg His Ser Leu Val Ser Phe Val Val Arg Ile Val Pro Ser Pro Asp
145                 150                 155                 160

Trp Phe Val Gly Val Asp Ser Leu Asp Leu Cys Asp Gly Asp Arg Trp
                165                 170                 175

Arg Glu Gln Ala Ala Leu Asp Leu Tyr Pro Tyr Asp Ala Gly Thr Asp
            180                 185                 190

Ser Gly Phe Thr Phe Ser Ser Pro Asn Phe Ala Thr Ile Pro Gln Asp
        195                 200                 205
```

```
Thr Val Thr Glu Ile Thr Ser Ser Pro Ser His Pro Ala Asn Ser
    210                 215                 220

Phe Tyr Tyr Pro Arg Leu Lys Ala Leu Pro Pro Ile Ala Arg Val Thr
225                 230                 235                 240

Leu Val Arg Leu Arg Gln Ser Pro Arg Ala Phe Ile Pro Pro Ala Pro
                245                 250                 255

Val Leu Pro Ser Arg Asp Asn Glu Ile Val Asp Ser Ala Ser Val Pro
                260                 265                 270

Glu Thr Pro Leu Asp Cys Glu Val Ser Leu Trp Ser Ser Trp Gly Leu
                275                 280                 285

Cys Gly Gly His Cys Gly Arg Leu Gly Thr Lys Ser Arg Thr Arg Tyr
                290                 295                 300

Val Arg Val Gln Pro Ala Asn Asn Gly Ser Pro Cys Pro Glu Leu Glu
305                 310                 315                 320

Glu Glu Ala Glu Cys Val Pro Asp Asn Cys Val Asp Pro Ala Phe Leu
                325                 330                 335

Tyr Lys Val Val Arg Trp Ala His His His His His
                340                 345
```

<210> SEQ ID NO 2
<211> LENGTH: 371
<212> TYPE: PRT
<213> ORGANISM: Artificial sequence
<220> FEATURE:
<223> OTHER INFORMATION: Synthetic

<400> SEQUENCE: 2

```
Met Glu Asn Pro Ser Pro Ala Ala Ala Leu Gly Lys Ala Leu Cys Ala
1                   5                   10                  15

Leu Leu Leu Ala Thr Leu Gly Ala Ala Gly Gln Pro Leu Gly Gly Glu
                20                  25                  30

Ser Ile Cys Ser Ala Arg Ala Pro Ala Lys Tyr Ser Ile Thr Phe Thr
                35                  40                  45

Gly Lys Trp Ser Gln Thr Ala Phe Pro Lys Gln Tyr Pro Leu Phe Arg
50                  55                  60

Pro Pro Ala Gln Trp Ser Ser Leu Leu Gly Ala Ala His Ser Ser Asp
65                  70                  75                  80

Tyr Ser Met Trp Arg Lys Asn Gln Tyr Val Ser Asn Gly Leu Arg Asp
                85                  90                  95

Phe Ala Glu Arg Gly Glu Ala Trp Ala Leu Met Lys Glu Ile Glu Ala
                100                 105                 110

Ala Gly Glu Ala Leu Gln Ser Val His Glu Val Phe Ser Ala Pro Ala
                115                 120                 125

Val Pro Ser Gly Thr Gly Gln Thr Ser Ala Glu Leu Glu Val Gln Arg
                130                 135                 140

Arg His Ser Leu Val Ser Phe Val Val Arg Ile Val Pro Ser Pro Asp
145                 150                 155                 160

Trp Phe Val Gly Val Asp Ser Leu Asp Leu Cys Asp Gly Asp Arg Trp
                165                 170                 175

Arg Glu Gln Ala Ala Leu Asp Leu Tyr Pro Tyr Asp Ala Gly Thr Asp
                180                 185                 190

Ser Gly Phe Thr Phe Ser Ser Pro Asn Phe Ala Thr Ile Pro Gln Asp
                195                 200                 205

Thr Val Thr Glu Ile Thr Ser Ser Pro Ser His Pro Ala Asn Ser
    210                 215                 220
```

```
Phe Tyr Tyr Pro Arg Leu Lys Ala Leu Pro Pro Ile Ala Arg Val Thr
225                 230                 235                 240

Leu Leu Arg Leu Arg Gln Ser Pro Arg Ala Phe Ile Pro Pro Ala Pro
            245                 250                 255

Val Leu Pro Ser Arg Asp Asn Glu Ile Val Asp Ser Ala Ser Val Pro
            260                 265                 270

Glu Thr Pro Leu Asp Cys Glu Val Ser Leu Trp Ser Ser Trp Gly Leu
        275                 280                 285

Cys Gly Gly His Cys Gly Arg Leu Gly Thr Lys Ser Arg Thr Arg Tyr
    290                 295                 300

Val Arg Val Gln Pro Ala Asn Asn Gly Ser Pro Cys Pro Glu Leu Glu
305                 310                 315                 320

Glu Glu Ala Glu Cys Val Pro Asp Asn Cys Val Asp Pro Ala Phe Leu
                325                 330                 335

Tyr Lys Val Val Asp Leu Glu Gly Pro Arg Phe Glu Gly Lys Pro Ile
            340                 345                 350

Pro Asn Pro Leu Leu Gly Leu Asp Ser Thr Arg Thr Gly His His His
            355                 360                 365

His His His
    370

<210> SEQ ID NO 3
<211> LENGTH: 690
<212> TYPE: PRT
<213> ORGANISM: Artificial sequence
<220> FEATURE:
<223> OTHER INFORMATION: Synthetic

<400> SEQUENCE: 3

Met Met Asp Ala Ser Lys Glu Leu Gln Val Leu His Ile Asp Phe Leu
1               5                   10                  15

Asn Gln Asp Asn Ala Val Ser His His Thr Trp Glu Phe Gln Thr Ser
                20                  25                  30

Ser Pro Val Phe Arg Arg Gly Gln Val Phe His Leu Arg Leu Val Leu
            35                  40                  45

Asn Gln Pro Leu Gln Ser Tyr His Gln Leu Lys Leu Glu Phe Ser Thr
        50                  55                  60

Gly Pro Asn Pro Ser Ile Ala Lys His Thr Leu Val Val Leu Asp Pro
65                  70                  75                  80

Arg Thr Pro Ser Asp His Tyr Asn Trp Gln Ala Thr Leu Gln Asn Glu
                85                  90                  95

Ser Gly Lys Glu Val Thr Val Ala Val Thr Ser Ser Pro Asn Ala Ile
            100                 105                 110

Leu Gly Lys Tyr Gln Leu Asn Val Lys Thr Gly Asn His Ile Leu Lys
        115                 120                 125

Ser Glu Glu Asn Ile Leu Tyr Leu Leu Phe Asn Pro Trp Cys Lys Glu
130                 135                 140

Asp Met Val Phe Met Pro Asp Glu Asp Glu Arg Lys Glu Tyr Ile Leu
145                 150                 155                 160

Asn Asp Thr Gly Cys His Tyr Val Gly Ala Ala Arg Ser Ile Lys Cys
                165                 170                 175

Lys Pro Trp Asn Phe Gly Gln Phe Glu Lys Asn Val Leu Asp Cys Cys
            180                 185                 190

Ile Ser Leu Leu Thr Glu Ser Ser Leu Lys Pro Thr Asp Arg Arg Asp
        195                 200                 205

Pro Val Leu Val Cys Arg Ala Met Cys Ala Met Met Ser Phe Glu Lys
```

-continued

```
            210                 215                 220
Gly Gln Gly Val Leu Ile Gly Asn Trp Thr Gly Asp Tyr Glu Gly Gly
225                 230                 235                 240

Thr Ala Pro Tyr Lys Trp Thr Gly Ser Ala Pro Ile Leu Gln Gln Tyr
                245                 250                 255

Tyr Asn Thr Lys Gln Ala Val Cys Phe Gly Gln Cys Trp Val Phe Ala
                260                 265                 270

Gly Ile Leu Thr Thr Val Leu Arg Ala Leu Gly Ile Pro Ala Arg Ser
                275                 280                 285

Val Thr Gly Phe Asp Ser Ala His Asp Thr Glu Arg Asn Leu Thr Val
290                 295                 300

Asp Thr Tyr Val Asn Glu Asn Gly Glu Lys Ile Thr Ser Met Thr His
305                 310                 315                 320

Asp Ser Val Trp Asn Phe His Val Trp Thr Asp Ala Trp Met Lys Arg
                325                 330                 335

Pro Asp Leu Pro Lys Gly Tyr Asp Gly Trp Gln Ala Val Asp Ala Thr
                340                 345                 350

Pro Gln Glu Arg Ser Gln Gly Val Phe Cys Cys Gly Pro Ser Pro Leu
                355                 360                 365

Thr Ala Ile Arg Lys Gly Asp Ile Phe Ile Val Tyr Asp Thr Arg Phe
                370                 375                 380

Val Phe Ser Glu Val Asn Gly Asp Arg Leu Ile Trp Leu Val Lys Met
385                 390                 395                 400

Val Asn Gly Gln Glu Glu Leu His Val Ile Ser Met Glu Thr Thr Ser
                405                 410                 415

Ile Gly Lys Asn Ile Ser Thr Lys Ala Val Gly Gln Asp Arg Arg Arg
                420                 425                 430

Asp Ile Thr Tyr Glu Tyr Lys Tyr Pro Glu Gly Ser Ser Glu Glu Arg
                435                 440                 445

Gln Val Met Asp His Ala Phe Leu Leu Leu Ser Ser Glu Arg Glu His
                450                 455                 460

Arg Arg Pro Val Lys Glu Asn Phe Leu His Met Ser Val Gln Ser Asp
465                 470                 475                 480

Asp Val Leu Leu Gly Asn Ser Val Asn Phe Thr Val Ile Leu Lys Arg
                485                 490                 495

Lys Thr Ala Ala Leu Gln Asn Val Asn Ile Leu Gly Ser Phe Glu Leu
                500                 505                 510

Gln Leu Tyr Thr Gly Lys Lys Met Ala Lys Leu Cys Asp Leu Asn Lys
                515                 520                 525

Thr Ser Gln Ile Gln Gly Gln Val Ser Glu Val Thr Leu Thr Leu Asp
                530                 535                 540

Ser Lys Thr Tyr Ile Asn Ser Leu Ala Ile Leu Asp Asp Glu Pro Val
545                 550                 555                 560

Ile Arg Gly Phe Ile Ile Ala Glu Ile Val Ser Lys Glu Ile Met
                565                 570                 575

Ala Ser Glu Val Phe Thr Ser Phe Gln Tyr Pro Glu Phe Ser Ile Glu
                580                 585                 590

Leu Pro Asn Thr Gly Arg Ile Gly Gln Leu Leu Val Cys Asn Cys Ile
                595                 600                 605

Phe Lys Asn Thr Leu Ala Ile Pro Leu Thr Asp Val Lys Phe Ser Leu
                610                 615                 620

Glu Ser Leu Gly Ile Ser Ser Leu Gln Thr Ser Asp His Gly Thr Val
625                 630                 635                 640
```

-continued

```
Gln Pro Gly Glu Thr Ile Gln Ser Gln Ile Lys Cys Thr Pro Ile Lys
                645                 650                 655

Thr Gly Pro Lys Lys Phe Ile Val Lys Leu Ser Ser Lys Gln Val Lys
            660                 665                 670

Glu Ile Asn Ala Gln Lys Ile Val Leu Ile Thr Lys His His His His
            675                 680             685

His His
   690
```

PRO108 ANTIBODY COMPOSITIONS AND METHODS OF USE AND USE OF PRO108 TO ASSESS CANCER RISK

This patent application is a divisional of U.S. patent application Ser. No. 10/919,215 filed Aug. 16, 2004, which claims the benefit of priority from U.S. Provisional Patent Application Ser. No. 60/556,465 filed Mar. 25, 2004 and U.S. Provisional Patent Application Ser. No. 60/495,759 filed Aug. 15, 2003, teachings of each of which are herein incorporated by reference in their entirety.

This patent application claims the benefit of priority of U.S. Provisional Patent Application Ser. No. 60/556,465, filed Mar. 25, 2004 and U.S. Provisional Patent Application Ser. No. 60/495,759, filed Aug. 15, 2004, each of which is herein incorporated by reference in its entirety.

FIELD OF THE INVENTION

This invention relates to a method for assessing risk for cancer. Specifically, it relates to utilizing both Pro108 (also known as Spondin 2) Prostate Specific Antigen (PSA) in combination to detect prostate cancer. In addition, it is directed to a method for assessing risk of ovarian, colon, breast or stomach cancer utilizing Pro108 or anti-Pro108 antibodies specific to Pro108. Furthermore, the present invention relates to anti-Pro108 antibody compositions and methods of inhibiting production and function or killing Pro108-expressing prostate, ovarian, colon, breast or stomach cancers cells.

BACKGROUND OF THE INVENTION

Prostate Cancer

Prostate cancer is the most prevalent cancer in men and is the second leading cause of death from cancer among males in the United States. *AJCC Cancer Staging Handbook* 203 (Irvin D. Fleming et al. eds., $5^{th}$ ed. 1998); Walter J. Burdette, *Cancer: Etiology, Diagnosis, and Treatment* 147 (1998). In 1999, it was estimated that 37,000 men in the United States would die as result of prostate cancer. Elizabeth A. Platz et al., & Edward Giovannucci, *Epidemiology of and Risk Factors for Prostate Cancer, in Management of Prostate Cancer* 21 (Eric A Klein, ed. 2000). More recently, the American Cancer Society estimated there will be 230, 110 new cases of prostate cancer and 29,900 deaths in 2004. American Cancer Society website: cancer.org of the world wide web. Cancer of the prostate typically occurs in older males, with a median age of 74 years for clinical diagnosis. Burdette, supra at 147. A man's risk of being diagnosed with invasive prostate cancer in his lifetime is one in six. Platz et al., supra at 21.

Although our understanding of the etiology of prostate cancer is incomplete, the results of extensive research in this area point to a combination of age, genetic and environmental/dietary factors. Platz et al., supra at 19; Burdette, supra at 147; Steven K. Clinton, *Diet and Nutrition in Prostate Cancer Prevention and Therapy, in Prostate Cancer: a Multidisciplinary Guide* 246-269 (Philip W. Kantoff et al. eds. 1997). Broadly speaking, genetic risk factors predisposing one to prostate cancer include race and a family history of the disease. Platz et al., supra at 19, 28-29, 32-34. Aside from these generalities, a deeper understanding of the genetic basis of prostate cancer has remained elusive. Considerable research has been directed to studying the link between prostate cancer, androgens, and androgen regulation, as androgens play a crucial role in prostate growth and differentiation. Meena Augustus et al., *Molecular Genetics and Markers of Progression, in Management of Prostate Cancer* 59 (Eric A Klein ed. 2000). While a number of studies have concluded that prostate tumor development is linked to elevated levels of circulating androgen (e.g., testosterone and dihydrotestosterone), the genetic determinants of these levels remain unknown. Platz et al., supra at 29-30.

Several studies have explored a possible link between prostate cancer and the androgen receptor (AR) gene, the gene product of which mediates the molecular and cellular effects of testosterone and dihydrotestosterone in tissues responsive to androgens. Id. at 30. Differences in the number of certain trinucleotide repeats in exon 1, the region involved in transactivational control, have been of particular interest. Augustus et al., supra at 60. For example, these studies have revealed that as the number of CAG repeats decreases the transactivation ability of the gene product increases, as does the risk of prostate cancer. Platz et al., supra at 30-31. Other research has focused on the α-reductase Type 2 gene, the gene which codes for the enzyme that converts testosterone into dihydrotestosterone. Id. at 30. Dihydrotestosterone has greater affinity for the AR than testosterone, resulting in increased transactivation of genes responsive to androgens. Id. While studies have reported differences among the races in the length of a TA dinucleotide repeat in the 3' untranslated region, no link has been established between the length of that repeat and prostate cancer. Id. Interestingly, while ras gene mutations are implicated in numerous other cancers, such mutations appear not to play a significant role in prostate cancer, at least among Caucasian males. Augustus, supra at 52.

Environmental/dietary risk factors which may increase the risk of prostate cancer include intake of saturated fat and calcium. Platz et al., supra at 19, 25-26. Conversely, intake of selenium, vitamin E and tomato products (which contain the carotenoid lycopene) apparently decrease that risk. Id. at 19, 26-28 The impact of physical activity, cigarette smoking, and alcohol consumption on prostate cancer is unclear. Platz et al., supra at 23-25.

Periodic screening for prostate cancer is most effectively performed by digital rectal examination (DRE) of the prostate, in conjunction with determination of the serum level of prostate-specific antigen (PSA). Burdette, supra at 148. While the merits of such screening are the subject of considerable debate, Jerome P. Richie & Irving D. Kaplan, *Screening for Prostate Cancer: The Horns of a Dilemma, in Prostate Cancer: A Multidisciplinary Guide* 1-10 (Philip W. Kantoff et al. eds. 1997), the American Cancer Society and American Urological Association recommend that both of these tests be performed annually on men 50 years or older with a life expectancy of at least 10 years, and younger men at high risk for prostate cancer. Ian M. Thompson & John Foley, *Screening for Prostate Cancer, in Management of Prostate Cancer* 71 (Eric A Klein ed. 2000). If necessary, these screening methods may be followed by additional tests, including biopsy, ultrasonic imaging, computerized tomography, and magnetic resonance imaging. Christopher A. Haas & Martin I. Resnick, *Trends in Diagnosis, Biopsy, and Imaging, in Management of Prostate Cancer* 89-98 (Eric A Klein ed. 2000); Burdette, supra at 148.

Once the diagnosis of prostate cancer has been made, treatment decisions for the individual are typically linked to the stage of prostate cancer present in that individual, as well as his age and overall health. Burdette, supra at 151. One preferred classification system for staging prostate cancer was developed by the American Urological Association (AUA). Id. at 148. The AUA classification system divides prostate tumors into four broad stages, A to D, which are in turn accompanied by a number of smaller substages. Burdette, supra at 152-153; Anthony V. D'Amico et al., *The Staging of Prostate Cancer*, in *Prostate Cancer: A Multidisciplinary Guide* 41 (Philip W. Kantoff et al. eds. 1997).

Stage A prostate cancer refers to the presence of microscopic cancer within the prostate gland. D'Amico, supra at 41. This stage is comprised of two substages: A1, which involves less than four well-differentiated cancer foci within the prostate, and A2, which involves greater than three well-differentiated cancer foci or alternatively, moderately to poorly differentiated foci within the prostate. Burdette, supra at 152; D'Amico, supra at 41. Treatment for stage A1 preferentially involves following PSA levels and periodic DRE. Burdette, supra at 151. Should PSA levels rise, preferred treatments include radical prostatectomy in patients 70 years of age and younger, external beam radiotherapy for patients between 70 and 80 years of age, and hormone therapy for those over 80 years of age. Id.

Stage B prostate cancer is characterized by the presence of a palpable lump within the prostate. Burdette, supra at 152-53; D'Amico, supra at 41. This stage is comprised of three substages: B1, in which the lump is less than 2 cm and is contained in one lobe of the prostate; B2, in which the lump is greater than 2 cm yet is still contained within one lobe; and B3, in which the lump has spread to both lobes. Burdette, supra, at 152-53. For stages B1 and B2, the treatment again involves radical prostatectomy in patients 70 years of age and younger, external beam radiotherapy for patients between 70 and 80 years of age, and hormone therapy for those over 80 years of age. Id. at 151. In stage B3, radical prostatectomy is employed if the cancer is well-differentiated and PSA levels are below 15 ng/mL; otherwise, external beam radiation is the chosen treatment option. Id.

Stage C prostate cancer involves a substantial cancer mass accompanied by extraprostatic extension. Burdette, supra at 153; D'Amico, supra at 41. Like stage A prostate cancer, Stage C is comprised of two substages: substage C1, in which the tumor is relatively minimal, with minor prostatic extension, and substage C2, in which the tumor is large and bulky, with major prostatic extension. Id. The treatment of choice for both substages is external beam radiation. Burdette, supra at 151.

The fourth and final stage of prostate cancer, Stage D, describes the extent to which the cancer has metastasized. Burdette, supra at 153; D'Amico, supra at 41. This stage is comprised of four substages: (1) D0, in which acid phophatase levels are persistently high, (2) D1, in which only the pelvic lymph nodes have been invaded, (3) D2, in which the lymph nodes above the aortic bifurcation have been invaded, with or without distant metastasis, and (4) D3, in which the metastasis progresses despite intense hormonal therapy. Id. Treatment at this stage may involve hormonal therapy, chemotherapy, and removal of one or both testes. Burdette, supra at 151.

Despite the need for accurate staging of prostate cancer, current staging methodology is limited. The wide variety of biological behavior displayed by neoplasms of the prostate has resulted in considerable difficulty in predicting and assessing the course of prostate cancer. Augustus et al., supra at 47. Indeed, despite the fact that most prostate cancer patients have carcinomas that are of intermediate grade and stage, prognosis for these types of carcinomas is highly variable. Andrew A Renshaw & Christopher L. Corless, *Prognostic Features in the Pathology of Prostate Cancer*, in *Prostate Cancer: A Multidisciplinary Guide* 26 (Philip W. Kantoff et al. eds. 1997). Techniques such as transrectal ultrasound, abdominal and pelvic computerized tomography, and MRI have not been particularly useful in predicting local tumor extension. D'Amico, supra at 53 (editors' comment). While the use of serum PSA in combination with the Gleason score is currently the most effective method of staging prostate cancer, id., PSA is of limited predictive value, Augustus et al., supra at 47; Renshaw et al., supra at 26, and the Gleason score is prone to variability and error, King, C. R. & Long, J. P., *Int'l. J. Cancer* 90(6): 326-30 (2000). As such, the current focus of prostate cancer research has been to obtain biomarkers to help better assess the progression of the disease. Augustus et al., supra at 47; Renshaw et al., supra at 26; Pettaway, C. A., *Tech. Urol.* 4(1): 35-42 (1998).

Accordingly, there is a great need for more sensitive and accurate methods for predicting whether a person is likely to develop prostate cancer, for diagnosing prostate cancer, for monitoring the progression of the disease, for staging the prostate cancer, for determining whether the prostate cancer has metastasized and for imaging the prostate cancer. There is also a need for better treatment of prostate cancer.

Ovarian Cancer

Cancer of the ovaries is the fourth-most common cause of cancer death in women in the United States, with more than 23,000 new cases and roughly 14,000 deaths predicted for the year 2001. Shridhar, V. et al., *Cancer Res.* 61(15): 5895-904 (2001); Memarzadeh, S. & Berek, J. S., *J. Reprod. Med.* 46(7): 621-29 (2001). The American Cancer Society estimates that there will be about 25,580 new cases of ovarian cancer in 2004 in the United States alone. Ovarian cancer will cause about 16,090 deaths in the United States in the same year. ACS Website: cancer.org of the world wide web. The incidence of ovarian cancer is of serious concern worldwide, with an estimated 191,000 new cases predicted annually. Runnebaum, I. B. & Stickeler, E., *J. Cancer Res. Clin. Oncol.* 127(2): 73-79 (2001). Unfortunately, women with ovarian cancer are typically asymptomatic until the disease has metastasized. Because effective screening for ovarian cancer is not available, roughly 70% of women diagnosed have an advanced stage of the cancer with a five-year survival rate of ~25-30%. Memarzadeh, S. & Berek, J. S., supra; Nunns, D. et al., *Obstet. Gynecol. Surv.* 55(12): 746-51. Conversely, women diagnosed with early stage ovarian cancer enjoy considerably higher survival rates. Werness, B. A. & Eltabbakh, G. H., *Int'l. J. Gynecol. Pathol.* 20(1): 48-63 (2001). Although our understanding of the etiology of ovarian cancer is incomplete, the results of extensive research in this area point to a combination of age, genetics, reproductive, and dietary/environmental factors. Age is a key risk factor in the development of ovarian cancer: while the risk for developing ovarian cancer before the age of 30 is slim, the incidence of ovarian cancer rises linearly between ages 30 to 50, increasing at a slower rate thereafter, with the highest incidence being among septagenarian women. Jeanne M. Schilder et al., *Hereditary Ovarian Cancer. Clinical Syndromes and Management*, in *Ovarian Cancer* 182 (Stephen C. Rubin & Gregory P. Sutton eds., 2d ed. 2001).

With respect to genetic factors, a family history of ovarian cancer is the most significant risk factor in the development of the disease, with that risk depending on the number of affected family members, the degree of their relationship to the woman, and which particular first degree relatives are affected by the disease. Id. Mutations in several genes have been associated with ovarian cancer, including BRCA1 and BRCA2, both of which play a key role in the development of breast cancer, as well as hMSH2 and hMLH1, both of which are associated with hereditary non-polyposis colon cancer. Katherine Y. Look, *Epidemiology, Etiology, and Screening of Ovarian Cancer*, in *Ovarian Cancer* 169, 171-73 (Stephen C. Rubin & Gregory P. Sutton eds., 2d ed. 2001). BRCA1, located on chromosome 17, and BRCA2, located on chromosome 13, are tumor suppressor genes implicated in DNA repair; mutations in these genes are linked to roughly 10% of ovarian cancers. Id. at 171-72; Schilder et al., supra at 185-86. hMSH2 and hMLH1 are associated with DNA mismatch repair, and are located on chromosomes 2 and 3, respectively; it has been reported that roughly 3% of hereditary ovarian carcinomas are due to mutations in these genes. Look, supra at 173; Schilder et al., supra at 184, 188-89.

Reproductive factors have also been associated with an increased or reduced risk of ovarian cancer. Late menopause, nulliparity, and early age at menarche have all been linked with an elevated risk of ovarian cancer. Schilder et al., supra at 182. One theory hypothesizes that these factors increase the number of ovulatory cycles over the course of a woman's life, leading to "incessant ovulation," which is thought to be the primary cause of mutations to the ovarian epithelium. Id.; Laura J. Havrilesky & Andrew Berchuck, *Molecular Alterations in Sporadic Ovarian Cancer*, in Ovarian Cancer 25 (Stephen C. Rubin & Gregory P. Sutton eds., 2d ed. 2001). The mutations may be explained by the fact that ovulation results in the destruction and repair of that epithelium, necessitating increased cell division, thereby increasing the possibility that an undetected mutation will occur. Id. Support for this theory may be found in the fact pregnancy, lactation, and the use of oral contraceptives, all of which suppress ovulation, confer a protective effect with respect to developing ovarian cancer. Id.

Among dietary/environmental factors, there would appear to be an association between high intake of animal fat or red meat and ovarian cancer, while the antioxidant Vitamin A, which prevents free radical formation and also assists in maintaining normal cellular differentiation, may offer a protective effect. Look, supra at 169. Reports have also associated asbestos and hydrous magnesium trisilicate (talc), the latter of which may be present in diaphragms and sanitary napkins. Id. at 169-70.

Current screening procedures for ovarian cancer, while of some utility, are quite limited in their diagnostic ability, a problem that is particularly acute at early stages of cancer progression when the disease is typically asymptomatic yet is most readily treated. Walter J. Burdette, *Cancer: Etiology, Diagnosis, and Treatment* 166 (1998); Memarzadeh & Berek, supra; Runnebaum & Stickeler, supra; Werness & Eltabbakh, supra. Commonly used screening tests include biannual rectovaginal pelvic examination, radioimmunoassay to detect the CA-125 serum tumor marker, and transvaginal ultrasonography. Burdette, supra at 166.

Pelvic examination has failed to yield adequate numbers of early diagnoses, and the other methods are not sufficiently accurate. Id. One study reported that only 15% of patients who suffered from ovarian cancer were diagnosed with the disease at the time of their pelvic examination. Look, supra at 174. Moreover, the CA-125 test is prone to giving false positives in pre-menopausal women and has been reported to be of low predictive value in post-menopausal women. Id. at 174-75. Although transvaginal ultrasonography is now the preferred procedure for screening for ovarian cancer, it is unable to distinguish reliably between benign and malignant tumors, and also cannot locate primary peritoneal malignancies or ovarian cancer if the ovary size is normal. Schilder et al., supra at 194-95. While genetic testing for mutations of the BRCA1, BRCA2, hMSH2, and hMLH1 genes is now available, these tests may be too costly for some patients and may also yield false negative or indeterminate results. Schilder et al., supra at 191-94.

Other markers of interest are HE4 and mesothelin, see Urban et al. Ovarian cancer screening Hematol Oncol Clin North Am. 2003 August; 17(4):989-1005; Hellstrom et al. The HE4 (WFDC2) protein is a biomarker for ovarian carcinoma, Cancer Res. 2003 Jul. 1; 63(13):3695-700; Ordonez, Application of mesothelin immunostaining in tumor diagnosis, Am J Surg Pathol. 2003 November; 27(11):1418-28.

The staging of ovarian cancer, which is accomplished through surgical exploration, is crucial in determining the course of treatment and management of the disease. *AJCC Cancer Staging Handbook* 187 (Irvin D. Fleming et al. eds., 5th ed. 1998); Burdette, supra at 170; Memarzadeh & Berek, supra; Shridhar et al., supra. Staging is performed by reference to the classification system developed by the International Federation of Gynecology and Obstetrics. David H. Moore, *Primary Surgical Management of Early Epithelial Ovarian Carcinoma*, in Ovarian Cancer 203 (Stephen C. Rubin & Gregory P. Sutton eds., 2d ed. 2001); Fleming et al. eds., supra at 188. Stage I ovarian cancer is characterized by tumor growth that is limited to the ovaries and is comprised of three substages. Id. In substage IA, tumor growth is limited to one ovary, there is no tumor on the external surface of the ovary, the ovarian capsule is intact, and no malignant cells are present in ascites or peritoneal washings. Id. Substage IB is identical to A1, except that tumor growth is limited to both ovaries. Id. Substage IC refers to the presence of tumor growth limited to one or both ovaries, and also includes one or more of the following characteristics: capsule rupture, tumor growth on the surface of one or both ovaries, and malignant cells present in ascites or peritoneal washings. Id.

Stage II ovarian cancer refers to tumor growth involving one or both ovaries, along with pelvic extension. Id. Substage IIA involves extension and/or implants on the uterus and/or fallopian tubes, with no malignant cells in the ascites or peritoneal washings, while substage IIB involves extension into other pelvic organs and tissues, again with no malignant cells in the ascites or peritoneal washings. Id. Substage IIC involves pelvic extension as in IIA or IIB, but with malignant cells in the ascites or peritoneal washings. Id.

Stage III ovarian cancer involves tumor growth in one or both ovaries, with peritoneal metastasis beyond the pelvis confirmed by microscope and/or metastasis in the regional lymph nodes. Id. Substage IIIA is characterized by microscopic peritoneal metastasis outside the pelvis, with substage IIIB involving macroscopic peritoneal metastasis outside the pelvis 2 cm or less in greatest dimension. Id. Substage IIIC is identical to IIIB, except that the metastasis is greater than 2 cm in greatest dimension and may include regional lymph node metastasis. Id. Lastly, Stage IV refers to the presence distant metastasis, excluding peritoneal metastasis. Id.

While surgical staging is currently the benchmark for assessing the management and treatment of ovarian cancer, it suffers from considerable drawbacks, including the invasiveness of the procedure, the potential for complications, as well as the potential for inaccuracy. Moore, supra at 206-208, 213. In view of these limitations, attention has turned to developing alternative staging methodologies through understanding differential gene expression in various stages of ovarian cancer and by obtaining various biomarkers to help better assess the progression of the disease. Vartiainen, J. et al., *Int'l J. Cancer*, 95(5): 313-16 (2001); Shridhar et al. supra; Baekelandt, M. et al., *J. Clin. Oncol*. 18(22): 3775-81.

The treatment of ovarian cancer typically involves a multiprong attack, with surgical intervention serving as the foundation of treatment. Dennis S. Chi & William J. Hoskins, *Primary Surgical Management of Advanced Epithelial Ovarian Cancer*, in Ovarian Cancer 241 (Stephen C. Rubin &

Gregory P. Sutton eds., 2d ed. 2001). For example, in the case of epithelial ovarian cancer, which accounts for ~90% of cases of ovarian cancer, treatment typically consists of: (1) cytoreductive surgery, including total abdominal hysterectomy, bilateral salpingo-oophorectomy, omentectomy, and lymphadenectomy, followed by (2) adjuvant chemotherapy with paclitaxel and either cisplatin or carboplatin. Eltabbakh, G. H. & Awtrey, C. S., *Expert Op. Pharmacother.* 2(10): 109-24. Despite a clinical response rate of 80% to the adjuvant therapy, most patients experience tumor recurrence within three years of treatment. Id. Certain patients may undergo a second cytoreductive surgery and/or second-line chemotherapy. Memarzadeh & Berek, supra.

From the foregoing, it is clear that procedures used for detecting, diagnosing, monitoring, staging, prognosticating, and preventing the recurrence of ovarian cancer are of critical importance to the outcome of the patient. Moreover, current procedures, while helpful in each of these analyses, are limited by their specificity, sensitivity, invasiveness, and/or their cost. As such, highly specific and sensitive procedures that would operate by way of detecting novel markers in cells, tissues, or bodily fluids, with minimal invasiveness and at a reasonable cost, would be highly desirable.

Accordingly, there is a great need for more sensitive and accurate methods for predicting whether a person is likely to develop ovarian cancer, for diagnosing ovarian cancer, for monitoring the progression of the disease, for staging the ovarian cancer, for determining whether the ovarian cancer has metastasized, for imaging the ovarian cancer and for better treatment of ovarian cancer.

Colon Cancer

Colorectal cancer is the second most common cause of cancer death in the United States and the third most prevalent cancer in both men and women. M. L. Davila & A. D. Davila, *Screening for Colon and Rectal Cancer, in Colon and Rectal Cancer* 47 (Peter S. Edelstein ed., 2000). The American Cancer Society estimates that there will be about 106,370 new cases of colon cancer and 40,570 new cases of rectal cancer in the 2004 in the United States alone. Colon cancer and rectal cancer will cause about 56,730 deaths combined in the United States. ACS Website: cancer.org of the world wide web. Nearly all cases of colorectal cancer arise from adenomatous polyps, some of which mature into large polyps, undergo abnormal growth and development, and ultimately progress into cancer. Davila at 55-56. This progression would appear to take at least 10 years in most patients, rendering it a readily treatable form of cancer if diagnosed early, when the cancer is localized. Davila at 56; Walter J. Burdette, *Cancer: Etiology Diagnosis and Treatment* 125 (1998).

Although our understanding of the etiology of colon cancer is undergoing continual refinement, extensive research in this area points to a combination of factors, including age, hereditary and nonhereditary conditions, and environmental/dietary factors. Age is a key risk factor in the development of colorectal cancer, Davila at 48, with men and women over 40 years of age become increasingly susceptible to that cancer, Burdette at 126. Incidence rates increase considerably in each subsequent decade of life. Davila at 48. A number of hereditary and nonhereditary conditions have also been linked to a heightened risk of developing colorectal cancer, including familial adenomatous polyposis (FAP), hereditary nonpolyposis colorectal cancer (Lynch syndrome or HNPCC), a personal and/or family history of colorectal cancer or adenomatous polyps, inflammatory bowel disease, diabetes mellitus, and obesity. Id. at 47; Henry T. Lynch & Jane F. Lynch, *Hereditary Nonpolyposis Colorectal Cancer (Lynch Syndromes), in Colon and Rectal Cancer* 67-68 (Peter S. Edelstein ed., 2000).

Environmental/dietary factors associated with an increased risk of colorectal cancer include a high fat diet, intake of high dietary red meat, and sedentary lifestyle. Davila at 47; Reddy, B. S., *Prev. Med.* 16(4): 460-7 (1987). Conversely, environmental/dietary factors associated with a reduced risk of colorectal cancer include a diet high in fiber, folic acid, calcium, and hormone-replacement therapy in post-menopausal women. Davila at 50-55. The effect of antioxidants in reducing the risk of colon cancer is unclear. Davila at 53.

Because colon cancer is highly treatable when detected at an early, localized stage, screening should be a part of routine care for all adults starting at age 50, especially those with first-degree relatives with colorectal cancer. One major advantage of colorectal cancer screening over its counterparts in other types of cancer is its ability to not only detect precancerous lesions, but to remove them as well. Davila at 56. The key colorectal cancer screening tests in use today are fecal occult blood test, sigmoidoscopy, colonoscopy, double-contrast barium enema, and the carcinoembryonic antigen (CEA) test. Burdette at 125; Davila at 56.

The fecal occult blood test (FOBT) screens for colorectal cancer by detecting the amount of blood in the stool, the premise being that neoplastic tissue, particularly malignant tissue, bleeds more than typical mucosa, with the amount of bleeding increasing with polyp size and cancer stage. Davila at 56-57. While effective at detecting early stage tumors, FOBT is unable to detect adenomatous polyps (premalignant lesions), and, depending on the contents of the fecal sample, is subject to rendering false positives. Davila at 56-59. Sigmoidoscopy and colonoscopy, by contrast, allow direct visualization of the bowel, and enable one to detect, biopsy, and remove adenomatous polyps. Davila at 59-60, 61. Despite the advantages of these procedures, there are accompanying downsides: sigmoidoscopy, by definition, is limited to the sigmoid colon and below, colonoscopy is a relatively expensive procedure, and both share the risk of possible bowel perforation and hemorrhaging. Davila at 59-60. Double-contrast barium enema (DCBE) enables detection of lesions better than FOBT, and almost as well a colonoscopy, but it may be limited in evaluating the winding rectosigmoid region. Davila at 60. The CEA blood test, which involves screening the blood for carcinoembryonic antigen, shares the downside of FOBT, in that it is of limited utility in detecting colorectal cancer at an early stage. Burdette at 125.

Once colon cancer has been diagnosed, treatment decisions are typically made in reference to the stage of cancer progression. A number of techniques are employed to stage the cancer (some of which are also used to screen for colon cancer), including pathologic examination of resected colon, sigmoidoscopy, colonoscopy, and various imaging techniques. *AJCC Cancer Staging Handbook* 84 (Irvin D. Fleming et al. eds., 5$^{th}$ ed. 1998); Montgomery, R. C. and Ridge, J. A., *Semin. Surg. Oncol.* 15(3): 143-150 (1998). Moreover, chest films, liver functionality tests, and liver scans are employed to determine the extent of metastasis. Fleming at 84. While computerized tomography and magnetic resonance imaging are useful in staging colorectal cancer in its later stages, both have unacceptably low staging accuracy for identifying early stages of the disease, due to the difficulty that both methods have in (1) revealing the depth of bowel wall tumor infiltration and (2) diagnosing malignant adenopathy. Thoeni, R. F., *Radiol. Clin. N. Am.* 35(2): 457-85 (1997). Rather, techniques such as transrectal ultrasound (TRUS) are preferred in this context, although this technique is inaccurate with respect to detecting small lymph nodes that may contain metastases. David Blumberg & Frank G. Opelka, *Neoadjuvant and Adjuvant Therapy for Adenocarcinoma of the Rectum, in Colon and Rectal Cancer* 316 (Peter S. Edelstein ed., 2000).

Several classification systems have been devised to stage the extent of colorectal cancer, including the Dukes' system and the more detailed International Union against Cancer-American Joint Committee on Cancer TNM staging system, which is considered by many in the field to be a more useful staging system. Burdette at 126-27. The TNM system, which is used for either clinical or pathological staging, is divided into four stages, each of which evaluates the extent of cancer growth with respect to primary tumor (T), regional lymph nodes (N), and distant metastasis (M). Fleming at 84-85. The system focuses on the extent of tumor invasion into the intestinal wall, invasion of adjacent structures, the number of regional lymph nodes that have been affected, and whether distant metastasis has occurred. Fleming at 81.

Stage 0 is characterized by in situ carcinoma (Tis), in which the cancer cells are located inside the glandular basement membrane (intraepithelial) or lamina propria (intramucosal). In this stage, the cancer has not spread to the regional lymph nodes (N0), and there is no distant metastasis (M0). In stage I, there is still no spread of the cancer to the regional lymph nodes and no distant metastasis, but the tumor has invaded the submucosa (T1) or has progressed further to invade the muscularis propria (T2). Stage II also involves no spread of the cancer to the regional lymph nodes and no distant metastasis, but the tumor has invaded the subserosa, or the nonperitonealized pericolic or perirectal tissues (T3), or has progressed to invade other organs or structures, and/or has perforated the visceral peritoneum (T4). Stage III is characterized by any of the T substages, no distant metastasis, and either metastasis in 1 to 3 regional lymph nodes (N1) or metastasis in four or more regional lymph nodes (N2). Lastly, stage IV involves any of the T or N substages, as well as distant metastasis. Fleming at 84-85; Burdette at 127.

Currently, pathological staging of colon cancer is preferable over clinical staging as pathological staging provides a more accurate prognosis. Pathological staging typically involves examination of the resected colon section, along with surgical examination of the abdominal cavity. Fleming at 84. Clinical staging would be a preferred method of staging were it at least as accurate as pathological staging, as it does not depend on the invasive procedures of its counterpart.

Turning to the treatment of colorectal cancer, surgical resection results in a cure for roughly 50% of patients. Irradiation is used both preoperatively and postoperatively in treating colorectal cancer. Chemotherapeutic agents, particularly 5-fluorouracil, are also powerful weapons in treating colorectal cancer. Other agents include irinotecan and floxuridine, cisplatin, levamisole, methotrexate, interferon-α, and leucovorin. Burdette at 125, 132-33. Nonetheless, thirty to forty percent of patients will develop a recurrence of colon cancer following surgical resection, which in many patients is the ultimate cause of death. Wayne De Vos, *Follow-up After Treatment of Colon Cancer, Colon and Rectal Cancer* 225 (Peter S. Edelstein ed., 2000). Accordingly, colon cancer patients must be closely monitored to determine response to therapy and to detect persistent or recurrent disease and metastasis.

The next few paragraphs describe the some of molecular bases of colon cancer. In the case of FAP, the tumor suppressor gene APC (adenomatous polyposis coli), chromosomally located at 5q21, has been either inactivated or deleted by mutation. Alberts et al., *Molecular Biology of the Cell* 1288 (3d ed. 1994). The APC protein plays a role in a number of functions, including cell adhesion, apoptosis, and repression of the c-myc oncogene. N. R. Hall & R. D. Madoff, *Genetics and the Polyp-Cancer Sequence, Colon and Rectal Cancer* 8 (Peter S. Edelstein, ed., 2000). Of those patients with colorectal cancer who have normal APC genes, over 65% have such mutations in the cancer cells but not in other tissues. Alberts et al., supra at 1288. In the case of HPNCC, patients manifest abnormalities in the tumor suppressor gene HNPCC, but only about 15% of tumors contain the mutated gene. Id. A host of other genes have also been implicated in colorectal cancer, including the K-ras, N-ras, H-ras and C-myc oncogenes, and the tumor suppressor genes DCC (deleted in colon carcinoma) and p53. Hall & Madoff, supra at 8-9; Alberts et al., supra at 1288.

Abnormalities in Wg/Wnt signal transduction pathway are also associated with the development of colorectal carcinoma. Taipale, J. and Beachy, P. A. *Nature* 411: 349-354 (2001). Wnt1 is a secreted protein gene originally identified within mouse mammary cancers by its insertion into the mouse mammary tumor virus (MMTV) gene. The protein is homologous to the wingless (Wg) gene product of *Drosophila*, in which it functions as an important factor for the determination of dorsal-ventral segmentation and regulates the formation of fly imaginal discs. Wg/Wnt pathway controls cell proliferation, death and differentiation. Taipal (2001). There are at least 13 members in the Wnt family. These proteins have been found expressed mainly in the central nervous system (CNS) of vertebrates as well as other tissues such as mammary and intestine. The Wnt proteins are the ligands for a family of seven transmembrane domain receptors related to the Frizzled gene product in *Drosophila*. Binding Wnt to Frizzled stimulates the activity of the downstream target, Dishevelled, which in turn inactivates the glycogen synthesase kinase 3β (GSK3β). Taipal (2001). Usually active GSK3β will form a complex with the adenomatous polyposis coli (APC) protein and phosphorylate another complex member, β-catenin. Once phosphorylated, β-catenin is directed to degradation through the ubiquitin pathway. When GSK3β or APC activity is down regulated, β-catenin is accumulated in the cytoplasm and binds to the T-cell factor or lymphocyte excitation factor (Tcf/Lef) family of transcriptional factors. Binding of β-catenin to Tcf releases the transcriptional repression and induces gene transcription. Among the genes regulated by β-catenin are a transcriptional repressor Engrailed, a transforming growth factor-β (TGF-β) family member Decapentaplegic, and the cytokine Hedgehog in *Drosophila*. β-Catenin also involves in regulating cell adhesion by binding to α-catenin and E-cadherin. On the other hand, binding of β-catenin to these proteins controls the cytoplasmic β-catenin level and its complexing with TCF. Taipal (2001). Growth factor stimulation and activation of c-src or v-src also regulate β-catenin level by phosphorylation of α-catenin and its related protein, p120$^{cas}$. When phosphorylated, these proteins decrease their binding to E-cadherin and β-catenin resulting in the accumulation of cytoplasmic β-catenin. Reynolds, A. B. et al. *Mol. Cell. Biol.* 14: 8333-8342 (1994). In colon cancer, c-src enzymatic activity has been shown increased to the level of v-src. Alternation of components in the Wg/Wnt pathway promotes colorectal carcinoma development. The best known modifications are to the APC gene. Nicola S et al. *Hum. Mol. Genet.* 10:721-733 (2001). This germline mutation causes the appearance of hundreds to thousands of adenomatous polyps in the large bowel. It is the gene defect that accounts for the autosomally dominantly inherited FAP and related syndromes. The molecular alternations that occur in this pathway largely involve deletions of alleles of tumor-suppressor genes, such as APC, p53 and Deleted in Colorectal Cancer (DCC), combined with mutational activation of proto-oncogenes, especially c-Ki-ras. Aoki, T. et al. *Human Mutat.* 3: 342-346 (1994). All of these lead to genomic instability in colorectal cancers.

Another source of genomic instability in colorectal cancer is the defect of DNA mismatch repair (MMR) genes. Human homologues of the bacterial mutHLS complex (hMSH2, hMLH1, hPMS1, hPMS2 and hMSH6), which is involved in the DNA mismatch repair in bacteria, have been shown to cause the HNPCC (about 70-90% HNPCC) when mutated. Modrich, P. and Lahue, R. *Ann Rev. Biochem.* 65: 101-133 (1996); and Peltomäki, P. *Hum. Mol. Genet.* 10: 735-740 (2001). The inactivation of these proteins leads to the accumulation of mutations and causes genetic instability that represents errors in the accurate replication of the repetitive mono-, di-, tri- and tetra-nucleotide repeats, which are scattered throughout the genome (microsatellite regions). Jass, J. R. et al. *J Gastroenterol Hepatol* 17: 17-26 (2002). Like in the classic FAP, mutational activation of c-Ki-ras is also required for the promotion of MSI in the alternative HNPCC. Mutations in other proteins such as the tumor suppressor protein phosphatase PTEN (Zhou, X. P. et al. *Hum. Mol. Genet.* 11: 445-450 (2002)), BAX (Buttler, L. M. *Aus. N. Z. J. Surg.* 69: 88-94 (1999)), Caspase-5 (Planck, M. *Cancer Genet Cytogenet.* 134: 46-54 (2002)), TGFβ-RII (Fallik, D. et al. *Gastroenterol Clin Biol.* 24: 917-22 (2000)) and IGFII-R (Giovannucci E. *J. Nutr.* 131: 3109S-20S (2001)) have also been found in some colorectal tumors possibly as the cause of MMR defect.

Some tyrosine kinases have been shown up-regulated in colorectal tumor tissues or cell lines like HT29. Skoudy, A. et al. *Biochem J.* 317 (Pt 1): 279-84 (1996). Focal adhesion kinase (FAK) and its up-stream kinase c-src and c-yes in colonic epithelia cells may play an important role in the promotion of colorectal cancers through the extracellular matrix (ECM) and integrin-mediated signaling pathways. Jessup, J. M. et al., *The molecular biology of colorectal carcinoma, in: The Molecular Basis of Human Cancer,* 251-268 (Coleman W. B. and Tsongalis G. J. Eds. 2002). The formation of c-src/FAK complexes may coordinately deregulate VEGF expression and apoptosis inhibition. Recent evidences suggest that a specific signal-transduction pathway for cell survival that implicates integrin engagement leads to FAK activation and thus activates PI-3 kinase and akt. In turn, akt phosphorylates BAD and blocks apoptosis in epithelial cells. The activation of c-src in colon cancer may induce VEGF expression through the hypoxia pathway. Other genes that may be implicated in colorectal cancer include Cox enzymes (Ota, S. et al. *Aliment Pharmacol. Ther.* 16 (Suppl 2): 102-106 (2002)), estrogen (al-Azzawi, F. and Wahab, M. *Climacteric* 5: 3-14 (2002)), peroxisome proliferator-activated receptor-γ (PPAR-γ) (Gelman, L. et al. *Cell Mol. Life. Sci.* 55: 932-943 (1999)), IGF-I (Giovannucci (2001)), thymine DNA glycosylase (TDG) (Hardeland, U. et al. *Prog. Nucleic Acid Res. Mol. Biol.* 68: 235-253 (2001)) and EGF (Mendelsohn, *J. Endocrine-Related Cancer* 8: 3-9 (2001)).

Gene deletion and mutation are not the only causes for development of colorectal cancers. Epigenetic silencing by DNA methylation also accounts for the lost of function of colorectal cancer suppressor genes. A strong association between MSI and CpG island methylation has been well characterized in sporadic colorectal cancers with high MSI but not in those of hereditary origin. In one experiment, DNA methylation of MLH1, CDKN2A, MGMT, THBS1, RARB, APC, and p14ARF genes has been shown in 80%, 55%, 23%, 23%, 58%, 35%, and 50% of 40 sporadic colorectal cancers with high MSI respectively. Yamamoto, H. et al. *Genes Chromosomes Cancer* 33: 322-325 (2002); and Kim, K. M. et al. *Oncogene.* 12; 21(35): 5441-9 (2002). Carcinogen metabolism enzymes such as GST, NAT, CYP and MTHFR are also associated with an increased or decreased colorectal cancer risk. Pistorius, S. et al. *Kongressbd Dtsch Ges Chir Kongr* 118: 820-824 (2001); and Potter, J. D. *J. Natl. Cancer Inst.* 91: 916-932 (1999).

From the foregoing, it is clear that procedures used for detecting, diagnosing, monitoring, staging, prognosticating, and preventing the recurrence of colorectal cancer are of critical importance to the outcome of the patient. Moreover, current procedures, while helpful in each of these analyses, are limited by their specificity, sensitivity, invasiveness, and/or their cost. As such, highly specific and sensitive procedures that would operate by way of detecting novel markers in cells, tissues, or bodily fluids, with minimal invasiveness and at a reasonable cost, would be highly desirable.

Accordingly, there is a great need for more sensitive and accurate methods for predicting whether a person is likely to develop colorectal cancer, for diagnosing colorectal cancer, for monitoring the progression of the disease, for staging the colorectal cancer, for determining whether the colorectal cancer has metastasized, and for imaging the colorectal cancer. Following accurate diagnosis, there is also a need for less invasive and more effective treatment of colorectal cancer.

Gastric Cancer

The American Cancer Society estimates that there will be about 22,710 new cases of stomach cancer in 2004 in the United States alone. Stomach cancer will cause about 11,780 deaths in the United States. ACS Website: cancer.org of the world wide web. As recent as 2001 gastric cancer was estimated to rank as the thirteenth most common and the eighth most deadly cancer in the United States. *AJCC Cancer Staging Handbook* 71 (Irvin D. Fleming et al. eds., 5th ed. 1998). Due to a dramatic decline in the United States over the last four decades, stomach cancer was estimated to account for 2.5% of deaths from cancer in the United States in 1997, with roughly 22,000 new cases and 14,000 deaths estimated for that year. Roderich E. Schwarz, *Surgical Management of Gastric Cancer: The Western Experience, in Management of Upper Gastrointestinal Cancer* 83-84 (John M. Daly et al. eds. 1999). However, stomach cancer persists in being responsible for considerable mortality rates in Asia, Europe and South America. Walter J. Burdette, *Cancer: Etiology, Diagnosis and Treatment* 91 (1998). In Japan for example, gastric cancer accounts for roughly one-half of the cancer deaths in men and one-third of those in women. Id. Overall, patients diagnosed with gastric cancer have an approximate 5-year survival rate of around 25-30%. J. Rüdiger Siewert et al., *Early Gastric Cancer, in Management of Upper Gastrointestinal Cancer* 136 (John M. Daly et al. eds. 1999).

Although our understanding of the etiology of gastric cancer is undergoing continual refinement, research in this area points to several risk factors, including various stomach diseases, diet, occupation, and genetic factors. Burdette, supra at 91. In the case of stomach diseases, stomach polyps, atrophic gastritis and metaplasia, hyperplasia related to Menetrier's disease, *Helicobacter pylori* infection, ulcers, and operations to the stomach have all been associated with an increased incidence of stomach cancer. Id. Dietary nitrate ingestion, which results in nitrosamine production in the stomach, as well as the intake of smoked meats, are also suspected as contributing factors. Id.; Fleming et al. eds., supra at 71. From an occupational standpoint, those who work in the metalworking, painting, fishing, ceramic, and printing industries all appear to have an elevated risk of acquiring stomach cancer. Burdette, supra at 91. From a genetic standpoint, gastric carcinomas are believed to occur through two genetic pathways: (1) chromosomal deletions that involve tumor suppressor genes and (2) microsatellite instability which targets the mononucleotide segments in coding regions of genes related to cancer. Rhyu, M. G., *J. Korean Med. Sci.* 13(4): 339-49 (1998). A variation in the N-acetyltransferase 1 gene has also been linked to elevated risk of gastric cancer. Boissy, R. J. et al., *Int'l J. Cancer* 87(4): 507-11 (2000).

Like many cancers, gastric cancer is more readily treatable when detected early. Patients diagnosed with early gastric cancer that follow proper treatment have survival rates that match healthy control patients of the same age. Siewert, supra at 136. Unfortunately, the symptoms and clinical manifestations of gastric cancer typically do not appear early in the course of the disease, and the majority of patients have symptoms of the disease for six months or more prior to diagnosis. Burdette, supra at 93. Accordingly, effective screening devices are crucial in diagnosing the disease early and in effecting proper treatment.

Following an initial assessment of a potential gastric cancer patient's symptoms, which may include, inter alia, indigestion, abdominal discomfort, dysphagia, nausea, anorexia, flatulence, weight loss, melena, the presence of a palpable mass, anemia, and enlarged lymph nodes, id., a physician may perform various screening tests. These tests include scanning for the presence of elevated levels of carcinoembryonic and oncofetal antigens, achlorhydria, blood in the stool, and cytologic analysis of gastric washings. Id. Unfortunately, in the case of the first three tests, positive results are not necessarily obtained when gastric cancer is present, or false positives may result due to the presence of other conditions. Id. A certain diagnosis is typically achieved by way of endoscopy and/or radiography using barium contrast medium. Id.; Schwarz, supra at 87. Ultrasonography, computed tomography (CT), and magnetic resonance imaging (MRI) are additionally useful in determining the extent of metastasis. Burdette, supra at 94.

Once gastric cancer has been diagnosed, treatment decisions are made in reference to the stage of cancer progression. Iain G. Martin, *Staging of Esophageal and Gastric Cancer, in Management of Upper Gastrointestinal Cancer* 3 (John M. Daly et al. eds. 1999). Accurate staging has become even more vital to a successful treatment regimen in view of the present trend toward multi-modal therapy for gastric cancer, and particularly neoadjuvant therapy. Id.

A number of techniques are employed to stage gastric cancer (some of which are also used to screen for gastric cancer), including endoscopic ultrasonography (EUS), CT, and MRI. Id. at 24-31. EUS is the only method of staging capable of providing accurate data regarding the tumor stage (T stage) of gastric cancer, and its overall accuracy for gathering data regarding the lymph nodal stage of gastric cancer is about 70% Id. at 27-28. EUS, however, is limited for several reasons: (1) roughly 15% of patients present with non-traversable lesions, (2) there are regions of the stomach in which it is difficult to obtain high quality images, and (3) it has difficulty in discerning particular types of cancerous lesions. Id. at 27. CT scanning is of some utility when used in combination with other techniques, but it is too inaccurate to be used alone for several reasons: (1) it is limited in its ability to assess the tumor stage due to its inability to distinguish between the individual layers of the gastric wall, (2) it is highly inaccurate in assessing lymph node metastasis, and (3) it is generally unhelpful in assessing peritoneal or liver metastasis. Id. at 24, 26-27. MRI, by contrast, is able to distinguish between muscle layers in the stomach, and one study suggests that MRI is able to assist in determining the extent of tumor and serosal invasion with considerable accuracy. Id. at 27. Nonetheless, other studies have indicated that MRI has little to offer to supplement a CT assessment. Id.

The development of staging through the techniques of molecular biology is still in its infancy, but some progress in this area has been made. For example, researchers have found that Thomsen-Friedenreich (TF) and MUC1-TF immunoreactivity characterizes a high-risk Stage I subgroup of gastric cancer patients. Baldus, S. E. et al., *Oncology* 61(2): 147-55 (2001). Elevated serum levels of interleukin-2 and tumor necrosis factor-alpha have been studied as possibly useful markers for advanced gastric cancer. Forones, N. M. et al., *Hepatogastroenterology* 48(40): 1199-201 (2001). Likewise, elevated levels of serum soluble E-cadherin may also serve as a useful prognostic marker for stomach cancer. Chan, A. O. et al., *Gut* 48(6): 808-11 (2001).

The two major classification systems for staging gastric cancer are the Union Internationale Contre le Cancer's TNM system, and the system devised by the Japanese Research Society for Gastric Cancer. Id. at 18-23. The TNM system is a rather simple, and in some cases arbitrary system, which is divided into several stages, each of which evaluates the extent of cancer growth with respect to primary tumor (T), regional lymph nodes (N), and distant metastasis (M). Id. at 18, 20, 22; Fleming et al. eds., supra at 3. The Japanese system is considerably more detailed, but in some cases may be overly complex and time consuming. Martin, supra at 18-20, 22-23. Because most countries other than Japan have adopted the TNM system, id. at 23, that system will be discussed further here.

Stage 0 is characterized by carcinoma in situ (Tis, an intraepithelial tumor that has not invaded the lamina propria), and stage IA involves tumor invasion of the lamina propria or submucosa (T1); neither stage involves metastasis to the regional lymph nodes (N0) nor distant metastasis (M0). Fleming et al. eds., supra at 73. Stage IB is the same as stage IA except that either (1) regional lymph node metastasis has occurred in 1 to 6 lymph nodes (N1) or (2) the tumor has invaded the muscularis propria or subserosa (T2). Id. Stage II gastric cancer is a bit more complex than the previous stages, involving one of three scenarios, none of which involve distant metastasis: (1) tumor category T1 and metastasis into 7 to 15 regional lymph nodes (N2), (2) tumor category T2 and nodal category N1, or (3) tumor invasion into serosa without invasion into adjacent structures (i.e., spleen, liver, transverse colon, diaphragm, adrenal gland, kidney, pancreas, small intestine, retroperitoneum, and abdominal wall) and nodal category N0. Id. Stage IIIA likewise involves one of three possible scenarios: (1) tumor category T2 and nodal category N2, (2) tumor category T3 and nodal category N3, or (3) tumor invasion into adjacent structures (T4) and nodal category N0. Id. at 73-74. Stage IIIB, however, involves tumor category T3 and nodal category N2. Id. Neither stage IIIA nor stage IIIB involves distant metastasis. Id. Stage IV is characterized by a variety permutations of tumor and nodal categories, with or without distant metastasis. Id.

Turning to the treatment of gastric cancer, surgical resection is the "mainstay" of treating gastric carcinomas but is only an option for 50% to 60% of patients. David Kelsen, *Combined Modality Therapy, in Management of Upper Gastrointestinal Cancer* 123 (John M. Daly et al. eds. 1999). While radiotherapy is sometimes used in conjunction with resection with some effect, gastric carcinomas are typically more resistant to radiation than are other carcinomas. Burdette, supra at 97. Likewise, chemotherapy has generally been of limited utility in treating gastric carcinomas, although neoadjuvant and adjuvant chemotherapy have been used with some success. Id. at 98; Schuhmacher, C. P. et al., *Cancer* 91(5): 918-27 (2001). Pre- or postoperative adjuvant therapy is currently being studied due to the considerable risk for reoccurrence, as well as the fact that systemic metastasis is commonplace. Kelsen, supra at 123. When chemotherapy is used, combinations of chemotherapeutic agents yield better results than single agents; agents used in successful combinations include 5-fluoruracil, leucovorin, adriamycin, cisplatin, mitomycin, etoposide, and semustine. Burdette, supra at 98.

From the foregoing, it is clear that procedures used for detecting, diagnosing, monitoring, staging, prognosticating, treating and preventing the recurrence of gastric cancer are of critical importance to the outcome of the patient. Moreover, current procedures, while helpful in each of these areas, are limited by their specificity, sensitivity, invasiveness, and/or their cost. As such, highly specific and sensitive procedures that would operate by way of detecting novel markers in cells, tissues, or bodily fluids, with minimal invasiveness and at a reasonable cost, would be highly desirable.

Angiogenesis in Cancer

Growth and metastasis of solid tumors are also dependent on angiogenesis. Folkman, J., 1986, *Cancer Research*, 46, 467-473; Folkman, J., 1989, *Journal of the National Cancer Institute*, 82, 4-6. It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites such as liver, lung or bone. Weidner, N., et al., 1991, *The New England Journal of Medicine*, 324(1), 1-8.

Angiogenesis, defined as the growth or sprouting of new blood vessels from existing vessels, is a complex process that primarily occurs during embryonic development. The process is distinct from vasculogenesis, in that the new endothelial cells lining the vessel arise from proliferation of existing cells, rather than differentiating from stem cells. The process is invasive and dependent upon proteolysis of the extracellular matrix (ECM), migration of new endothelial cells, and synthesis of new matrix components. Angiogenesis occurs during embryogenic development of the circulatory system; however, in adult humans, angiogenesis only occurs as a response to a pathological condition (except during the reproductive cycle in women).

Under normal physiological conditions in adults, angiogenesis takes place only in very restricted situations such as hair growth and wounding healing. Auerbach, W. and Auerbach, R., 1994, *Pharmacol Ther.* 63(3):265-3 11; Ribatti et al., 1991, *Haematologica* 76(4):3 11-20; Risau, 1997, *Nature* 386(6626):67 1-4. Angiogenesis progresses by a stimulus which results in the formation of a migrating column of endothelial cells. Proteolytic activity is focused at the advancing tip of this "vascular sprout", which breaks down the ECM sufficiently to permit the column of cells to infiltrate and migrate. Behind the advancing front, the endothelial cells differentiate and begin to adhere to each other, thus forming a new basement membrane. The cells then cease proliferation and finally define a lumen for the new arteriole or capillary.

Unregulated angiogenesis has gradually been recognized to be responsible for a wide range of disorders, including, but not limited to, cancer, cardiovascular disease, rheumatoid arthritis, psoriasis and diabetic retinopathy. Folkman, 1995, *Nat Med* 1(1):27-31; Isner, 1999, *Circulation* 99(13): 1653-5; Koch, 1998, *Arthritis Rheum* 41(6):951-62; Walsh, 1999, *Rheumatology* (Oxford) 38(2):103-12; Ware and Simons, 1997, *Nat Med* 3(2): 158-64.

Of particular interest is the observation that angiogenesis is required by solid tumors for their growth and metastases. Folkman, 1986 supra; Folkman 1990, *J Natl. Cancer Inst.*, 82(1) 4-6; Folkman, 1992, *Semin Cancer Biol* 3(2):65-71; Zetter, 1998, *Annu Rev Med* 49:407-24. A tumor usually begins as a single aberrant cell which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. The precise mechanisms that control the angiogenic switch is not well understood, but it is believed that neovascularization of tumor mass results from the net balance of a multitude of angiogenesis stimulators and inhibitors Folkman, 1995, supra.

One of the most potent angiogenesis inhibitors is endostatin identified by O'Reilly and Folkman. O'Reilly et al., 1997, *Cell* 88(2):277-85; O'Reilly et al., 1994, *Cell* 79(2):3 15-28. Its discovery was based on the phenomenon that certain primary tumors can inhibit the growth of distant metastases. O'Reilly and Folkman hypothesized that a primary tumor initiates angiogenesis by generating angiogenic stimulators in excess of inhibitors. However, angiogenic inhibitors, by virtue of their longer half life in the circulation, reach the site of a secondary tumor in excess of the stimulators. The net result is the growth of primary tumor and inhibition of secondary tumor. Endostatin is one of a growing list of such angiogenesis inhibitors produced by primary tumors. It is a proteolytic fragment of a larger protein: endostatin is a 20 kDa fragment of collagen XVIII (amino acid H1132-K1315 in murine collagen XVIII). Endostatin has been shown to specifically inhibit endothelial cell proliferation in vitro and block angiogenesis in vivo. More importantly, administration of endostatin to tumor-bearing mice leads to significant tumor regression, and no toxicity or drug resistance has been observed even after multiple treatment cycles. Boehm et al., 1997, Nature 390(6658):404-407. The fact that endostatin targets genetically stable endothelial cells and inhibits a variety of solid tumors makes it a very attractive candidate for anticancer therapy. Fidler and Ellis, 1994, Cell 79(2):185-8; Gastl et al., 1997, Oncology 54(3):177-84; Hinsbergh et al., 1999, Ann Oncol 10 Suppl 4:60-3. In addition, angiogenesis inhibitors have been shown to be more effective when combined with radiation and chemotherapeutic agents. Klement, 2000, J. Clin Invest, 105(8) R15-24. Browder, 2000, Cancer Res. 6-(7) 1878-86, Arap et al., 1998, Science 279(5349): 377-80; Mauceri et al., 1998, Nature 394(6690):287-91.

The present invention provides alternative methods of assessing risk of, detecting or treating prostate, ovarian, colon, breast and stomach cancer that overcome the limitations of conventional therapeutic methods as well as offer additional advantages that will be apparent from the detailed description below.

SUMMARY OF THE INVENTION

This invention is directed to a method for assessing risk of prostate cancer in a subject which comprises measuring levels of both Pro108 and Prostate Specific Antigen (PSA) in the subject, analyzing a risk associated with the level of PSA and a risk associated with the level of Pro108, and using the combined risks to assess the risk of prostate cancer in the subject. In one aspect of the invention the measuring of PSA and Pro108 levels are done simultaneously. In another aspect of the invention the measuring of PSA and Pro108 are done sequentially. In addition, the invention is directed to specific antibody pairs directed to Pro108 for detection of prostate, ovarian, colon, breast or stomach cancer. Preferably, the antibodies are used alone or in combination to detect prostate, ovarian, colon, breast or stomach cancer.

In yet another aspect of the invention, the respective levels of PSA and Pro108 are based on dividing a subject population dataset into borderline levels of PSA and elevated levels of Pro108 and a subject having both borderline PSA and high Pro108 levels is indicative of heightened risk of prostate cancer. The borderline levels of PSA may be between about 2 ng/mL and about 10 ng/mL. The borderline levels of PSA may also between about 4 ng/mL and about 10 ng/mL or between about 2 ng/mL and about 4 ng/mL.

The invention is also directed to a method for treating a subject with elevated risk of a prostate cancer, comprising: selecting a subject who has borderline levels of Prostate Specific Antigen (PSA) and elevated levels of Pro108 and treating the subject with a therapy selected from the group consisting of surgery, radiation therapy, hormone therapy or chemotherapy so as to alleviate the elevated risk of prostate cancer in the subject.

This invention is further directed to an isolated Pro108 antibody that binds to Pro108 on a mammalian cell in vivo. The invention is further directed to an isolated Pro108 antibody that internalizes upon binding to Pro108 on a mammalian cell in vivo. The antibody may be a monoclonal antibody. Alternatively, the antibody is an antibody fragment or a chimeric or a humanized antibody. The monoclonal antibody may be produced by a hybridoma selected from the group of hybridomas deposited under American Type Culture Collection accession number PTA-5885 and PTA-5886.

The antibody may compete for binding to the same epitope as the epitope bound by the monoclonal antibody produced by a hybridoma selected from the group of hybridomas deposited under the American Type Culture Collection accession number PTA-5885 and PTA-5886.

The invention is also directed to conjugated antibodies. They may be conjugated to a growth inhibitory agent or a cytotoxic agent. The cytotoxic agent may be selected from the group consisting of toxins, antibiotics, radioactive isotopes and nucleolytic enzymes and toxins. Examples of toxins include, but are not limited to, auristatin, maytansin, maytansinoids, saporin, gelonin, ricin or calicheamicin.

The mammalian cell may be a cancer cell. Preferably, the anti-Pro108 monoclonal antibody that inhibits the growth of Pro108-expressing cancer cells in vivo.

The antibody may be produced in bacteria. Alternatively, the antibody may be a humanized form of an anti-Pro108 antibody produced by a hybridoma selected from the group of hybridomas having ATCC accession number PTA-5885 and PTA-5886.

Preferably, the cancer is selected from the group consisting of prostate, ovarian, colon, breast and stomach cancer. The invention is also directed to a method of producing the antibodies comprising culturing an appropriate cell and recovering the antibody from the cell culture.

The invention is also directed to compositions comprising the antibodies and a carrier. The antibody may be conjugated to a cytotoxic agent. The cytotoxic agent may be a radioactive isotope or other chemotherapeutic agent.

The invention is also directed to a method of killing an Pro108-expressing cancer cell, comprising contacting the cancer cell with the antibodies of this invention, thereby killing the cancer cell. The cancer cell may be selected from the group consisting of prostate, ovarian, colon, breast and stomach cancer cell.

The ovarian or breast cancer may be ovarian serous or mucinous adenocarcinoma or breast infiltrating ductal carcinoma or metastatic cancer. The breast cancer may be HER-2 negative breast cancer.

The invention is also directed to a method of alleviating a Pro108-expressing cancer in a mammal, comprising administering a therapeutically effective amount of the antibodies to the mammal.

This invention is further directed to a method for assessing risk of ovarian cancer in a patient which comprises measuring levels of both Pro108 and CA125 in the patient, analyzing a risk associated with the level of CA125 and a risk associated with the level of Pro108, and using the combined risks to assess the risk of Ovarian Cancer in the patient. In one aspect of the invention the measuring of CA125 and Pro108 levels are done simultaneously. In another aspect of the invention the measuring of CA125 and Pro108 are done sequentially.

In yet another aspect of the invention, the respective levels of CA125 and Pro108 are based on dividing a patient population dataset into low levels of CA125 and elevated levels of Pro108 and a patient having both low CA125 and high Pro108 levels is indicative of heightened risk of Ovarian Cancer. The low levels of CA125 may be below about 30 U/mL.

The invention is also directed to a method for treating a subject with elevated risk of a Ovarian Cancer, comprising: selecting a subject who has low levels of CA125 and elevated levels of Pro108 and treating the subject with a therapy selected from the group consisting of surgery, radiation therapy, hormone therapy or chemotherapy so at to treat the subject with the elevated risk of Ovarian Cancer.

The invention is also directed to a method for selecting a patient for ovarian biopsy comprising measuring levels of both Pro108 and CA125 in the patient, analyzing a risk associated with the level of CA125 and a risk associated with the level of Pro108, and based on the combined levels of both Pro108 and CA125 selecting the patient for ovarian biopsy.

Moreover, the invention is directed to a kit for determining the likelihood of a patient having Ovarian Cancer which comprises both a suitable assay for measuring Pro108 levels and a suitable assay for measuring CA125 levels wherein the levels of both CA125 and Pro108 are determined using the combined results.

This invention is further directed to a method for assessing risk of prostate cancer in a patient which comprises measuring levels of both Pro108 and Prostate Specific Antigen (PSA) in the patient, analyzing a risk associated with the level of PSA and a risk associated with the level of Pro108, and using the combined risks to assess the risk of prostate cancer in the patient. In one aspect of the invention the measuring of PSA and Pro108 levels are done simultaneously. In another aspect of the invention the measuring of PSA and Pro108 are done sequentially.

In yet another aspect of the invention, the respective levels of PSA and Pro108 are based on dividing a patient population dataset into borderline levels of PSA and elevated levels of Pro108 and a patient having both borderline PSA and high Pro108 levels is indicative of heightened risk of prostate cancer. The borderline levels of PSA may be between about 2 ng/mL and about 10 ng/mL. The borderline levels of PSA may also between about 4 ng/mL and about 10 ng/mL or between about 2 ng/mL and about 4 ng/mL.

The invention is also directed to a method for treating a subject with elevated risk of a prostate cancer, comprising: selecting a subject who has borderline levels of Prostate Specific Antigen (PSA) and elevated levels of Pro108 and treating the subject with a therapy selected from the group consisting of surgery, radiation therapy, hormone therapy or chemotherapy so at to treat the subject with the elevated risk of prostate cancer.

The invention is also directed to a method for selecting a patient for prostate biopsy comprising measuring levels of both Pro108 and Prostate Specific Antigen (PSA) in the patient, analyzing a risk associated with the level of PSA and a risk associated with the level of Pro108, and based on the combined levels of both Pro108 and PSA selecting the patient for prostate biopsy.

The invention also involves comparing the level of Pro108 or PSA for the individual with a predetermined value. The predetermined value can take a variety of forms. It can be single cut-off value, such as a median or mean. It can be established based upon comparative groups, such as where the risk in one defined group is double the risk in another defined group. It can be a range, for example, where the tested population is divided equally (or unequally) into groups, e.g., tertiles, such as-a low-risk group, a medium-risk group and a high-risk group, or into quadrants, the lowest quadrant being individuals with the lowest risk and the highest quadrant being individuals with the highest risk.

There presently are commercial sources which produce reagents for assays for PSA. These include, but are not limited to, Abbott Pharmaceuticals (Abbott Park, Ill.); Fujirebio Inc. (Tokyo, Japan), Biocheck Inc. (Burlingame, Calif.), Dade Behring (Deerfield, Ill.), Beckman Coulter Inc. (Chaska, Minn.); Roche Diagnostics (Indianapolis, Ind.). In preferred embodiments the invention provides novel kits or assays which are specific for, and have appropriate sensitivity with respect to, predetermined values selected on the basis of the present invention.

The preferred kits, therefore, would differ from those presently commercially available, by including, for example, different cut-offs, different sensitivities at particular cut-offs as well as instructions or other printed material for characterizing risk based upon the outcome of the assay.

As discussed herein the invention provides methods for evaluating the likelihood that an individual will benefit from treatment with an agent for reducing risk of prostate, ovarian, colon, breast or stomach cancer. This method has important implications for patient treatment and also for clinical development of new therapeutics. Physicians select therapeutic regimens for patient treatment based upon the expected net benefit to the patient. The net benefit is derived from the risk to benefit ratio. The present invention permits selection of individuals who are more likely to benefit by intervention, thereby aiding the physician in selecting a therapeutic regimen. This might include using drugs with a higher risk profile where the likelihood of expected benefit has increased. Likewise, clinical investigators desire to select for clinical trials a population with a high likelihood of obtaining a net benefit. The present invention can help clinical investigators select such individuals. It is expected that clinical investigators now will use the present invention for determining entry criteria for clinical trials.

Moreover, the invention is directed to a kit for determining the likelihood of a patient having prostate cancer which comprises both a suitable assay for measuring Pro108 levels and a suitable assay for measuring Prostate Specific Antigen (PSA) levels wherein the levels of both PSA and Pro108 are determined using the combined results.

In addition, the invention is directed to an article of manufacture comprising a container and a composition contained therein, wherein the composition comprises an antibody as described herein. The article of manufacture may also comprise an additional component, e.g., a package insert indicating that the composition can be used to treat prostate, ovarian, colon, breast or stomach cancer.

BRIEF DESCRIPTION OF THE FIGURES

FIG. 1 shows the anti-Pro108 antibody epitope mapping.
FIG. 2 shows Pro108 serum levels in healthy subjects and subjects with various cancers.
FIG. 3 shows Pro108 levels in prostate cancer and benign prostate disease.
FIG. 4 shows Pro108 levels in ovarian cancer and benign ovarian disease.
FIG. 5 shows Pro108 levels in serous and mucinous ovarian cancer and in benign ovarian disease.
FIG. 6 shows Pro108 levels in colon cancer and benign colon disease.
FIG. 7 shows Pro108 levels in stomach cancer.
FIG. 8 shows detection of Pro108 in the lysate of normal somatic and cancer tissues.

DETAILED DESCRIPTION OF THE INVENTION

Definitions and General Techniques

Human Pro108 as used herein, refers to a protein of 331 amino acids, the nucleotide and amino acid sequences were previously disclosed in WO200023108-A1 as Cancer specific gene Pro108; EP1130094-A2 as Human polypeptide SEQ ID NO: 2847; WO200229038-A2 as Human Spondin 2-like protein NOV6; DE10050274-A1 as Human spondin 2; WO200230268-A2 as Prostate cancer-associated protein #7, WO2003009814-A2 as Prostate cancer marker protein; WO200153312-A1 as Human polypeptide SEQ ID NO 5589; US2003104998-A1 as Human secreted/transmembrane protein, PRO866; and WO0144291-A2 as RG1.

Human Pro108 has also been identified as Spondin 2. The RefSeq database identifies Spondin 2 as "*Homo sapiens* spondin 2, extracellular matrix protein (SPON2)" and references the nucleotide and amino acid sequences as NM_012445 and NP_036577, respectively. Pro108 as used herein include allelic variants and conservative substitution mutants of the protein which have Pro108 biological activity.

Spondin 2 (Pro108) has been described as a gene differentially expressed in cancerous and non-cancerous lung cells, with higher mRNA expression in normal lung. Manda, R. et al., 1999, Genomics, 61: 5-14. The gene encodes a protein of 331 amino acids with a calculated molecular mass of 35 kD. Sequence analysis indicates the existence of a signal sequence within the first 27 amino acids therefore amino acids 27-331 are presumably secreted from cells. In addition, sequence analysis identifies Spondin 2 as a human homologue of the zebrafish genes, Mindin1 and Mindin2, which are members of the F-spondin superfamily genes. The F-spondin superfamily genes encode proteins with two conserved domains, FS1 and FS2, near the amino terminus. Additionally, at least one thrombospondin type I repeat is present at the carboxy-terminus. The F-Spondin genes products are secreted and are likely to be extracellular matrix molecules (ECM). ECM molecules are known to play a role in cell adhesion which is critical for maintaining tissue architecture, cellular differentiation, cellular function, growth and apoptosis. ECM molecules have also been implicated in human carcinogenesis, tumor invasion and malignant transformation. Disruption of maintenance of cell-ECM adhesion is a well know indicator of tumor progression and malignant transformation. Variations in levels of other ECM molecules such as fibronectin (FM) have been associated with cancerous and malignant tissues compared to normal tissues. Chakrabarty, S. et al. *Chapter 36 Adhesion Molecules as Tumor Markers*, Tumor Markers, Diamandis, E. Ed. (2002). Likewise, variations in Pro108 levels in the ECM and in plasma or serum is anticipated to be involved with, and indicate changes in maintenance of tissue architecture, cellular differentiation, cellular function, growth, apoptosis, and promotion of carcinogenesis, tumor invasion and malignant transformation.

It has been shown that the Trombospondin type I repeat, present in Pro108, has the ability to inhibit angiogenesis and it also inhibits the growth of several melanoma cell lines. Tolsma, S. et al., 1993, J. Cell Biol. 122; 497-511; Terai, Y. et al., 2001, J Cell Physiol, 188: 394-402; Guo, N. H. et al., 1997, J. Peptide Res. 50: 210-221. Breakdown of the ECM allows for angiogenesis to occur which is required for tumor growth and progression. Therefore, maintenance of ECM molecule function and levels, such as Pro108, is essential in inhibiting angiogenesis and tumor growth and progression.

The closest human homolog of Spondin 2, F-Spondin, (or VSPG; M-Spondin in *drosophila*; SCO-Spondin in bovine) is a secreted adhesion molecule that is expressed at high level in the developing floor plate. Klar, A. et al., 1992, Cell, 69: 95-110. F-Spondin is required for accurate pathfinding of commissural axons and inhibits the outgrowth of embryonic motor neurons. Burstyn-Cohen, T. et al., 1999, Neuron, 23: 233-246; Tzarfati-Majar, V. et al., 2001, Proc Natl Acad Sci USA, 98: 4722-4727. The exact function of Pro108 is not known yet but a recent publication from He et al. describe the Pro108 mouse homologue mindin as pattern-recognition molecule involved in the innate immune response to microbial pathogens He, Y- W. et al., 2004, Nature Immunology 5, 88-97.

Our findings that Pro108 is associated with aggressive prostate, ovarian, colon, breast and stomach cancers make this extracellular matrix antigen an attractive target for detection, risk assessment, monitoring or immunotherapy of these and possibly other tumor types.

Prostate Specific Antigen (PSA) has also been described widely, for a recent review see Barry 2001. It is a glycoprotein produced in the epithelium of the prostate. A variety of diseases both benign and cancerous may cause elevated levels of PSA. The Physicians Health Study found subjects with a PSA level of greater than 4.0 ng/mL had a 46% specificity with to identify subjects that would have prostate cancer within the next 10 years. Gann 1995. Others have reported the following:

| PSA levels (ng/mL) | Probability of Prostate Cancer |
|---|---|
| 0-2.4 | Uncertain |
| 2.5-4.0 | 12-23% |
| 4.1-10.0 | 25% |
| >10.0 | >50% |

See Barry 2001 and the references cited therein.

Methods for treating prostate cancer have been discussed in the background section above. The level of the markers of this invention may be obtained by a variety of recognized methods. Typically, the level is determined by measuring the level of the marker in a body fluid, for example, blood, lymph, saliva, urine and the like. The preferred body fluid is blood. The level can be determined by ELISA, or immunoassays or other conventional techniques for determining the presence of the marker. Conventional methods include sending samples of a patient's body fluid to a commercial laboratory for measurement. For the measurement of PSA enzymatic assays may also be used, see U.S. Pat. Nos. 6,361,955 (Roche), 6,300,088 (Duke), 6,107,049 (Bayer) 5,939,533 (Lilja), 5,928,878 (Bayer), 5,856,182 (Beckman Coulter), 5,672,480 (Abbott Laboratories), 5,474,903 (Huland) or 5,242,802 (Hybritech), the contents of which are hereby incorporated by reference into the subject application.

The term "antibody" (Ab) as used herein includes monoclonal antibodies, polyclonal antibodies, multispecific antibodies (e.g. bispecific antibodies), and antibody fragments, so long as they exhibit the desired biological activity. The term "immunoglobulin" (Ig) is used interchangeably with "antibody" herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. Preferably, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α, δ and γ chains and four CH domains for μ and ε isotypes. Each L chain has at the N-terminus, a variable domain (VL) followed by a constant domain (CL) at its other end. The VL is aligned with the VH and the CL is aligned with the first constant domain of the heavy chain (CHI). Particular amino acid residues are believed to form an interface between the light chain and heavy chain variable domains. The pairing of a VH and VL together forms a single antigen-binding site. For the structure and properties of the different classes of antibodies, see, e.g., Basic and Clinical Immunology, 8th edition, Daniel P. Stites, Abba I. Teff and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated α, δ, ε, γ and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 1-10-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a P-sheet configuration, connected by three hypervariable regions, which form loops connecting, and in some cases forming part of, the P-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 5056 (L2) and 89-97 (L3) in the VL, and around about 1-35 (HI), 50-65 (H2) and 95-102 (113) in the VH; Kabat et al., Sequences of Proteins of Immunological Interest, 5th Ed. Public Health Service, National Institutes of Health, Bethesda, Md. (1991)) and/or those residues from a "hypervariable loop" (e.g. residues 26-32 (LI), 50-52 (L2) and 91-96 (U) in the VL, and 26-32 (HI), 53-55 (1-12) and 96-101 (H3) in the VH; Chothia and Lesk J. Mol. Biol. 196: 901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816, 567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a CL and at least heavy chain constant domains, CHI, CH2 and CH3. The constant domains may be native sequence constant domains (e.g. human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments. Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CHI). Each Fab fragment is monovalent with respect to antigen binding, i.e., it has a single antigen-binding site. Pepsin treatment of an antibody yields a single large F(ab')2 fragment which roughly corresponds to two disulfide linked Fab fragments having divalent antigen-binding activity and is still capable of cross-linking antigen. Fab' fragments differ from Fab fragments by having additional few residues at the carboxy terminus of the CHI domain including one or more cysteines from the antibody hinge region. Fab'-SH is the designation herein for Fab' in which the cysteine residue(s) of the constant domains bear a free thiol group. F(ab')2 antibody fragments originally were produced as pairs of 8 Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

A "native sequence" polypeptide is one which has the same amino acid sequence as a polypeptide (e.g., antibody) derived from nature. Such native sequence polypeptides can be isolated from nature or can be produced by recombinant or synthetic means. Thus, a native sequence polypeptide can have the amino acid sequence of a naturally occurring human polypeptide, murine polypeptide, or polypeptide from any other mammalian species.

The term "amino acid sequence variant" refers to a polypeptide that has amino acid sequences that differ to some extent from a native sequence polypeptide. Ordinarily, amino acid sequence variants of Pro108 will possess at least about 70% homology with the native sequence Pro108, preferably, at least about 80%, more preferably at least about 85%, even more preferably at least about 90% homology, and most preferably at least 95%. The amino acid sequence variants can possess substitutions, deletions, and/or insertions at certain positions within the amino acid sequence of the native amino acid sequence.

The phrase "functional fragment or analog" of an antibody is a compound having qualitative biological activity in common with a full-length antibody. For example, a functional fragment or analog of an anti-IgE antibody is one which can bind to an IgE immunoglobulin in such a manner so as to prevent or substantially reduce the ability of such molecule from having the ability to bind to the high affinity receptor, FcεRI.

"Homology" is defined as the percentage of residues in the amino acid sequence variant that are identical after aligning the sequences and introducing gaps, if necessary, to achieve the maximum percent homology. Methods and computer programs for the alignment are well known in the art. Sequence similarity may be measured by any common sequence analysis algorithm, such as GAP or BESTFIT or other variation Smith-Waterman alignment. See, T. F. Smith and M. S. Waterman, J. Mol. Biol. 147:195-197 (1981) and W. R. Pearson, Genomics 11:635-650 (1991).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332: 323-329 (1988); and Presta, Curr. Op. Struct. Biol. 2:593-596 (1992).

As used herein, an anti-Pro108 antibody that binds Pro108 in mammalian tissue in vivo is one that detectably (i.e. qualitative or quantitatively measurable) binds mammalian tissues expressing Pro108 in vivo. Specifically, the anti-Pro108 antibody will bind Pro108 in the Extra Cellular Matrix (ECM) of a mammalian tissue in vivo. The anti-Pro108 antibody may bind free Pro108 or Pro108 bound to a receptor molecule. Said receptor molecule may be located in the ECM or serum or on the surface of cells. Anti-Pro108 antibodies may be internalized when bound to Pro108 which is bound to a receptor on the cell surface. Said antibody includes antibody fragments, human or humanized antibodies and antibody conjugates. For therapeutic applications, inhibition of Pro108 activity or delivery of toxin in vivo is contemplated. The number of antibody molecules bound to Pro108 in the ECM will be sufficient or adequate to kill a Pro108-expressing cell, especially a Pro108-expressing cancer cell. Depending on the potency of the antibody or antibody conjugate, in some instances, binding of a single antibody molecule to Pro108 in the ECM is sufficient to kill the target Pro108-expressing cell. Loss of Pro108 function in the ECM or delivery of toxins to tissues with a Pro108-expressing cell is sufficient to kill a Pro108-expressing cell. For example, as stated above, ECM molecules are known to regulate critical cellular processes, such as growth, differentiation, and apoptosis and some are believed to be involved in human carcinogenesis. Inhibition of these functions by binding of an anti-Pro108 antibody to Pro108 is sufficient to kill tumor cells. Additionally, certain toxins are highly potent in killing such that internalization of one molecule of the toxin is sufficient to kill the tumor cell.

As used herein, an anti-Pro108 antibody that "internalizes" is one that is taken up by (i.e., enters) the cell upon binding to Pro108 on a mammalian cell (i.e. cell surface Pro108). The internalizing antibody will of course include antibody fragments, human or humanized antibody and antibody conjugate. For therapeutic applications, internalization in vivo is contemplated. The number of antibody molecules internalized will be sufficient or adequate to kill an Pro108-expressing cell, especially an Pro108-expressing cancer cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the tumor cell.

Whether an anti-Pro108 antibody internalizes upon binding Pro108 on a mammalian cell can be determined by various assays including those described in the experimental examples below. For example, to test internalization in vivo, the test antibody is labeled and introduced into an animal known to have Pro108 expressed on the surface of certain cells. The antibody can be radiolabeled or labeled with fluorescent or gold particles, for instance. Animals suitable for this assay include a mammal such as a NCR nude mouse that contains a human Pro108-expressing tumor transplant or xenograft, or a mouse into which cells transfected with human Pro108 have been introduced, or a transgenic mouse expressing the human Pro108 transgene. Appropriate controls include animals that did not receive the test antibody or that received an unrelated antibody, and animals that received an antibody to another antigen on the cells of interest, which antibody is known to be internalized upon binding to the antigen. The antibody can be administered to the animal, e.g., by intravenous injection. At suitable time intervals, tissue sections of the animal can be prepared using known methods or as described in the experimental examples below, and analyzed by light microscopy or electron microscopy, for internalization as well as the location of the internalized antibody in the cell. For internalization in vitro, the cells can be incubated in tissue culture dishes in the presence or absence of the relevant antibodies added to the culture media and processed for microscopic analysis at desired time points. The presence of an internalized, labeled antibody in the cells can be directly visualized by microscopy or by autoradiography if radiolabeled antibody is used. Alternatively, in a quantitative biochemical assay, a population of cells comprising Pro108-expressing cells are contacted in vitro or in vivo with a radiolabeled test antibody and the cells (if contacted in vivo, cells are then isolated after a suitable amount of time) are treated with a protease or subjected to an acid wash to remove uninternalized antibody on the cell surface. The cells are ground up and the amount of protease resistant, radioactive counts per minute (cpm) associated with each batch of cells is measured by passing the homogenate through a scintillation counter. Based on the known specific activity of the radiolabeled antibody, the number of antibody molecules internalized per cell can be deduced from the scintillation counts of the ground-up cells. Cells are "contacted" with antibody in vitro preferably in solution form such as by adding the cells to the cell culture media in the culture dish or flask and mixing the antibody well with the media to ensure uniform exposure of the cells to the antibody. Instead of adding to the culture media, the cells can be contacted with the test antibody in an isotonic solution such as PBS in a test tube for the desired time period. In vivo, the cells are contacted with antibody by any suitable method of administering the test antibody such as the methods of administration described below when administered to a patient.

The faster the rate of internalization of the antibody upon binding to the Pro108-expressing cell in vivo, the faster the desired killing or growth inhibitory effect on the target Pro108-expressing cell can be achieved, e.g., by a cytotoxic immunoconjugate. Preferably, the kinetics of internalization of the anti-Pro108 antibodies are such that they favor rapid killing of the Pro108-expressing target cell. Therefore, it is desirable that the anti-Pro108 antibody exhibit a rapid rate of internalization preferably, within 24 hours from administration of the antibody in vivo, more preferably within about 12 hours, even more preferably within about 30 minutes to 1 hour, and most preferably, within about 30 minutes. The present invention provides antibodies that internalize as fast as about 15 minutes from the time of introducing the anti-Pro108 antibody in vivo. The antibody will preferably be internalized into the cell within a few hours upon binding to Pro108 on the cell surface, preferably within 1 hour, even more preferably within 15-30 minutes.

To determine if a test antibody can compete for binding to the same epitope as the epitope bound by the anti-Pro108 antibodies of the present invention including the antibodies produced by the hybridomas deposited with the ATCC, a cross-blocking assay e.g., a competitive ELISA assay can be performed. In an exemplary competitive ELISA assay, Pro108-coated wells of a microtiter plate, or Pro108-coated sepharose beads, are pre-incubated with or without candidate competing antibody and then a biotin-labeled anti-Pro108 antibody of the invention is added. The amount of labeled anti-Pro108 antibody bound to the Pro108 antigen in the wells or on the beads is measured using avidin-peroxidase conjugate and appropriate substrate.

Alternatively, the anti-Pro108 antibody can be labeled, e.g., with a radioactive or fluorescent label or some other detectable and measurable label. The amount of labeled anti-Pro108 antibody that binds to the antigen will have an inverse correlation to the ability of the candidate competing antibody (test antibody) to compete for binding to the same epitope on the antigen, i.e., the greater the affinity of the test antibody for the same epitope, the less labeled anti-Pro108 antibody will be bound to the antigen-coated wells. A candidate competing antibody is considered an antibody that binds substantially to the same epitope or that competes for binding to the same epitope as an anti-Pro108 antibody of the invention if the candidate competing antibody can block binding of the anti-Pro108 antibody by at least 20%, preferably by at least 20-50%, even more preferably, by at least 50% as compared to a control performed in parallel in the absence of the candidate competing antibody (but may be in the presence of a known noncompeting antibody). It will be understood that variations of this assay can be performed to arrive at the same quantitative value.

An antibody having a "biological characteristic" of a designated antibody, such as any of the monoclonal antibodies Pro108.A2, Pro108.A5, Pro108.B1, Pro108.B2, Pro108.B3, Pro108.B4, Pro108.B5, Pro108.B6, Pro108.B7, Pro108.B8, Pro108.B9, Pro108.B10, Pro108.B11, Pro108.B12, Pro108.B13, Pro108.B14, Pro108.B15, Pro108.B16, Pro108.B17, Pro108.B18, Pro108.B19, Pro108.B20, Pro108.B21, Pro108.B22, Pro108.B23, Pro108.B24, Pro108.B25, Pro108.B26, Pro108.B27, Pro108.B28, Pro108.B29, Pro108.B30, Pro108.B31, Pro108.B32, Pro108.B33, Pro108.B34, Pro108.B35, Pro108.B36, Pro108.B37, Pro108.B38, Pro108.B39, Pro108.B40, Pro108.B41, Pro108.B42, Pro108.B43, Pro108.B44 or Pro108.B45, is one which possesses one or more of the biological characteristics of that antibody which distinguish it from other antibodies that bind to the same antigen, Pro108.A2, Pro108.A5, Pro108.B1, Pro108.B2, Pro108.B3, Pro108.B4, Pro108.B5, Pro108.B6, Pro108.B7, Pro108.B8, Pro108.B9, Pro108.B10, Pro108.B11, Pro108.B12, Pro108.B13, Pro108.B14, Pro108.B15, Pro108.B16, Pro108.B17, Pro108.B18, Pro108.B19, Pro108.B20, Pro108.B21, Pro108.B22, Pro108.B23, Pro108.B24, Pro108.B25, Pro108.B26, Pro108.B27, Pro108.B28, Pro108.B29, Pro108.B30, Pro108.B31, Pro108.B32, Pro108.B33, Pro108.B34, Pro108.B35, Pro108.B36, Pro108.B37, Pro108.B38, Pro108.B39, Pro108.B40, Pro108.B41, Pro108.B42, Pro108.B43, Pro108.B44 or Pro108.B45 will bind the same epitope as that bound by Pro108.A2, Pro108.A5, Pro108.B1, Pro108.B2, Pro108.B3, Pro108.B4, Pro108.B5, Pro108.B6, Pro108.B7, Pro108.B8, Pro108.B9, Pro108.B10, Pro108.B11, Pro108.B12, Pro108.B13, Pro108.B14, Pro108.B15, Pro108.B16, Pro108.B17, Pro108.B18, Pro108.B19, Pro108.B20, Pro108.B21, Pro108.B22, Pro108.B23, Pro108.B24, Pro108.B25, Pro108.B26, Pro108.B27, Pro108.B28, Pro108.B29, Pro108.B30, Pro108.B31, Pro108.B32, Pro108.B33, Pro108.B34, Pro108.B35, Pro108.B36, Pro108.B37, Pro108.B38, Pro108.B39, Pro108.B40, Pro108.B41, Pro108.B42, Pro108.B43, Pro108.B44 or Pro108.B45 (e.g. which competes for binding or blocks binding of monoclonal antibody Pro108.A2, Pro108.A5, Pro108.B1, Pro108.B2, Pro108.B3, Pro108.B4, Pro108.B5, Pro108.B6, Pro108.B7, Pro108.B8, Pro108.B9, Pro108.B10, Pro108.B11, Pro108.B12, Pro108.B13, Pro108.B14, Pro108.B15, Pro108.B16, Pro108.B17, Pro108.B18, Pro108.B19, Pro108.B20, Pro108.B21, Pro108.B22, Pro108.B23, Pro108.B24, Pro108.B25, Pro108.B26, Pro108.B27, Pro108.B28, Pro108.B29, Pro108.B30, Pro108.B31, Pro108.B32, Pro108.B33, Pro108.B34, Pro108.B35, Pro108.B36, Pro108.B37, Pro108.B38, Pro108.B39, Pro108.B40, Pro108.B41, Pro108.B42, Pro108.B43, Pro108.B44 or Pro108.B45 to Pro108), be able to target an Pro108-expressing tumor cell in vivo and will bind to Pro108 on a mammalian cell in vivo.

Furthermore, an antibody with the biological characteristic of the Pro108.A2, Pro108.A5, Pro108.B1, Pro108.B2, Pro108.B3, Pro108.B4, Pro108.B5, Pro108.B6, Pro108.B7, Pro108.B8, Pro108.B9, Pro108.B10, Pro108.B11, Pro108.B12, Pro108.B13, Pro108.B14, Pro108.B15, Pro108.B16, Pro108.B17, Pro108.B18, Pro108.B19, Pro108.B20, Pro108.B21, Pro108.B22, Pro108.B23, Pro108.B24, Pro108.B25, Pro108.B26, Pro108.B27, Pro108.B28, Pro108.B29, Pro108.B30, Pro108.B31, Pro108.B32, Pro108.B33, Pro108.B34, Pro108.B35, Pro108.B36, Pro108.B37, Pro108.B38, Pro108.B39, Pro108.B40, Pro108.B41, Pro108.B42, Pro108.B43, Pro108.B44 or Pro108.B45 antibody will bind to Pro108 in mammalian tissue in vivo.

Likewise, an antibody with the biological characteristic of the Pro108.A2, Pro108.A5, Pro108.B1, Pro108.B2, Pro108.B3, Pro108.B4, Pro108.B5, Pro108.B6, Pro108.B7, Pro108.B8, Pro108.B9, Pro108.B10, Pro108.B11, Pro108.B12, Pro108.B13, Pro108.B14, Pro108.B15, Pro108.B16, Pro108.B17, Pro108.B18, Pro108.B19, Pro108.B20, Pro108.B21, Pro108.B22, Pro108.B23, Pro108.B24, Pro108.B25, Pro108.B26, Pro108.B27, Pro108.B28, Pro108.B29, Pro108.B30, Pro108.B31, Pro108.B32, Pro108.B33, Pro108.B34, Pro108.B35, Pro108.B36, Pro108.B37, Pro108.B38, Pro108.B39, Pro108.B40, Pro108.B41, Pro108.B42, Pro108.B43, Pro108.B44 or Pro108.B45 antibody will have the same epitope binding, targeting, tissue staining, ECM localization, internalizing, tumor growth inhibitory and cytotoxic properties of the antibody.

The term "antagonist" antibody is used in the broadest sense, and includes an antibody that partially or fully blocks, inhibits, or neutralizes a biological activity of a native Pro108 protein disclosed herein. Methods for identifying antagonists of a Pro108 polypeptide may comprise contacting an Pro108 polypeptide or a cell expressing Pro108 on the cell surface, with a candidate antagonist antibody and measuring a detectable change in one or more biological activities normally associated with the Pro108 polypeptide.

An "antibody that inhibits the growth of tumor cells expressing Pro108" or a "growth inhibitory" antibody is one which binds to Pro108 and results in measurable growth inhibition of cancer cells expressing or overexpressing Pro108. Preferred growth inhibitory anti-Pro108 antibodies inhibit growth of Pro108-expressing tumor cells e.g., prostate, ovarian, colon, breast and stomach cancer cells) by greater than 20%, preferably from about 20% to about 50%, and even more preferably, by greater than 50% (e.g. from about 50% to about 100%) as compared to the appropriate control, the control typically being tumor cells not treated with the antibody being tested. Growth inhibition can be measured at an antibody concentration of about 0.1 to 30 pg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-Pro108 antibody at about 1 pg/kg to about 100 mg/kg body weight results in reduction in tumor size or tumor cell proliferation within about 5 days to 3 months from the first administration of the antibody, preferably within about 5 to 30 days.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses Pro108. Preferably the cell is a tumor cell, e.g. a prostate, ovarian, colon, breast or stomach cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cells in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126.330-41 (1995). Other FcRs, including those to be identified in the future, are encompassed by the term "FcR" herein. The term also includes the neonatal receptor, FcRn, which is responsible for the transfer, of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g. from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., J. Immunol. Methods 202:163 (1996) may be performed.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

A "Pro108-expressing cell" is a cell which expresses endogenous or transfected Pro108. Pro108 is typically secreted outside the cell (e.g. in the Extra Cellular Matrix, ECM), but may be transiently localized internally (e.g. in the cytoplasm or secretory organelles) or on the cell surface. A "Pro108-expressing cancer" is a cancer comprising cells that have Pro108 protein predominately present in the Extra Cellular Matrix (ECM). A "Pro108-expressing cancer" produces sufficient levels of Pro108 in the ECM of cells thereof, such that an anti-Pro108 antibody can bind thereto and have a therapeutic effect with respect to the cancer. A cancer which "overexpresses" Pro108 is one which has significantly higher levels of Pro108 in the ECM thereof, compared to a noncancerous cell of the same tissue type. Such overexpression may be caused by gene amplification or by increased transcription or translation. Pro108 overexpression may be determined in a diagnostic or prognostic assay by evaluating increased levels of the Pro108 protein present in the ECM (e.g. via an immunohistochemistry assay, ELISA, cell capture, FACS analysis). Alternatively, or additionally, one may measure levels of Pro108-encoding nucleic acid or mRNA in the cell, e.g. via fluorescent in situ hybridization; (FISH; see WO98/45479 published October, 1998), Southern blotting, Northern blotting, or polymerase chain reaction (PCR) techniques, such as real time quantitative PCR(RT-PCR). One may also study Pro108 overexpression by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. J. Immunol. Methods 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to Pro108 in tissues in the patient can be evaluated, e.g. by external scanning for radioactivity or by analyzing a biopsy taken from a patient previously exposed to the antibody. A Pro108-expressing cancer includes prostate, ovarian, colon, breast or stomach cancer.

Alternatively, or additionally, FISH assays such as the INFORM™ (sold by Ventana, Arizona) or PATHVISION™ (VySiS, Illinois) may be carried out on formalin-fixed, paraffin-embedded tumor tissue to determine the extent (if any) of Pro108 overexpression in the tumor. Pro108 overexpression or amplification may be evaluated using an in vivo diagnostic assay, e.g. by administering a molecule (such as an antibody) which binds the molecule to be detected and is tagged with a detectable label (e.g. a radioactive isotope or a fluorescent label) and externally scanning the patient for localization of the label.

A "mammal" for purposes of treating a cancer or alleviating the symptoms of cancer, refers to any mammal, including-humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an Pro108-expressing cancer if, after receiving a therapeutic amount of an anti-Pro108 antibody according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-Pro108 antibody may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR).

The term "therapeutically effective amount" refers to an amount of an antibody or a drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See preceding definition of "treating". To the extent the drug may prevent growth and/or kill existing cancer cells, it may be cytostatic and/or cytotoxic.

"Chronic" administration refers to administration of the agent(s) in a continuous mode as opposed to an acute mode, so as to maintain the initial therapeutic effect (activity) for an extended period of time.

"Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed.

Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, e.g., gelonin, ricin, saporin, and the various antitumor or anticancer agents disclosed below. Other cytotoxic agents are described below. A tumoricidal agent causes destruction of tumor cells.

A "growth inhibitory agent" when used herein refers to a compound or composition which inhibits growth of a cell, especially a Pro108-expressing cancer cell, either in vitro or in vivo. Thus, the growth inhibitory agent may be one which significantly reduces the percentage of Pro108-expressing cells in S phase. Examples of growth inhibitory agents include agents that block cell cycle progression (at a place other than S phase), such as agents that induce GI arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest GI also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" as used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

The term "epitope tagged" used herein refers to a chimeric polypeptide comprising an anti-Pro108 antibody polypeptide fused to a "tag polypeptide". The tag polypeptide has enough residues to provide an epitope against which an antibody can be made, yet is short enough such that it does not interfere with activity of the Ig polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined herein to have a molecular weight below about 500 Daltons.

The term "package insert" is used to refer to instructions customarily included in commercial packages of therapeutic products, that contain information about the indications, usage, dosage, administration, contraindications and/or warnings concerning the use of such therapeutic products.

An "isolated nucleic acid molecule" is a nucleic acid molecule, e.g., an RNA, DNA, or a mixed polymer, which is substantially separated from other genome DNA sequences as well as proteins or complexes such as ribosomes and polymerases, which naturally accompany a native sequence. The term embraces a nucleic acid molecule which has been removed from its naturally occurring environment, and includes recombinant or cloned DNA isolates and chemically synthesized analogues or analogues biologically synthesized by heterologous systems. A substantially pure nucleic acid molecule includes isolated forms of the nucleic acid molecule.

"Vector" includes shuttle and expression vectors and includes, e.g., a plasmid, cosmid, or phagemid. Typically, a plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in prokaryotic, e.g., bacterial, or eukaryotic cells. Suitable vectors are disclosed below.

The cell that produces an anti-Pro108 antibody of the invention will include the parent hybridoma cell e.g., the hybridomas that are deposited with the ATCC, as well as bacterial and eukaryotic host cells into which nucleic acid encoding the antibodies have been introduced. Suitable host cells are disclosed below.

RNA interference refers to the process of sequence-specific post transcriptional gene silencing in animals mediated by short interfering RNAs (siRNA) (Fire et al., 1998, Nature, 391, 806). The corresponding process in plants is commonly referred to as post transcriptional gene silencing or RNA silencing and is also referred to as quelling in fungi. The process of post transcriptional gene silencing is thought to be an evolutionarily conserved cellular defense mechanism used to prevent the expression of foreign genes which is commonly shared by diverse flora and phyla (Fire et al., 1999, Trends Genet., 15, 358). Such protection from foreign gene expression may have evolved in response to the production of double stranded RNAs (dsRNA) derived from viral infection or the random integration of transposon elements into a host genome via a cellular response that specifically destroys homologous single stranded RNA or viral genomic RNA. The presence of dsRNA in cells triggers the RNAi response though a mechanism that has yet to be fully characterized. This mechanism appears to be different from the interferon response that results from dsRNA mediated activation of protein kinase PKR and 2',5'-oligoadenylate synthetase resulting in non-specific cleavage of mRNA by ribonuclease L.

The presence of long dsRNAs in cells stimulates the activity of a ribonuclease III enzyme referred to as dicer. Dicer is involved in the processing of the dsRNA into short pieces of dsRNA known as short interfering RNAs (siRNA) (Berstein et al., 2001, Nature, 409, 363). Short interfering RNAs derived from dicer activity are typically about 21-23 nucleotides in length and comprise about 19 base pair duplexes. Dicer has also been implicated in the excision of 21 and 22 nucleotide small temporal RNAs (stRNA) from precursor RNA of conserved structure that are implicated in translational control (Hutvagner et al., 2001, Science, 293, 834). The RNAi response also features an endonuclease complex containing a siRNA, commonly referred to as an RNA-induced silencing complex (RISC), which mediates cleavage of single stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

Short interfering RNA mediated RNAi has been studied in a variety of systems. Fire et al., 1998, Nature, 391, 806, were the first to observe RNAi in C. Elegans. Wianny and Goetz, 1999, Nature Cell Biol., 2, 70, describe RNAi mediated by dsRNA in mouse embryos. Hammond et al., 2000, Nature, 404, 293, describe RNAi in Drosophila cells transfected with dsRNA. Elbashir et al., 2001, Nature, 411, 494, describe RNAi induced by introduction of duplexes of synthetic 21-nucleotide RNAs in cultured mammalian cells including human embryonic kidney and HeLa cells. Recent work in Drosophila embryonic lysates (Elbashir et al., 2001, EMBO J., 20, 6877) has revealed certain requirements for siRNA length, structure, chemical composition, and sequence that are essential to mediate efficient RNAi activity. These studies have shown that 21 nucleotide siRNA duplexes are most active when containing two nucleotide 3'-overhangs. Furthermore, complete substitution of one or both siRNA strands with 2'-deoxy(2'-H) or 2'-O-methyl nucleotides abolishes RNAi activity, whereas substitution of the 3'-terminal siRNA overhang nucleotides with deoxy nucleotides (2'-H) was shown to be tolerated. Single mismatch sequences in the center of the siRNA duplex were also shown to abolish RNAi activity. In addition, these studies also indicate that the position of the cleavage site in the target RNA is defined by the 5'-end of the siRNA guide sequence rather than the 3'-end (Elbashir et al., 2001, EMBO J., 20, 6877). Other studies have indicated that a 5'-phosphate on the target-complementary strand of a siRNA duplex is required for siRNA activity and that ATP is utilized to maintain the 5'-phosphate moiety on the siRNA (Nykanen et al., 2001, Cell, 107, 309).

Studies have shown that replacing the 3'-overhanging segments of a 21-mer siRNA duplex having 2 nucleotide 3' overhangs with deoxyribonucleotides does not have an adverse effect on RNAi activity. Replacing up to 4 nucleotides on each end of the siRNA with deoxyribonucleotides has been reported to be well tolerated whereas complete substitution with deoxyribonucleotides results in no RNAi activity (Elbashir et al., 2001, EMBO J., 20, 6877). In addition, Elbashir et al., supra, also report that substitution of siRNA with 2'-O-methyl nucleotides completely abolishes RNAi activity. Li et al., International PCT Publication No. WO 00/44914, and Beach et al., International PCT Publication No. WO 01/68836 both suggest that siRNA "may include modifications to either the phosphate-sugar back bone or the nucleoside to include at least one of a nitrogen or sulfur heteroatom", however neither application teaches to what extent these modifications are tolerated in siRNA molecules nor provide any examples of such modified siRNA. Kreutzer and Limmer, Canadian Patent Application No. 2,359,180, also describe certain chemical modifications for use in dsRNA constructs in order to counteract activation of double stranded-RNA-dependent protein kinase PKR, specifically 2'-amino or 2'-O-methyl nucleotides, and nucleotides containing a 2'-O or 4'-C methylene bridge. However, Kreutzer and Limmer similarly fail to show to what extent these modifications are tolerated in siRNA molecules nor do they provide any examples of such modified siRNA.

Parrish et al., 2000, Molecular Cell, 6, 1977-1087, tested certain chemical modifications targeting the unc-22 gene in C. elegans using long (>25 nt) siRNA transcripts. The authors describe the introduction of thiophosphate residues into these siRNA transcripts by incorporating thiophosphate nucleotide analogs with T7 and T3 RNA polymerase and observed that "RNAs with two (phosphorothioate) modified bases also had substantial decreases in effectiveness as RNAi triggers (data not shown); (phosphorothioate) modification of more than two residues greatly destabilized the RNAs in vitro and we were not able to assay interference activities." Id. at 1081. The authors also tested certain modifications at the 2'-position of the nucleotide sugar in the long siRNA transcripts and observed that substituting deoxynucleotides for ribonucleotides "produced a substantial decrease in interference activity", especially in the case of Uridine to Thymidine and/or Cytidine to deoxy-Cytidine substitutions. Id. In addition, the authors tested certain base modifications, including substituting 4-thiouracil, 5-bromouracil, 5-iodouracil, 3-(aminoallyl) uracil for uracil, and inosine for guanosine in sense and antisense strands of the siRNA, and found that whereas 4-thiouracil and 5-bromouracil were all well tolerated, inosine "produced a substantial decrease in interference activity" when incorporated in either strand. Incorporation of 5-iodouracil and 3-(aminoallyl)uracil in the antisense strand resulted in substantial decrease in RNAi activity as well.

Beach et al., International PCT Publication No. WO 01/68836, describes specific methods for attenuating gene expression using endogenously derived dsRNA. Tuschl et al., International PCT Publication No. WO 01/75164, describes a Drosophila in vitro RNAi system and the use of specific siRNA molecules for certain functional genomic and certain therapeutic applications; although Tuschl, 2001, Chem. Biochem., 2, 239-245, doubts that RNAi can be used to cure genetic diseases or viral infection due "to the danger of activating interferon response". Li et al., International PCT Publication No. WO 00/44914, describes the use of specific dsRNAs for use in attenuating the expression of certain target genes. Zernicka-Goetz et al., International PCT Publication No. WO 01/36646, describes certain methods for inhibiting the expression of particular genes in mammalian cells using certain dsRNA molecules. Fire et al., International PCT Publication No. WO 99/32619, describes particular methods for introducing certain dsRNA molecules into cells for use in inhibiting gene expression. Plaetinck et al., International PCT Publication No. WO 00/01846, describes certain methods for identifying specific genes responsible for conferring a particular phenotype in a cell using specific dsRNA molecules. Mello et al., International PCT Publication No. WO 01/29058, describes the identification of specific genes involved in dsRNA mediated RNAi. Deschamps Depaillette et al., International PCT Publication No. WO 99/07409, describes specific compositions consisting of particular dsRNA molecules combined with certain anti-viral agents. Driscoll et al., International PCT Publication No. WO 01/49844, describes specific DNA constructs for use in facilitating gene silencing in targeted organisms. Parrish et al., 2000, Molecular Cell, 6, 1977-1087, describes specific chemically modified siRNA constructs targeting the unc-22 gene of C. elegans. Tuschl et al., International PCT Publication No. WO 02/44321, describe certain synthetic siRNA constructs.

Compositions and Methods of the Invention

The invention provides anti-Pro108 antibodies. Preferably, the anti-Pro108 antibodies bind to Pro108 in mammalian tissue in vivo. The anti-Pro108 antibodies may also inhibit the growth, destroy or lead to the destruction of tumor cells expressing Pro108.

It was not apparent that Pro108 was ECM localized in the extracellular matrix. In addition the ability of an antibody to bind Pro108 in the ECM depends on several factors including the affinity, avidity, and isotype of the antibody, and the epitope that it binds. We have demonstrated herein that Pro108 is localized in the ECM of tissue upon binding by the anti-Pro108 antibodies of the invention. Additionally, it was demonstrated that the anti-Pro108 antibodies of the present invention can specifically target Pro108-expressing tumor cells or tissues in vivo and inhibit or kill these cells. These in vivo tumor targeting, and growth inhibitory properties of the anti-Pro108 antibodies make these antibodies very suitable for therapeutic uses, e.g., in the treatment of various cancers including prostate, ovarian, colon, breast or stomach cancer. Internalization of the anti-Pro108 antibody is preferred, e.g., if the antibody or antibody conjugate has an intracellular site of action and if the cytotoxic agent conjugated to the antibody does not readily cross the plasma membrane (e.g., the toxin calicheamicin). Internalization is not necessary if the antibodies or the agent conjugated to the antibodies do not have intracellular sites of action, e.g., if the antibody can kill the tumor cell by ADCC or some other mechanism.

It was not apparent that Pro108 was internalization-competent. In addition the ability of an antibody to internalize depends on several factors including the affinity, avidity, and isotype of the antibody, and the epitope that it binds. We have demonstrated herein that the cell surface Pro108 is internalization competent upon binding by the anti-Pro108 antibodies of the invention. Additionally, it was demonstrated that the anti-Pro108 antibodies of the present invention can specifically target Pro108-expressing tumor cells in vivo and inhibit or kill these cells. These in vivo tumor targeting, internalization and growth inhibitory properties of the anti-Pro108 antibodies make these antibodies very suitable for therapeutic uses, e.g., in the treatment of various cancers including prostate, ovarian, colon, breast or stomach cancer. Internalization of the anti-Pro108 antibody is preferred, e.g., if the antibody or antibody conjugate has an intracellular site of action and if the cytotoxic agent conjugated to the antibody does not readily cross the plasma membrane (e.g., the toxin calicheamicin). Internalization is not necessary if the antibodies or the agent conjugated to the antibodies do not have intracellular sites of action, e.g., if the antibody can kill the tumor cell by ADCC or some other mechanism.

The anti-Pro 08 antibodies of the invention also have various non-therapeutic applications. The anti-Pro108 antibodies of the present invention can be useful for diagnosis, staging or monitoring of Pro108-expressing cancers (e.g., IHC, radioimaging). They may be used alone or in combination with other ovarian cancer markers, including, but not limited to, CA125, HE4 and mesothelin. The antibodies are further useful in predicting outcome or response to a therapy. In predicting outcome or response to therapy anti-Pro108 antibodies are used to determine levels of Pro108, and Pro108 levels are associated with subjects who had a defined outcome or response to a therapy. Preferably, the antibodies are used to predict the outcome or response to therapy for a subject with a Pro108 expressing cancer.

Additionally, the anti-Pro108 antibodies can be useful for monitoring a subject's response to therapy. The therapy may be directed at Pro108 or Pro108 may act as a surrogate marker of response to a therapy. The antibodies are used to determine Pro108 levels, and as a marker for response to therapy a decrease in Pro108 expression in a Pro108 expressing cancer is indicative of a positive response to therapy. No change or an increase in Pro108 expression in a Pro108 expressing cancer is indicative of no response to therapy.

The anti-Pro108 antibodies are also useful for purification or immunoprecipitation of Pro108 from cells, for detection and quantitation of Pro108 in vitro, e.g. in an ELISA or a Western blot, to kill and eliminate Pro1018-expressing cells from a population of mixed cells as a step in the purification of other cells. The internalizing anti-Pro108 antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies, an antibody sequence is fused to a heterologous polypeptide sequence. The antibodies can be modified in the Fc region to provide desired effector functions. As discussed in more detail in the sections below, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

The antibody may compete for binding, or binds substantially to, the same epitope bound by the antibodies of the invention. Antibodies having the biological characteristics of the present anti-Pro108 antibodies of the invention are also contemplated, e.g., an anti-Pro108 antibody which has the biological characteristics of a monoclonal antibody produced by the hybridomas accorded ATCC accession numbers PTA-5885 and PTA-5886, specifically including the in vivo tumor targeting, internalization and any cell proliferation inhibition or cytotoxic characteristics. Specifically provided are anti-Pro108 antibodies that bind to an epitope present in amino acids 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-210, 210-220, 220-230, 230-240, 240-250, 250-260, 260-270, 270-280, 280-290, 290-300, 300-310, 310-320, 320-331 of human Pro108, SEQ ID NO: 1-2.

Methods of producing the above antibodies are described in detail below.

The present anti-Pro108 antibodies are useful for treating a Pro108-expressing cancer or alleviating one or more symptoms of the cancer in a mammal. Such a cancer includes prostate, ovarian, colon, breast and stomach cancer, cancer of the urinary tract, lung cancer and pancreatic cancer. Such a cancer includes more specifically, ovarian serous and mucinous adenocarcinoma, breast infiltrating ductal carcinoma, prostate adenocarcinoma, renal cell carcinomas, colorectal adenocarcinomas, lung adenocarcinomas, lung squamous cell carcinomas, and pleural mesothelioma. The breast cancer may be HER-2 negative or positive breast cancer. The cancers encompass metastatic cancers of any of the preceding, e.g., prostate, ovarian, colon, breast and stomach cancer metastases. The antibody is able to bind to at least a portion Pro108 in tissues with cancer cells that express Pro108 in the mammal and preferably is one that does not induce or that minimizes HAMA response. Preferably, the antibody is effective to destroy or kill Pro108-expressing tumor cells or inhibit the growth of such tumor cells, in vitro or in vivo, upon binding to Pro108 in the Extra Cellular Matrix. Such an antibody includes a naked anti-Pro108 antibody (not conjugated to any agent). Naked anti-Pro108 antibodies having tumor growth inhibition properties in vivo include the antibodies described in the Experimental Examples below. Naked antibodies that have cytotoxic or cell growth inhibition properties can be further conjugated with a cytotoxic agent to render them even more potent in tumor cell destruction. Cytotoxic properties can be conferred to an anti-Pro108 antibody by, e.g., conjugating the antibody with a cytotoxic agent, to form an immunoconjugate as described below. The cytotoxic agent or a growth inhibitory agent is preferably a small molecule. Toxins such as maytansin, maytansinoids, saporin, gelonin, ricin or calicheamicin and analogs or derivatives thereof, are preferable.

The invention provides a composition comprising an anti-Pro108 antibody of the invention, and a carrier. For the purposes of treating cancer, compositions can be administered to the patient in need of such treatment, wherein the composition can comprise one or more anti-Pro108 antibodies present as an immunoconjugate or as the naked antibody. Further, the compositions can comprise these antibodies in combination with other therapeutic agents such as cytotoxic or growth inhibitory agents, including chemotherapeutic agents. The invention also provides formulations comprising an anti-Pro108 antibody of the invention, and a carrier. The formulation may be a therapeutic formulation comprising a pharmaceutically acceptable carrier.

Another aspect of the invention is isolated nucleic acids encoding the anti-Pro108 antibodies of this invention. Nucleic acids encoding both the H and L chains and especially the hypervariable region residues, chains which encode the native sequence antibody as well as variants, modifications and humanized versions of the antibody, are encompassed.

The invention also provides methods useful for treating a Pro108-expressing cancer or alleviating one or more symptoms of the cancer in a mammal, comprising administering a therapeutically effective amount of an anti-Pro 108 antibody to the mammal. The antibody therapeutic compositions can be administered short term (acute) or chronic, or intermittent as directed by physician. Also provided are methods of inhibiting the growth of, and killing a Pro108 expressing cell. Finally, the invention also provides kits and articles of manufacture comprising at least one antibody of this invention, preferably at least one anti-Pro108 antibody of this invention that binds to Pro108 in tissue in vivo or at least one anti-Pro108 antibody which binds Pro108 in the ECM, of this invention. Kits containing anti-Pro108 antibodies find use in detecting Pro108 expression, or in therapeutic or diagnostic assays, e.g., for Pro108 cell killing assays or for purification and/or immunoprecipitation of Pro108 from cells, tissues or bodily fluids. Additionally, kits containing anti-Pro108 antibodies find use in monitoring Pro108 expression over time to determine progression or regression of a cancer. For example, for isolation and purification of Pro108, the kit can contain an anti-Pro108 antibody coupled to a solid support, e.g., a tissue culture plate or beads (e.g., sepharose beads). Kits can be provided which contain antibodies for detection and quantitation of Pro108 in vitro, e.g. in an ELISA or a Western blot. Such antibody useful for detection may be provided with a label such as a fluorescent or radiolabel.

Production of Anti-Pro108 Antibodies

The following describes exemplary techniques for the production of the antibodies useful in the present invention. Some of these techniques are described further in Example 1. The Pro108 antigen to be used for production of antibodies may be, e.g., the full length polypeptide or a portion thereof, including a soluble form of Pro108 lacking the signal peptide sequence, or synthetic peptides to selected portions of the protein.

Alternatively, cells expressing Pro108 (e.g. CHO, NIH-3T3 or other cell lines transformed to overexpress Pro108; prostate, ovarian, colon, breast, stomach or other Pro108-expressing tumor cell line), or secretory organelles prepared from such cells can be used to generate antibodies. The nucleotide and amino acid sequences of human and murine Pro108 are available as provided above or in public databases. Pro108 can be produced recombinantly in and isolated from, prokaryotic cells, e.g., bacterial cells, or eukaryotic cells using standard recombinant DNA methodology. Pro108 can be expressed as a tagged (e.g., epitope tag) or other fusion protein to facilitate its isolation as well as its identification in various assays.

Antibodies or binding proteins that bind to various tags and fusion sequences are available as elaborated below. Other forms of Pro108 useful for generating antibodies will be apparent to those skilled in the art.

Tags

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). The FLAG-peptide (Hopp et al., BioTechnology, 6:1204-1210 (1988)) is recognized by an anti-FLAG M2 monoclonal antibody (Eastman Kodak Co., New Haven, Conn.). Purification of a protein containing the FLAG peptide can be performed by immunoaffinity chromatography using an affinity matrix comprising the anti-FLAG M2 monoclonal antibody covalently attached to agarose (Eastman Kodak Co., New Haven, Conn.). Other tag polypeptides include the KT3 epitope peptide [Martin et al., Science, 255:192-194 (1992)]; an α-tubulin epitope peptide (Skinner et al., J. Biol. Chenz., 266:15163-15166 (1991)); and the T7 gene protein peptide tag (Lutz-Freyermuth et al., Proc. Natl. Acad. Sci. USA, 87:6393-6397 (1990)).

Polyclonal Antibodies

Polyclonal antibodies are preferably raised in animals, preferably non-human animals, by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups. Conjugates also can be made in recombinant cell culture as protein fusions.

Animals are immunized against the antigen, immunogenic conjugates, or derivatives by combining, e.g., 5-100 pg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Also, aggregating agents such as alum are suitably used to enhance the immune response.

Monoclonal Antibodies

Monoclonal antibodies may be made using the hybridoma method first described by Kohler et al., Nature, 256:495 (1975), or may be made by recombinant DNA methods (U.S. Pat. No. 4,816,567). In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a "fusion partner", e.g., a myeloma cell line using a suitable fusing agent, such as polyethylene glycol, to form a hybridoma cell (Goding, Monoclonal Antibodies. Principles and Practice, pp 103 (Academic Press, 1986)).

The hybridoma cells thus prepared are seeded and grown in a suitable culture medium which medium preferably contains one or more substances that inhibit the growth or survival of the unfused, fusion partner, e.g, the parental myeloma cells. For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-II mouse tumors available from the Salk Institute Cell Distribution Center, San Diego, Calif. USA, and SP-2 and derivatives e.g., X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980). Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp 103 (Academic Press, 1986)). Suitable culture media for this purpose include, for example, D-MEM or RPMI-1640 medium. In addition, the hybridoma cells may be grown in vivo as ascites tumors in an animal e.g, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transformed or transfected into prokaryotic or eukaryotic host cells such as, e.g., E coli cells, simian COS cells, Chinese Hamster Ovary (CHO) cells, or myeloma cells, that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Phickthun, Immunol. Revs., 130:151-188 (1992).

Further, the monoclonal antibodies or antibody fragments can be isolated from antibody phage libraries generated using the techniques described in McCafferty et al., Nature, 348: 552-554 (1990). Clackson et al., Nature, 352:624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain (CH and CL) sequences for the homologous murine sequences (U.S. Pat. No. 4,816,567; and Morrison, et al., Proc. Natl. Acad. Sci. USA, 81:6851 (1984)), or by fusing the immunoglobulin coding sequence with all or part of the coding sequence for a non-immunoglobulin polypeptide (heterologous polypeptide). The nonimmunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized Antibodies

Methods for humanizing non-human antibodies have been described in the art. Preferably, a humanized antibody has one or more amino acid residues introduced into it from a source which is nonhuman. These non-human amino acid residues are often referred to as "import" residues, which are typically taken from an "import" variable domain. Humanization can be essentially performed following the method of Winter and co-workers (Jones et al., Nature, 321:522-525 (1986); Reichmann et al., Nature, 332:323-327 (1988), Verhoeyen et al., Science, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol., 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art.

Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-Pro108 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); 5,545,807; and Alternatively, phage display technology (McCafferty et al., Nature 348: 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905. As discussed above, human antibodies may also be generated by in vitro activated B cells (see U.S. Pat. Nos. 5,567,610 and 5,229,275).

Antibody Fragments

In certain circumstances there are advantages of using antibody fragments, rather than whole antibodies. The smaller size of the fragments allows for rapid clearance, and may lead to improved access to solid tumors. Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E coli, thus allowing the facile production of large amounts of these fragments. Antibody fragments can be isolated from the antibody phage libraries discussed above. Alternatively, Fab'-SH fragments can be directly recovered from E. coli and chemically coupled to form F(ab)2 fragments (Carter et al., Bio/Technology 10: 163-167 (1992)). According to another approach, F(ab)2 fragments can be isolated directly from recombinant host cell culture. Fab and F(ab)2 fragment with increased in vivo half-life comprising a salvage receptor binding epitope residues are described in U.S. Pat. No. 5,869,046. Other techniques for the production of antibody fragments will be apparent to the skilled practitioner. The antibody of choice may also be a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Bispecific Antibodies

Bispecific antibodies are antibodies that have binding specificities for at least two different epitopes. Exemplary bispecific antibodies may bind to two different epitopes of the Pro108 protein. Other such antibodies may combine an Pro108 binding site with a binding site for another protein. Alternatively, an anti-Pro108.Arm may be combined with an arm which binds to a triggering molecule on a leukocyte such as a T cell receptor molecule (e.g. C133), or Fc receptors for IgG (FcγR), such as FcγRI (CD64), FcγRII (CD32) and FcγRIII (CD16), so as to focus and localize cellular defense mechanisms to the Pro108-expressing cell. Bispecific antibodies may also be used to localize cytotoxic agents to cells which express Pro108. These antibodies possess an Pro108-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab)$_2$ bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J, 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region (CHI) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Preferably, the bispecific antibodies in this approach are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 217-225 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers.

The "diabody" technology described by Hollinger et al., Proc. Natl. Acad. Sci. USA, 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1(X1n-VD2-(X2)n-Fc, wherein VDI is a first variable domain, VD2 is a second variable domain, Fc is one polypeptide chain of an Fc region, XI and X2 represent an amino acid or polypeptide, and n is 0 or 1. For instance, the polypeptide chain(s) may comprise: VH—CHI-flexible linker-VH—CHI-Fc region chain; or VH—CHI—VH—CHI-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Other Amino Acid Sequence Modifications

Amino acid sequence modification(s) of the anti-Pro108 antibodies described herein are contemplated. For example, it may be desirable to improve the binding affinity and/or other biological properties of the antibody. Amino acid sequence variants of the anti-Pro108 antibody are prepared by introducing appropriate nucleotide changes into the anti-Pro108 antibody nucleic acid, or by peptide synthesis.

Such modifications include, for example, deletions from, and/or insertions into, and/or substitutions of, residues within the amino acid sequences of the anti-Pro108 antibody. Any combination of deletion, insertion, and substitution is made to arrive at the final construct, provided that the final construct possesses the desired characteristics. The amino acid changes also may alter post-translational processes of the anti-Pro108 antibody, such as changing the number or position of glycosylation sites.

A useful method for identification of certain residues or regions of the anti-Pro108 antibody that are preferred locations for mutagenesis is called "alanine scanning mutagenesis" as described by Cunningham and Wells in Science, 244:1081-1085 (1989). Here, a residue or group of target residues within the anti-Pro108 antibody are identified (e.g., charged residues such as arg, asp, his, lys, and glu) and replaced by a neutral or negatively charged amino acid (most preferably alanine or polyalanine) to affect the interaction of the amino acids with Pro108 antigen.

Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at a target codon or region and the expressed anti-Pro108 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an anti-Pro108 antibody with an N-terminal methionyl residue or the antibody fused to a cytotoxic polypeptide. Other insertional variants of the anti-Pro108 antibody molecule include the fusion to the N- or C-terminus of the anti-Pro108 antibody to an enzyme (e.g. for ADEPT) or a fusion to a polypeptide which increases the serum half-life of the antibody.

Another type of variant is an amino acid substitution variant. These variants have at least one amino acid residue in the anti-Pro108 antibody molecule replaced by a different residue. The sites of greatest interest for substitutional mutagenesis include the hypervariable regions, but FR alterations are also contemplated. Conservative substitutions are shown in Table I under the heading of "preferred substitutions". If such substitutions result in a change in biological activity, then more substantial changes, denominated "exemplary substitutions" in Table 1, or as further described below in reference to amino acid classes, may be introduced and the products screened for a desired characteristic.

TABLE I

Amino Acid Substitutions

| Original | Exemplary Substitutions | Preferred Substitutions |
| --- | --- | --- |
| Ala (A) | val; leu; ile | Val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; | leu |
| Leu (L) | norleucine; ile; val; met; ala; | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | Phe |
| Val (V) | ile; leu; met; phe; ala; | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gin, his, lys, arg; (5) residues that influence chain orientation: gly, pro; and (6) aromatic: trp, tyr, phe.

Non-conservative substitutions will entail exchanging a member of one of these classes for another class, Any cysteine residue not involved in maintaining the proper conformation of the anti-Pro108 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human Pro108. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-Pro108 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared nucleic acid molecule encoding a variant or a non-variant version of the anti-Pro108 antibody.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of the antibody.

Screening for Antibodies with the Desired Properties

Techniques for generating antibodies have been described above. One may further select antibodies with certain biological characteristics, as desired.

The growth inhibitory effects of an anti-Pro108 antibody of the invention may be assessed by methods known in the art, e.g., using cells which express Pro108 either endogenously or following transfection with the Pro108 gene. For example, the tumor cell lines and Pro108-transfected cells provided in Example 1 below may be treated with an anti-Pro108 monoclonal antibody of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-Pro108 antibody of the invention. After antibody treatment, the cells are harvested and the amount of radioactivity incorporated into the DNA quantitated in a scintillation counter. Appropriated positive controls include treatment of a selected cell line with a growth inhibitory antibody known to inhibit growth of that cell line. Growth inhibition of tumor cells in vivo can be determined in various ways such as is described in the Experimental Examples section below. Preferably, the tumor cell is one that over-expresses Pro108. Preferably, the anti-Pro108 antibody will inhibit cell proliferation of a Pro108-expressing tumor cell in vitro or in vivo by about 25-100% compared to the untreated tumor cell, more preferably, by about 30-100%, and even more preferably by about 50-100% or 70-100%, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-Pro108 antibody at about 1 µg/kg to about 100 mg/kg body weight results in reduction in tumor size or tumor cell proliferation within about 5 days to 3 months from the first administration of the antibody, preferably within about 5 to 30 days.

To select for antibodies which induce cell death, loss of membrane integrity as indicated by, e.g., propidium iodide (PI), tryptan blue or 7AAD uptake may be assessed relative to a control. A PI uptake assay can be performed in the absence of complement and immune effector cells. Pro108-expressing tumor cells are incubated with medium alone or medium containing of the appropriate monoclonal antibody at e.g., about 110 µg/ml. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those antibodies which induce statistically significant levels of cell death as determined by PI uptake may be selected as cell death-inducing antibodies.

To screen for antibodies which bind to an epitope on Pro108 bound by an antibody of interest, e.g., the Pro108 antibodies of this invention, a routine cross-blocking assay such as that describe in *Antibodies, A Laboratory Manual*, Cold Spring Harbor Laboratory, Ed Harlow and David Lane (1988), can be performed. This assay can be used to determine if a test antibody binds the same site or epitope as an anti-Pro108 antibody of the invention. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of Pro108 can be used in competition assays with the test antibodies or with a test antibody and an antibody with a characterized or known epitope.

For example, a method to screen for antibodies that bind to an epitope which is bound by an antibody this invention may comprise combining an Pro108-containing sample with a test antibody and an antibody of this invention to form a mixture, the level of Pro108 antibody bound to Pro108 in the mixture is then determined and compared to the level of Pro108 antibody bound in the mixture to a control mixture, wherein the level of Pro108 antibody binding to Pro108 in the mixture as compared to the control is indicative of the test antibody's binding to an epitope that is bound by the anti-Pro108 antibody of this invention. The level of Pro108 antibody bound to Pro108 is determined by ELISA. The control may be a positive or negative control or both. For example, the control may be a mixture of Pro108, Pro108 antibody of this invention and an antibody known to bind the epitope bound by the Pro108 antibody of this invention. The anti-Pro108 antibody labeled with a label such as those disclosed herein. The Pro108 may be bound to a solid support, e.g., a tissue culture plate or to beads, e.g., sepharose beads.

Immunoconjugates

The invention also pertains to therapy with immunoconjugates comprising an antibody conjugated to an anti-cancer agent such as a cytotoxic agent or a growth inhibitory agent.

Chemotherapeutic agents useful in the generation of such immunoconjugates have been described above. Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

Preferably, an anti-Pro108 antibody (full length or fragments) of the invention is conjugated to one or more maytansinoid molecules.

Maytansinoids are mitototic inhibitors which act by inhibiting tubulin polymerization. Maytansine was first isolated from the cast African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al. Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses 3×10 5 HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-Pro108 Antibody-Maytansinoid Conjugates (Immunoconjugates)

Anti-Pro108 antibody-maytansinoid conjugates are prepared by chemically linking an anti-Pro108 antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al. Cancer Research 52: 127-131 (1992). The linking groups include disulfide groups, thioether groups, acid labile groups, photolabile groups, peptidase labile groups, or esterase labile groups, as disclosed in the above-identified patents, disulfide and thioether groups being preferred. Conjugates of the antibody and maytansinoid may be made using a variety of bifunctional protein coupling agents such as N-succinimidyl (2-pyridyldithio) propionate (SPDP), succinimidyl-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as his (p-azidobenzoyl) hexanediamine), bis-diazonium derivatives (such as bis-(p-diazoniumbenzoyl)-ethylenediamine), diisocyanates (such as toluene 2,6diisocyanate), and bis-active fluorine compounds (such as 1,5-difluoro-2,4-dinitrobenzene). Particularly preferred coupling agents include N-succinimidyl (2-pyridyldithio) propionate (SPDP) (Carlsson et al., Biochem. J. 173:723-737 [1978]) and N-succinimidyl (2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. Preferably, the linkage is formed at the C-3 position of maytansinol or a maytansinol analogue.

Calicheamicin

Another immunoconjugate of interest comprises an anti-Pro108 antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$, (Hinman et al. Cancer Research 53: 3336 (1993), Lode et al. Cancer Research 5 8: 2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-Pro108 antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296). Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993. The present invention further contemplates an immunoconjugate formed between an antibody and a compound with nucleolytic activity (e.g. a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-Pro108 antibodies. Examples include $At^{211}$, $I^{131}$, $I^{125}$, $In^{111}$, $Y^{90}$, $Re^{186}$, $Re^{188}$, $Sm^{153}$, $Bi^{212}$, $P^{32}$, and radioactive isotopes of Lu. When the conjugate is used for diagnosis, it may comprise a radioactive atom for scintigraphic studies, for example $Tc^{99M}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $Tc^{99M}$, $I^{123}$, $In^{111}$, $Re^{186}$, $Re^{188}$, can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl (2-pyridyidithio) propionate (SPDP), succinimidyl (N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon labeled 1-isothiocyanatobenzyl methyldiethylene triaminepentaacetic acid (MX-DTPA) is an exemplary chelating agent for conjugation of radionucleotide to the antibody. See WO 94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al. Cancer Research 52: 127-131 (1992); U.S. Pat. No. 5,208, 020) may be used.

Alternatively, a fusion protein comprising the anti-Pro108 antibody and cytotoxic agent may be made, e.g. by recombinant techniques or peptide synthesis. The length of DNA may comprise respective regions encoding the two portions of the conjugate either adjacent one another or separated by a region encoding a linker peptide which does not destroy the desired properties of the conjugate.

In addition, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as O-galactosidase and neuraminidase useful for converting glycosylated prodrugs into free drugs; β-lactamase useful for converting drugs derivatized with P-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a tumor cell population. The enzymes of this invention can be covalently bound to the anti-Pro108 antibodies by techniques well known in the art such as the use of the heterobifunctional crosslinking reagents discussed above.

Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., Nature, 312: 604-608 (1984).

Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The anti-Pro108 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81(19)1484 (1989).

Vectors, Host Cells, and Recombinant Methods

The invention also provides isolated nucleic acid molecule encoding the humanized anti-Pro108 antibody, vectors and host cells comprising the nucleic acid, and recombinant techniques for the production of the antibody. For recombinant production of the antibody, the nucleic acid molecule encoding it is isolated and inserted into a replicable vector for further cloning (amplification of the DNA) or inserted into a vector in operable linkage with a promoter for expression. DNA encoding the monoclonal antibody is readily isolated and sequenced using conventional procedures (e.g., by using oligonucleotide probes that are capable of binding specifically to nucleic acid molecules encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

Signal Sequence Component

The anti-Pro108 antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native anti-Pro108 antibody signal sequence, the signal sequence is substituted by a prokaryotic signal sequence selected, for example, from the group of the alkaline phosphatase, penicillinase, 1 pp, or heat-stable enterotoxin II leaders. For yeast secretion the native signal sequence may be substituted by, e.g., the yeast invertase leader, oc factor leader (including *Saccharomyces* and *Kluyveromyces* α-factor leaders), or acid phosphatase leader, the *C albicans* glucoamylase leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the anti-Pro108 antibody.

Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the anti-Pro108 antibody nucleic acid, such as DHFR, thymidine kinase, metallothionein-I and -11, preferably primate metallothionein genes, adenosine deaminase, ornithine decarboxylase, etc. For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding anti-Pro108 antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC No. 44076 or PEP4 Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 pm circular plasmid pKDI can be used for transformation of *Kluyveromyces* yeasts. Alternatively, an expression system for large-scale production of recombinant calf chymosin was reported for *K. lactis*. Van den Berg, Bio/Technology, 8:135 (1990). Stable multi-copy expression vectors for secretion of mature recombinant human serum albumin by industrial strains of *Kluyveromyces* have also been disclosed. Fleer et al., Bio/Technology, 9:968-975 (1991).

Promoter Component

Expression and cloning vectors usually contain a promoter that is recognized by the host organism and is operably linked to the anti-Pro108 antibody nucleic acid. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-Pro108 antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors. Examples of suitable promoter sequences for use with yeast hosts include the promoters for 3-phosphoglycerate kinase or other glycolytic enzymes, such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-Pro108 antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419, 446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

Enhancer Element Component

Transcription of a DNA encoding the anti-Pro108 antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the anti-Pro108 antibody-encoding sequence, but is preferably located at a site 5' from the promoter.

Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding anti-Pro108 antibody. One useful transcription termination component is the bovine growth hormone polyadenylation region. See WO 94/11026 and the expression vector disclosed therein.

Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W31 10 (ATCC 27,325) are suitable. These examples are illustrative rather than limiting.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.) which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g, in CHO cells.

In addition to prokaryotes, eukaryotic microbes such as filamentous fungi or yeast are suitable cloning or expression hosts for anti-Pro108 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccha-*

*romyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated anti-Pro108 antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, *Arabidopsis* and tobacco can also be utilized as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, 1413 8065); mouse mammary tumor (MMT 060562, ATCC CCL5 1); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for anti-Pro108 antibody production and cultured in conventional nutrient media modified as appropriate for inducing promoters, selecting transformants, or amplifying the genes encoding the desired sequences.

Culturing Host Cells

The host cells used to produce the anti-Pro108 antibody of this invention may be cultured in a variety of media. Commercially available media such as Ham's FIO (Sigma), Minimal Essential Medium (MEM)(Sigma), RPMI-1640 (Sigma), and Dulbecco's Modified Eagle's Medium (DMEM)(Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Anti-Pro108 Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human $\gamma 1$, $\gamma 2$, or $\gamma 4$ heavy chains (Lindmark et al., J. Immunol. Meth. 62:1-13 (1983)). Protein G is recommended for all mouse isotypes and for human $\gamma 3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SIDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations

Pharmaceutical formulations of the antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol, and meresol); low molecular weight (less than about 10 residues) polypeptides; proteins, such as serum albumin, gelatin, or immunoglobulins; hydrophilic polymers such as polyvinylpyllolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). The antibody preferably comprises the antibody at a concentration of between 5-200 mg/ml, preferably between 10-100 mg/ml.

The formulation herein may also contain more than one active compound as necessary for the particular indication being treated, preferably those with complementary activities that do not adversely affect each other. For example, in addition to the anti-Pro108 antibody which internalizes, it may be desirable to include in the one formulation, an additional antibody, e.g. a second anti-Pro108 antibody which binds a different epitope on Pro108, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−) hydroxybutyric acid.

The formulations to be used for in vivo administration must be sterile. This is readily accomplished by filtration through sterile filtration membranes.

Methods and Treatment Using Anti-Pro108 Antibodies

According to the present invention, the anti-Pro108 antibody that binds to Pro108 in a mammalian tissue in vivo is used to treat a subject in need thereof having a cancer characterized by Pro108-expressing cancer cells, in particular, ovarian, pancreatic, lung or breast cancer, such as ovarian serous or mucinous adenocarcinoma or breast infiltrating ductal carcinoma cancer, and associated metastases.

The cancer will generally comprise Pro108-expressing cells, such that the anti-Pro108 antibody is able to bind thereto. The cancer may be characterized by overexpression of Pro108 in the Extra Cellular Matrix (ECM) within a tissue and bodily fluids. While the cancer may be characterized by overexpression of the Pro108 molecule, the present application further provides a method for treating cancer which is not considered to be an Pro108-overexpressing cancer.

This invention also relates to methods for detecting cells which overexpress Pro108 and to diagnostic kits useful in detecting cells expressing Pro108 or in detecting Pro108 in serum from a patient. The methods may comprise combining a cell-containing test sample with an antibody of this invention, assaying the test sample for antibody binding to cells in the test sample and comparing the level of antibody binding in the test sample to the level of antibody binding in a control sample of cells. A suitable control is, e.g., a sample of normal cells of the same type as the test sample or a cell sample known to be free of Pro108 overexpressing cells. A level of Pro108 binding higher than that of such a control sample would be indicative of the test sample containing cells that overexpress Pro108. Alternatively the control may be a sample of cells known to contain cells that overexpress Pro108. In such a case, a level of Pro108 antibody binding in the test sample that is similar to, or in excess of, that of the control sample would be indicative of the test sample containing cells that overexpress Pro108.

Pro108 overexpression may be detected with a various diagnostic assays. For example, over expression of Pro108 may be assayed by immunohistochemistry (IHC). Parrafin embedded tissue sections from a tumor biopsy may be subjected to the IHC assay and accorded an Pro108 protein staining intensity criteria as follows.

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for Pro108 expression may be characterized as not overexpressing Pro108, whereas those tumors with 2+ or 3+ scores may be characterized as overexpressing Pro108.

Alternatively, or additionally, FISH assays such as the INFORM™ (sold by Ventana, Arizona) or PATHVISION™ (VySiS, Illinois) may be carried out on formalin-fixed, paraffin-embedded tumor tissue to determine the extent (if any)

of Pro108 overexpression in the tumor. Pro108 overexpression or amplification may be evaluated using an in vivo diagnostic assay, e.g. by administering a molecule (such as an antibody of this invention) which binds Pro108 and which is labeled with a detectable label (e.g. a radioactive isotope or a fluorescent label) and externally scanning the patient for localization of the label.

A sample suspected of containing cells expressing or overexpressing Pro108 is combined with the antibodies of this invention under conditions suitable for the specific binding of the antibodies to Pro108. Binding of Pro108 antibodies of this invention is indicative of the cells expressing Pro108. The level of binding may be determined and compared to a suitable control, wherein an elevated level of bound Pro108 as compared to the control is indicative of Pro108 overexpression. The sample suspected of containing cells overexpressing Pro108 may be a cancer cell sample, particularly a sample of prostate, ovarian, colon, breast or stomach cancer, e.g. ovarian serous or mucinous adenocarcinoma or a breast infiltrating ductal carcinoma. A serum sample from a subject may also be assayed for levels of Pro108 by combining a serum sample from a subject with an Pro108 antibody of this invention, determining the level of Pro108 bound to the antibody and comparing the level to a control, wherein an elevated level of Pro108 in the serum of the patient as compared to a control is indicative of overexpression of Pro108 by cells in the patient. The subject may have a cancer such as e.g., an ovarian cancer, e.g. ovarian serous adenocarcinoma, or a breast cancer, e.g., a breast infiltrating ductal carcinoma.

Currently, depending on the stage of the cancer, prostate, ovarian, colon, breast or stomach cancer treatment involves one or a combination of the following therapies: surgery to remove the cancerous tissue, radiation therapy, androgen deprivation (e.g., hormonal therapy), and chemotherapy. Anti-Pro108 antibody therapy may be especially desirable in elderly patients who do not tolerate the toxicity and side effects of chemotherapy well, in metastatic disease where radiation therapy has limited usefulness, and for the management of prostatic carcinoma that is resistant to androgen deprivation treatment. The tumor targeting anti-Pro108 antibodies of the invention are useful to alleviate Pro108-expressing cancers, e.g., prostate, ovarian, colon, breast or stomach cancers upon initial diagnosis of the disease or during relapse. For therapeutic applications, the anti-Pro108 antibody can be used alone, or in combination therapy with, e.g., hormones, anti-angiogens, or radiolabelled compounds, or with surgery, cryotherapy, and/or radiotherapy, notably for ovarian, pancreatic, lung or breast cancers, also particularly where shed cells cannot be reached. Anti-Pro108 antibody treatment can be administered in conjunction with other forms of conventional therapy, either consecutively with, pre- or post-conventional therapy, Chemotherapeutic drugs such as Taxotere® (docetaxel), Taxol® (paclitaxel), estramustine and mitoxantrone are used in treating metastatic and hormone refractory ovarian, pancreatic, lung or breast cancer, in particular, in good risk patients. In the present method of the invention for treating or alleviating cancer, in particular, androgen independent and/or metastatic ovarian, pancreatic, lung or breast cancer, the cancer patient can be administered anti-Pro108 antibody in conjunction with treatment with the one or more of the preceding chemotherapeutic agents. In particular, combination therapy with paclitaxel and modified derivatives (see, e.g., EP0600517) is contemplated. The anti-Pro108 antibody will be administered with a therapeutically effective dose of the chemotherapeutic agent. The anti-Pro108 antibody may also be administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

Particularly, an immunoconjugate comprising the anti-Pro108 antibody conjugated with a cytotoxic agent may be administered to the patient. Preferably, the immunoconjugate bound to Pro108 in the Extra Cellular Matrix (ECM) results in therapeutic efficacy of the immunoconjugate in killing the Pro108-expressing cancer cell. Alternatively, the immunoconjugate bound to the Pro108 protein is internalized by the cell, resulting in increased therapeutic efficacy of the immunoconjugate in killing the Pro108-expressing cancer cell. Preferably, the cytotoxic agent targets or interferes with the nucleic acid in the cancer cell. Examples of such cytotoxic agents are described above and include maytansin, maytansinoids, saporin, gelonin, ricin, calicheamicin, ribonucleases and DNA endonucleases.

The anti-Pro108 antibodies or immunoconjugates are administered to a human patient, in accord with known methods, such as intravenous administration, e.g., as a bolus or by continuous infusion over a period of time, by intramuscular, intraperitoneal, intracerebrospinal, subcutaneous, intra-articular, intrasynovial, intrathecal, oral, topical, or inhalation routes. The antibodies or immunoconjugates may be injected directly into the tumor mass. Intravenous or subcutaneous administration of the antibody is preferred. Other therapeutic regimens may be combined with the administration of the anti-Pro108 antibody.

The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-Pro108 antibody or antibodies, with administration of an antibody directed against another tumor antigen associated with the particular cancer. As such, this invention is also directed to an antibody "cocktail" comprising one or more antibodies of this invention and at least one other antibody which binds another tumor antigen associated with the Pro108-expressing tumor cells. The cocktail may also comprise antibodies that are directed to other epitopes of Pro108. Preferably the other antibodies do not interfere with the binding and or internalization of the antibodies of this invention.

The antibody therapeutic treatment method of the present invention may involve the combined administration of an anti-Pro108 antibody (or antibodies) and one or more chemotherapeutic agents or growth inhibitory agents, including co-administration of cocktails of different chemotherapeutic agents. Chemotherapeutic agents include, e.g., estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-Pro108 antibody (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody therapy. Suitable dosages for any of the above co-administered agents are those presently used and may be lowered due to the combined action (synergy) of the agent and anti-Pro108 antibody.

For the prevention or treatment of disease, the dosage and mode of administration will be chosen by the physician according to known criteria. The appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Preferably, the antibody is administered by intravenous infusion or by subcutaneous injections. Depending on the type and severity of the disease, about 1 pg/kg to about 50 mg/kg body weight (e.g. about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-Pro108 antibody. However, other dosage regimens may be useful. A typical daily dosage might range from about 1 pg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of a nucleic acid molecule encoding the antibody is encompassed by the expression "administering a therapeutically effective amount of an antibody". See, for example, WO 96/07321 published Mar. 14, 1996 concerning the use of gene therapy to generate intracellular antibodies.

There are two major approaches to introducing the nucleic acid molecule (optionally contained in a vector) into the patient's cells; in vivo and ex vivo. For in vivo delivery the nucleic acid molecule is injected directly into the patient, usually at the site where the antibody is required. For ex vivo treatment, the patient's cells are removed, the nucleic acid molecule is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acid molecules into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid molecule transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., Science 256:808-813 (1992). See also WO 93/25673 and the references cited therein.

Articles of Manufacture and Kits

The invention also relates to an article of manufacture containing materials useful for the detection for Pro108 overexpressing cells and/or the treatment of Pro108 expressing cancer, in particular prostate, ovarian, colon, breast and stomach cancer. The article of manufacture comprises a container and a composition contained therein comprising an antibody of this invention. The composition may further comprise a carrier. The article of manufacture may also comprise a label or package insert on or associated with the container. Suitable containers include, for example, bottles, vials, syringes, etc. The containers may be formed from a variety of materials such as glass or plastic. The container holds a composition which is effective for detecting Pro108 expressing cells and/or treating a cancer condition and may have a sterile access port (for example the container may be an intravenous solution bag or a vial having a stopper pierceable by a hypodermic injection needle). At least one active agent in the composition is an anti-Pro108 antibody of the invention. The label or package insert indicates that the composition is used for detecting Pro108 expressing cells and/or for treating prostate, ovarian, colon, breast or stomach cancer, or more specifically ovarian serous adenocarcinoma, breast infiltrating ductal carcinoma, prostate adenocarcinoma, renal cell carcinomas, colorectal adenocarcinomas, lung adenocarcinomas, lung squamous cell carcinomas, and pleural mesothelioma, in a patient in need thereof. The breast cancer may be HER-2 negative or positive breast cancer. The cancers encompass metastatic cancers of any of the preceding, e.g., prostate, ovarian, colon, breast or stomach cancer metastases. The label or package insert may further comprise instructions for administering the antibody composition to a cancer patient. Additionally, the article of manufacture may further comprise a second container comprising a substance which detects the antibody of this invention, e.g., a second antibody which binds to the antibodies of this invention. The substance may be labeled with a detectable label such as those disclosed herein. The second container may contain e.g., a pharmaceutically-acceptable buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

Kits are also provided that are useful for various purposes, e.g., for Pro108 cell killing assays, for purification or immunoprecipitation of Pro108 from cells or for detecting the presence of Pro108 in a serum sample or detecting the presence of Pro108-expressing cells in a cell sample. For isolation and purification of Pro108, the kit can contain an anti-Pro108 antibody coupled to a solid support, e.g., a tissue culture plate or beads (e.g., sepharose beads). Kits can be provided which contain the antibodies for detection and quantitation of Pro108 in vitro, e.g. in an ELISA or a Western blot. As with the article of manufacture, the kit comprises a container and a composition contained therein comprising an antibody of this invention. The kit may further comprise a label or package insert on or associated with the container. The kits may comprise additional components, e.g., diluents and buffers, substances which bind to the antibodies of this invention, e.g., a second antibody which may comprise a label such as those disclosed herein, e.g., a radiolabel, fluorescent label, or enzyme, or the kit may also comprise control antibodies. The additional components may be within separate containers within the kit. The label or package insert may provide a description of the composition as well as instructions for the intended in vitro or diagnostic use.

EXAMPLES

Example 1

Production and Isolation of Monoclonal Antibody Producing Hybridomas

The following MAb/hybridomas of the present invention are described below: Pro108.A2, Pro108.A5, Pro108.B1, Pro108.B2, Pro108.B3, Pro108.B4, Pro108.B5, Pro108.B6, Pro108.B7, Pro108.B8, Pro108.B9, Pro108.B10, Pro108.B11, Pro108.B12, Pro108.B13, Pro108.B14, Pro108.B15, Pro108.B16, Pro108.B17, Pro108.B18, Pro108.B19, Pro108.B20, Pro108.B21, Pro108.B22, Pro108.B23, Pro108.B24, Pro108.B25, Pro108.B26, Pro108.B27, Pro108.B28, Pro108.B29, Pro108.B30, Pro108.B31, Pro108.B32, Pro108.B33, Pro108.B34, Pro108.B35, Pro108.B36, Pro108.B37, Pro108.B38, Pro108.B39, Pro108.B40, Pro108.B41, Pro108.B42, Pro108.B43, Pro108.B44, Pro108.B45.

If the MAb has been cloned, it will get the nomenclature "X.1," e.g., the first clone of A7 will be referred to as A7.1, the second clone of A7 will be referred to as A7.2, etc. For the purposes of this invention, a reference to A7 will include all clones, e.g., A7.1, A7.2, etc. An alternative nomenclature format without the "period" (.) punctuation between "Pro108" and the hybridoma may be employed and denotes the same MAb/hybridoma as one with the "period" (.) punctuation.

Immunogens and Antigens (Recombinant Proteins HA Tag & Transfected Cells)

Pro108 Expressed Sequence & Protein Production

A PCR fragment of Pro108 cDNA encoding Met1 to Val331 was introduced into an expression vector via recombination. The construct was cloned in-frame to a six-histidine tag, located at the C-terminal end, so that the Pro108 construct would be expressed as a six-histidine tagged protein of 349 amino acids. The recombinant plasmid was used to transform competent cells for generation of the infection vector by transposition. A Pro108 recombinant vector was expressed in suitable cell lines.

Construct Sequence (underlined recombination site; bold six histidine tag) (SEQ ID NO: 1):

```
MENPSPAAALGKALCALLLATLGAAGQPLGGESICSARAPAKYSITFTGK
WSQTAFPKQYPLFRPPAQWSSLLGAAHSSDYSMWRKNQYVSNGLRDFAER
GEAWALMKEIEAAGEALQSVHEVFSAPAVPSGTGQTSAELEVQRRHSLVS
FVVRIVPSPDWFVGVDSLDLCDGDRWREQAALDLYPYDAGTDSGFTFSSP
NFATIPQDTVTEITSSSPSHPANSFYYPRLKALPPIARVTLVRLRQSPRA
FIPPAPVLPSRDNEIVDSASVPETPLDCEVSLWSSWGLCGGHCGRLGTKS
RTRYVRVQPANNGSPCPELEEEAECVPDNCVDPAFLYKVVRWAHHHHHH
```

Cells expressing Pro108 were lysed in a buffer containing 0.4 M NaCl, 100 mM Na2HPO3/NaH2PO3, 10% glycerol, 1% Triton X-100, and 10 mM imidazole, pH 8.0. The extracts were centrifuged at about 40,000 g and the recovered pellets were dissolved in a strong chaotropic buffer containing 8 M urea, 1 M NaCl, 0.1 M Na2HPO3/NaH2PO3, pH 8.1. The suspended samples were stirred overnight at room temperature and then clarified by centrifugation and filtration. The supernatants were loaded onto a Ni-NTA column, equilibrated with a buffer containing 8 M urea, 5 mM β-ME, and 10 mM imidazole, pH 8.0. The columns were then washed with the same buffers with increasing concentration of imidazole. The most stringent wash contained 100 mM imidazole. Following the elution, proteins were precipitated by dialysis against PBS, pH 7.2, and used as a homogenized suspension.

Pro108 293T Cell Expressed Sequence & Protein Production

A PCR fragment of Pro108 cDNA encoding Met1 to Val331 was introduced in an expression vector via recombination. The construct was cloned in-frame to a V5 epitope and six-histidine tag, located at the C-terminal end, so that the Pro108 construct would be expressed as a V5 epitope/six-histidine tagged protein of 371 amino acids. The resulted plasmid was used to transfect a 293T suspension culture and the recombinant Pro108 protein was recovered from culture media for purification.

Construct Sequence (SEQ ID NO:2):

```
MENPSPAAALGKALCALLLATLGAAGQPLGGESICSARAPAKYSITFTGK
WSQTAFPKQYPLFRPPAQWSSLLGAAHSSDYSMWRKNQYVSNGLRDFAER
GEAWALMKEIEAAGEALQSVHEVFSAPAVPSGTGQTSAELEVQRRHSLVS
FVVRIVPSPDWFVGVDSLDLCDGDRWREQAALDLYPYDAGTDSGFTFSSP
NFATIPQDTVTEITSSSPSHPANSFYYPRLKALPPIARVTLLRLRQSPRA
FIPPAPVLPSRDNEIVDSASVPETPLDCEVSLWSSWGLCGGHCGRLGTKS
RTRYVRVQPANNGSPCPELEEEAECVPDNCVDPAFLYKVVDLEGPRFEGK
PIPNPLLGLDSTRTGHHHHHH
```

Recombinant mammalian Pro108 was harvested from both the media and cells of a transiently transfected 293T suspension culture. Concentrated culture media were exchanged into PBS, pH 7.9, by diafiltration and cells were lysed in 100 mM Na2HPO3/NaH2PO3, pH 8.0, containing 0.4 M NaCl, 10% glycerol, 1% Triton X-100, and 10 m M imidazole. Following the buffer exchange or lysis, the sample was centrifuged and the supernatant was filtered through a 10 filter. The filtered sample was then loaded onto a Ni-NTA column and the intended Pro108 was bound on the column efficiently.

The column was washed with the buffer containing 0.4 M NaCl, 100 mM Na2HPO3/NaH2PO3, 10% glycerol, and 50 mM imidazole, pH 8.0. The protein was then eluted in the same buffer containing 1 M imidazole. Following the elution, Pro108 was dialyzed into a buffer containing 0.1 M sodium phosphate, 0.5 M NaCl, 10% glycerol, pH 8.0.

Pro111 Expressed Sequence & Protein Production

Pro111 (human prostate-specific transglutaminase) protein was used as the control for Pro108 antibody screening. The recombinant construct encoding Met1 to Lys684 was generated by introduction of a cDNA fragment into an expression vector via recombination. The construct was cloned in-frame to a six-histidine tag, located at the C-terminal end, so that Pro111 would be expressed as a six-histidine tagged protein of 690 amino acids. The recombinant plasmid was used to transform competent cells. A Pro111 expressing recombinant vector was expressed in suitable cells.

Construct Sequence (bold six histidine tag) (SEQ ID NO:3):

MMDASKELQVLHIDFLNQDNAVSHHTWEFQTSSPVFRRGQVFHLRLVLNQ

PLQSYHQLKLEFSTGPNPSIAKHTLVVLDPRTPSDHYNWQATLQNESGKE

VTVAVTSSPNAILGKYQLNVKTGNHILKSEENILYLLFNPWCKEDMVFMP

DEDERKEYILNDTGCHYVGAARSIKCKPWNFGQFEKNVLDCCISLLTESS

LKPTDRRDPVLVCRAMCAMMSFEKGQGVLIGNWTGDYEGGTAPYKWTGSA

PILQQYYNTKQAVCFGQCWVFAGILTTVLRALGIPARSVTGFDSAHDTER

NLTVDTYVNENGEKITSMTHDSVWNFHVWTDAWMKRPDLPKGYDGWQAVD

ATPQERSQGVFCCGPSPLTAIRKGDIFIVYDTRFVFSEVNGDRLIWLVKM

VNGQEELHVISMETTSIGKNISTKAVGQDRRRDITYEYKYPEGSSEERQV

MDHAFLLLSSEREHRRPVKENFLHMSVQSDDVLLGNSVNFTVILKRKTAA

LQNVNILGSFELQLYTGKKMAKLCDLNKTSQIQGQVSEVTLTLDSKTYIN

SLAILDDEPVIRGFIIAEIVESKEIMASEVFTSFQYPEFSIELPNTGRIG

QLLVCNCIFKNTLAIPLTDVKFSLESLGISSLQTSDHGTVQPGETIQSQI

KCTPIKTGPKKFIVKLSSKQVKEINAQKIVLITKHHHHHH

Cells producing recombinant Pro111 were lysed in a buffer containing 0.4 M NaCl, 0.1 M Na2HPO3/NaH2PO3, 1% Triton X-100, and 10 mM imidazole, pH 8.0, with protease inhibitor cocktail and DNase. After one hour stirring on ice, the sample was centrifuged and the supernatant was filtered and passed through a Ni-NTA column. The column was washed with buffers containing 0.4 M NaCl, 0.1 M Na2HPO3/NaH2PO3, pH 8.0, with a linear increase of imidazole concentration to 100 mM. The intended Pro111 was then eluted from the column with the same buffer containing 1 M imidazole. Following the elution, the protein was dialyzed into a buffer containing 0.1 M sodium phosphate, 0.5 M NaCl and 10% glycerol, pH 8.0.

Immunizations

For generation of both the A and B series MAbs mice were immunized with insect expressed Pro108 recombinant protein, encoding a region of Pro108 from Met1 to Val331 of the full length protein. Groups of 8 BALB/c mice were immunized intradermally in both rear footpads. All injections were 25 uL per foot. The first injection (day 1) of 10 ug of insect expressed Pro108 per mouse was in Dulbecco's phosphate buffered saline (DPBS) mixed in equal volume to volume ratio with Titermax gold adjuvant (Sigma, Saint Louis, Miss.). Subsequent injections of 10 ug of insect expressed Pro108 per mouse occurred on days 5, 9, 12, 16, 19, 23, 26, 29, 30 and consisted of antigen in 20 uL of DPBS plus 5 uL of Adju-phos adjuvant (Accurate Chemical & Scientific Corp., Westbury, N.Y.) per mouse. For the A series MAbs the final boost injection on day 33 consisted of 10 ug of insect cell expressed Pro108 diluted in DPBS alone. For the B series MAbs the final boost injection on day 33 consisted of 4.8 ug of mammalian expressed Pro108 diluted in DPBS alone. Fusion occurred on Day 37.

Hybridoma Fusions

Mice were sacrificed at the completion of the immunization protocol and draining lymph node (popliteal) tissue was collected by sterile dissection. Lymph node cells were dispersed using a Tenbroeck tissue grinder (Wheaton #357426, VWR, Brisbane, Calif.) followed by pressing through a sterile 40 uM sieve (VWR) into DMEM and removing T-cells via anti-CD90 (Thy1.2) coated magnetic beads (Miltenyl Biotech, Baraisch-Gladbach, Germany).

These primary B-cell enriched lymph node cells were then immortalized by electro-cell fusion (BTX, San Diego, Calif.) with the continuous myeloma cell line P3x63Ag8.653 (Kearney, J. F. et al., J. Immunology 123: 1548-1550, 1979). Successfully fused cells were selected by culturing in standard Hypoxanthine, Azaserine (HA) (Sigma, St. Louis, Mo.) containing selection medium (DMEM/15% FBS/0.5 ng/mL rIL-6 (Sigma)/10% P388D$_1$ (ATCC, Manassas, Va.) conditioned medium). These fusion cultures were immediately distributed, 2 million cells per plate, into wells of 96 well culture plates (Costar Cat. #3585, VWR). Distributing the culture in 96 well culture plates, immediately following fusion, facilitated selection of a larger diversity of hybridoma clones producing single, specific antibodies. Supernatants from wells were screened by ELISA, for reactivity against Pro108 E. coli expressed protein, Pro108 insect expressed protein, and for no cross-reactivity with the serine protease Pro111 extracellular domain (insect expressed).

Monoclonal cultures, consisting of the genetically uniform progeny from single cells, were established after the screening procedure above, by limiting dilution (Coller, H. and Coller, B. Hybridoma 2: 91-6, 1983), or cell sorting of single viable cells into wells of two 96 well plates (VWR), using flow cytometry (Coulter Elite, Beckman Coulter, Miami, Fla.). The resulting murine B-cell hybridoma cultures were expanded using standard tissue culture techniques. Selected hybridomas were cryopreserved in fetal bovine serum (FBS) with 10% DMSO and stored in Liquid Nitrogen at −196° C. to assure maintenance of viable clone cultures.

Screening & Selection of Antibody Producing Hybridomas

Hybridoma cell lines were selected for production of Pro108 specific antibody by enzyme linked solid phase immunoassay (ELISA). Pro108 or Pro111 proteins were nonspecifically adsorbed to wells of 96 well polystyrene EIA plates (VWR). One hundred uL volumes of Pro108 or Pro111 proteins at approximately 1 ug/mL in (DPBS) were incubated overnight at 4° C. in wells of 96 well polystyrene EIA plates. Plates were washed twice with Tris buffered saline with 0.05% Tween 20, pH 7.4 (TBST). The plate wells were then emptied and nonspecific binding capacity was blocked by completely filling the assay wells with TBST/0.5% bovine serum albumin (TBST/BSA) and incubating for 30 minutes at room temperature (RT). The plate wells were then emptied, 100 uL of hybridoma culture medium samples diluted 1:1 with TBST/BSA was added to the wells and incubated for 1 hour at RT. The wells were then washed 3 times with (TBST). One hundred uL of alkaline phosphatase conjugated goat anti-mouse IgG (Fc) (Pierce Chemical Co., Rockford, Ill.), diluted 1:5000 in TBST/BSA, was then added to each well and incubated for 1 hour at RT. The wells were then washed 3 times with TBST. One hundred uL of alkaline phosphatase substrate para-nitrophenylphosphate (pNPP) (Sigma) at 1 mg/mL in 1 M Diethanolamine buffer pH 8.9 (Pierce, Rockford, Ill.) was then added to each well and incubated for 20 min. at RT. Color development was stopped by addition of 50 uL of 2N NaOH/well. Bound alkaline phosphatase activity was indicated by the development of a visible yellow color. The enzymatic reaction was quantified by measuring the solution's absorbance at 405 nm wavelength. Cultures producing the highest absorbance values were chosen for expansion and further evaluation. Selected ELISA positive cultures from the original 96 well plates were transferred to new 96 well tissue culture plates (VWR).

ELISA Screening of Pro108 MAbs

After 1 week in culture, the 3 A series hybridomas and 59 B series hybridomas specific for Pro108 (negative with Pro111) were retested to confirm continued production of Pro108 specific MAbs. Two of the original three A series (designated A2 and A5) and forty-five of the original 59 B series hybridoma cultures (designated B1 through B45) with supernatants retaining ELISA absorbance values greater than 1.0 with Pro108 and less than 0.2 with Pro111 were expanded in tissue culture and cryopreserved, as described above. Selected Pro108 specific cultures were subcloned by limiting dilution or single cell sorting (Coulter Elite) to ensure genetically stable and uniform progeny.

Results from ELISA Screening of Cloned Pro108 MAbs

The 45 B series hybridomas remaining specific for Pro108 were ranked according to the ELISA results. The clones were tested for reactivity on Pro108 and Pro111. Pro108.B12 had an OD 405 nm of 3.9255 and 0.1018 against Pro108 and Pro111, respectively. Additionally, Pro108.B23 had an OD 405 nm of 3.7632 and 0.0901 against Pro108 and Pro111, respectively. Pro108.B12 received a rank of 2 and Pro108.B23 received a rank of 6.

Based on the ELISA ranking, Pro108.A2, Pro108.A5, Pro108.B10, Pro108.B12, Pro108.B16, Pro108.B23, Pro108.B24, Pro108.B29, Pro108.B30, Pro108.B33, and Pro108.B38 were selected for subcloning. ELISA checker board results (see below) determined that Pro108.A5 paired with Pro108.B12, Pro108.B16, Pro108.B23, Pro108.B24, Pro108.B29, Pro108.B30, Pro108.B33 and Pro108.B38; and that Pro108.B12 and Pro108.B23 paired well; and that Pro108.B12 and Pro108.B10 paired well with each other by sandwich ELISA. The clones obtained from limiting dilution were tested for reactivity on Pro108. Cloned Pro108.B12.1 had an OD 405 nm of 2.8767 and cloned Pro108.B23.1 had an OD 405 nm of 2.6713.

Pro108.A2, Pro108.A5, Pro108.B10, Pro108.B12, Pro108.B16, Pro108.B23, Pro108.B24, Pro108.B29, Pro108.B30, Pro108.B33, and Pro108.B38 MAb clones were scaled up for further characterization by western blot and ELISA.

The isotypes of the B series MAbs were determined using commercially available mouse monoclonal antibody isotyping immunoassay test kits (IsoStrip, Roche Diagnostic Corp., Indianapolis, Ind.). Results of the isotyping are listed in Table 2.

TABLE 2

Pro108 MAb Isotypes

| MAb | Isotype |
| --- | --- |
| Pro108.B12.1 | $IgG_1$ kappa |
| Pro108.B10.1 | $IgG_1$ kappa |

Example 2

Tissue Distribution and Detection of Pro108 in Serum

Reverse Transcription-Polymerase Chain Reaction (RT-PCR)

To detect the presence and tissue distribution of Pro108 Reverse Transcription-Polymerase Chain Reaction (RT-PCR) was performed using cDNA generated from a panel of tissue RNAs. See, e.g., Sambrook et al., *Molecular Cloning: A Laboratory Manual*, 2d ed., Cold Spring Harbor Laboratory Press (1989) and; Kawasaki E S et al., *PNAS* 85(15):5698 (1988). Total RNA was extracted from a variety of tissues or cell lines and first strand cDNA is prepared with reverse transcriptase (RT). Each tissue panel includes 23 cDNAs from five cancer types (lung, ovary, breast, colon, and prostate) and normal samples of testis, placenta and fetal brain. Each cancer set is composed of three cancer cDNAs from different donors and one normal pooled sample. Using a standard enzyme kit from BD Bioscience Clontech (Mountain View, Calif.), Pro108 was detected with sequence-specific primers designed to only amplify Pro108. The PCR reaction was run on the GeneAmp PCR system 9700 (Applied Biosystem, Foster City, Calif.) thermocycler under optimal conditions. One of ordinary skill can design appropriate primers and determine optimal conditions. The amplified product was resolved on an agarose gel to detect a band of equivalent size to the predicted RT-PCR product. A band indicated the presence of Pro108 a sample. FIG. 1A shows the RT-PCR results.

Western Blots

SDS-PAGE was performed according to the method of Laemmli. All samples were reduced with 20 mM DTT in 1×LDS Sample Buffer (Invitrogen) and heated at 70 C for 10 min. 15 ug of each cell lysate and supernatant and 20 and 50 ng recombinant Spondin2 were loaded onto a 4-12% Bis Tris gel (Invitrogen). The gel was transferred gel onto a PVDF membrane (Invitrogen) according to the manufacture's guideline. After blocking with 5% milk in TBST (10 mM Tris pH7.4, 150 mM NaCl, 0.05% Tween20), the membrane was incubate with MAb A5.1, B23.1 or B12.1 (1 ug/ml) for 1 hour at room temperature. After washes with TBST, the blot was incubated with donkey anti-mouse-HRP 1:10,000 (Jackson) for 1 hr at room temperature while shaking. The blot was incubated with ECL Plus developer (Amersham) for 5 min at room temperature and exposed to film for 20 seconds, following manufacture's guidelines.

RT-PCR and Western Blot Results

A comparison of mRNA and protein expression in various cancer cell lines was preformed and is outlined in Table 3 below. For the Western Blot, cells were harvested and lysed in a CHAPS buffer as described above. All lysates were adjusted to a final concentration of 1.2 mg/ml and 15 ul of each lysate was loaded onto the SDS PAGE gel. Recombinant Pro108 (50 ng) was loaded as a positive control.

RT-PCR analysis showed Pro108 mRNA expression in hormone-dependent prostate cancer lines but no indication of Pro108 expression in any other tested cell line. Additionally, the Western Blot results indicate protein expression is in very good agreement with the mRNA expression. Table 3 indicates native Pro108 was detected in the detergent lysate of various cancer cell lines. In the lysate of the androgen-dependent prostate cancer cell line LNCap and MDA PCa2b a band of the predicted molecular weight of Pro108 (35 kD) was detected. The expression of Pro108 is not hormone-dependent as the results with LNCaps plus and minus stimulation with 5-alpha-dihydrotestosterone indicate. No Pro108 was detected in the prostate cancer cell line PC3, the colon cancer line HT29, the breast cancer cell line MDA MB453, the cervical cancer cell line HeLa, the ovarian cancer cell line CaOV3, the lung cancer cell line A549 or 293 cells which were used for transfection. See Table 3 below.

TABLE 3

Comparison of Pro108 mRNA and protein expression in various cancer cell lines

| | LnCAP+ | PC3 | MB453 | HeLa | LnCAP− | A549 | HT29 | 293 | CaOV3 | MDA PCa2b |
|---|---|---|---|---|---|---|---|---|---|---|
| RT-PCR | + | − | − | − | + | − | − | − | − | + |
| Western Blot at ~35 kD | + | − | − | − | + | − | − | − | − | + |

For the western bolts detecting Pro108 in cell lysate and supernatant, 15 ul of cell lysate and cell supernatant (1.2 mg/ml each) was loaded onto a 4-12% SDS Page gel, blotted and developed using 1 ug/ml Pro108.B23 and Pro108.A5, respectively. Recombinant Pro108 (with a 10His-tag) was loaded as a positive control. HeLa cells are negative while LNCap cells are positive for Pro108. Intensity of the Pro108 western blot is indicated in Table 4 below as high intensity (+++), moderate intensity (++), low intensity (+) and no Pro108 detected (−).

As shown in Table 4 below, Pro108 was not only expressed in LNCap cells but was also very efficiently secreted into the medium. For this experiment, LNCap cells were switched to serum-free medium 48 hours prior to harvest the cell supernatant. The total concentration of cell lysate and supernatant was adjusted to 1.2 mg/ml and equal amounts were loaded on the SDS PAGE gel. Pro108 was detected using the Pro108.A5 antibody which has been in used in IHC and the antibody Pro108.B23 which was used as detecting antibody in the sandwich ELISA. The antibody Pro108.B23 reacted with a single band of 35 kD in the LNCap lysate and supernatant. The antibody Pro108.A5 reacted with full length Pro108 and a ~30 kd breakdown product of Pro108 with low intensity (+). Neither antibodies showed reactivity towards any protein in the medium of the RT-PCR-negative cell line HeLa, indicating that both antibodies are very specific.

Detection of Pro108 in Serum Samples by Immunoprecipitation

For the immunoprecipitation experiment the coating antibody of the ELISA was bound to CnBr-Sepharose beads and used to capture Pro108 from serum. Samples used included recombinant Pro108 (rPro108) as a positive control, calf serum, normal human serum (Nrm hum serum), LnCAP supernatant (LnCAP supe), HeLa supernatant (HeLa supe), prostate cancer serum (Pro can serum), lung cancer serum (Lng can), breast cancer serum (Mam can), colon cancer serum (Cln can) and ovarian cancer serum (Ovr can). Anti-Pro108 mAb Pro108.B12.1 was covalently attached to CnBr-Separose beads following the manufacturer's protocol (Amersham Pharmacia). 1 ml of serum was incubated with 100 ul of beads overnight at 4° C. After washing three times with TBS+ Tween20, the bound antigen was eluted using gentle elution buffer pH 3.0 (Pierce). The eluate was reduced to a volume of 50 ul and loaded onto a 4-12% Bis-Tris gel (Invitrogen) as described above. The antibody Pro108.B23, used for detection in the ELISA, was used for the detection on the Western Blot. Intensity of the Pro108 western blot is indicated in Table 5 below as high intensity (+++), moderate intensity (++), low intensity (+) and no Pro108 detected (−).

Results from the Western Blot are summarized in Table 5 below. Immunoprecipitation results show Pro108 can be isolated from serum of healthy individuals as well as from serum of subjects with cancer. The antibody Pro108.B23 reacted with a band of 40 kD in the recombinant Pro108, normal human serum, LnCAP supernatant, prostate cancer serum, lung cancer serum, breast cancer serum, colon cancer serum and ovarian cancer serum samples. Additionally, Pro108.B23 reacted with a dimer product at 80 kD in the prostate, lung, breast, colon and ovarian cancer serum samples. In agreement with the ELISA data below, more Pro108 is present in serum of subjects with cancer than in healthy individuals. Additionally, the over-expression of Pro108 led to increased dimerization of the protein. We tested if the dimeric form of Pro108 is an independent predictor for cancer but found that the dimerization is concentration dependent but not disease dependent.

TABLE 4

Detection of Pro108 in cell lysate and supernatant

| | Recombinant Pro108.His | | Cell Lysate | | | Cell Supernatant | | |
|---|---|---|---|---|---|---|---|---|
| | 50 ng | 20 ng | LnCAP+ | LnCAP− | HeLa | LnCAP+ | LnCAP− | HeLa |
| Pro108.B23 | +++ | ++ | +++ | +++ | − | ++ | +++ | − |
| Pro108.A5 | +++ | ++ | +++ | +++ | − | ++ | +++ | − |

TABLE 5

Immunoprecipitation of Pro108 from normal and cancer serum samples

|  | Normal Samples | | | | Cancer Serum Samples | | | | |
|---|---|---|---|---|---|---|---|---|---|
|  |  | Nrm | | | | | | | |
|  | rPro108 | Calf Serum | hum Serum | LNCaP supe | HeLa supe | Pro can | Lng can | Mam can | Cln can | Ovr can |
| Pro108.B23 | +++ | − | + | + | − | + | ++ | ++ | + | ++ |

Example 3

Sandwich and Checkerboard ELISA of Pro108

High binding polystyrene plates (Corning Life Sciences (MA)) were coated overnight at 4° C. with 8 ug/ml of anti-Pro108 MAb (note: later experiments used 4 ug/ml). The coating solution was aspirated off and free binding sites were blocked with 300μl/well Superblock-TBS (Pierce Biotechnology, Illinois) for 1 hour at room temperature. After washing 4× with TBS+0.1% Tween20, 25 ul (note: later experiments used 20 ul) of antigen was added to each well for 90 minutes incubation. For the checkerboard experiment, each pair was tested on 50 ng/ml and 0 ng/ml of recombinant Pro108-decaHis. For each Sandwich ELISA, a standard curve of 250, 100, 50, 10, 1 and 0 ng/ml Pro108 was run in parallel with the samples. Standard Curve and samples were diluted in Assay Buffer (TBS, 1% BSA, 1% Mouse Serum, 1% Calf Serum, 0.1% Tween20) to a final volume of 100 ul. For the detection, 100 μl Biotinylated MAb (1 μg/ml) were added to each well and incubated for 1 hour at room temperature while shaking. After washing, 100 μl of Alkaline Phosphatase conjugated Streptavidin (Jackson ImmunoResearch Laboratories, PA) was added to each well and incubated for 30 minutes at RT while shaking. After washing, the plate was then developed using pNPP substrate in 1×DEA buffer (Pierce Biotechnology, Illinois) for 30 minutes at RT. The reaction is stopped using 100 μl/well 1N NaOH, and the plate was read at 405 nm using a Spectramax 190 plate reader (Molecular Devices, CA).

Pro108 Checkerboard ELISA

For the checkerboard ELISA, all possible combination of antibodies used as coating and detecting antibody were tested. The pairs B12/B10 and B12/B23 performed best (highest signal/noise ratio) in the Sandwich ELISA and B12/B23 was used in following Sandwich ELISA to analyze native Pro108 in cell lines and serum samples.

The results of the checkerboard ELISA using the Pro108 MAbs are shown in Tables 6A and 6B below. The binding results and epitope map are graphically represented in FIG. 1.

TABLE 6A

Results of Checkerboard Analysis (numbers represent signal/noise ratio)

| coating Mab | detecting Mab | | | | | | | | | |
|---|---|---|---|---|---|---|---|---|---|---|
|  | A5.1 | A2.3 | B12 | B16 | B23 | B24 | B29 | B30 | B33 | control mAb |
| A5.1 | 1 | 1 | 2.44 | 3.1 | 4.1 | 2.3 | 1.4 | 3.8 | 1.7 | 1.1 |
| A2.3 | 1.5 | 1.2 | 4.7 | 7.5 | 17 | 7.5 | 2.8 | 11.2 | 2.3 | 1 |
| B12 | 10 | 4.6 | 1.1 | 1 | 38 | 11 | 1 | 1.2 | 10 | 1 |
| B16 | 14.8 | 7.7 | 1.3 | 1.4 | 24 | 9.9 | 1 | 2.2 | 7.2 | 1 |
| B23 | 11 | 5.3 | 7 | 15.4 | 1 | 1 | 3.7 | 21 | 1 | 1 |
| B24 | 12.7 | 6.3 | 6.5 | 13.7 | 1.8 | 1.1 | 4.1 | 18.5 | 1 | 1 |
| B29 | 17.4 | 9.6 | 1.4 | 1.7 | 30.8 | 9.5 | 1 | 2.8 | 8.2 | 1 |
| B30 | 22 | 11.9 | 1.2 | 1.2 | 41.7 | 17.5 | 1 | 2.6 | 14.4 | 1 |
| B33 | 15 | 8.5 | 14.4 | 30 | 9.4 | 2 | 9.35 | 36 | 1.1 | 1 |
| B39 | 19.7 | 8.5 | 1.7 | 3.5 | 24.7 | 7 | 1.2 | 6 | 6.1 | 1 |

TABLE 6B

Results of Checkerboard Analysis (numbers represent signal/noise ratio)

| coating Mab | Detecting Mab | | | | | | | | | |
|---|---|---|---|---|---|---|---|---|---|---|
|  | B1.1 | B6.1 | B7.1 | B10.1 | B12.1 | B20.1 | B23.1 | B26.1 | B27.1 | A5.1 | control |
| B1.1 | 2.3 | 1.5 | 3.9 | 14.7 | 1.5 | 1.1 | 9.3 | 2.4 | 6.8 | 1.7 | 1.1 |
| B6.1 | 13.2 | 1.0 | 3.2 | 13.0 | 9.3 | 1.0 | 12.0 | 6.6 | 3.8 | 17.6 | 1.0 |
| B7.1 | 10.0 | 1.0 | 1.5 | 3.8 | 4.9 | 1.0 | 5.7 | 1.7 | 1.4 | 13.9 | 1.1 |
| B10.1 | 9.3 | 0.9 | 1.3 | 2.0 | 7.0 | 1.0 | 3.8 | 1.3 | 1.1 | 12.1 | 1.0 |
| B12.1 | 13.1 | 8.5 | 20.6 | 41.3 | 1.3 | 2.6 | 49.9 | 13.7 | 36.9 | 20.7 | 1.0 |
| B20.1 | 10.5 | 1.2 | 3.9 | 10.6 | 7.3 | 1.1 | 11.2 | 5.8 | 3.8 | 6.6 | 1.1 |
| B23.1 | 17.0 | 1.2 | 1.1 | 2.4 | 6.0 | 1.0 | 3.1 | 1.3 | 1.1 | 13.7 | 0.9 |
| B26.1 | 1.6 | 1.0 | 1.4 | 1.5 | 1.5 | 1.1 | 1.4 | 0.8 | 1.3 | 1.4 | 1.0 |
| B27.1 | 10.3 | 0.4 | 1.6 | 4.4 | 3.1 | 1.5 | 5.9 | 1.9 | 1.5 | 10.6 | 0.9 |

Pro108 Checkerboard ELISA

To establish a sensitive Sandwich-ELISA assay, hybridoma clones with a high binding affinity in direct ELISA were selected and antibodies were purified and tested in the checkerboard ELISA. Each antibody was used as a coating as well as a detecting antibody in all possible combinations. During the incubation with detecting antibody, a 10-fold higher concentration of coating antibody was added to the wells to prevent self-pairing. Self-pairing may be observed when antigens are partly multimerized and may confound MAb pairing results. Performing the ELISA assay under competitive conditions ensures that antibodies cannot bind to the same or proximal epitopes even when the antigen is partly aggregated.

Using the described method, antibodies against three distinct epitopes have been identified. Several different combinations of antibody sandwiches were tested to establish an ELISA assay for the detection of native Pro108 in cancer cell lines, transfected cell lines and serum. The pairs B12/B23 and B12/B10 showed the highest sensitivity and specificity. The sensitivity of both B12/B23 and B12/B10 pairs for recombinant Pro108 is 1 ng/ml. The B12/B23 pair did not react with Spondin I or human thrombospondin by ELISA or in Western Blots. The pair B12/B23 reacted positively with lysate and supernatant from transfected 293 cells but not with those from untransfected cells. In good agreement with the Western Blot and RT-PCR results, the ELISA detected Pro108 expressed in LNCap and MDA PCa2b cell lines. The protein was detected in the supernatant of these androgen-dependent cell lines but not in the supernatant of other cells.

To compare the performance of antibody pair B 12/B23 with the B 12/B 10 pair, 160 serum samples (35 of healthy male and female, 25 serum samples each from subjects with colon, breast, ovarian, prostate or lung cancer) were run in parallel with the two assay formats. The inter-assay CV for this sample set was 6% and the data correlated very well (R2-value=0.95) indicating an ELISA with antibody pairs B12/B23 and B12/B10 are comparable to one another.

Example 4

Pro108 and Tumor Marker Assays

Patient Population

A total of 555 (281 males and 274 females) normal serum samples, collected from healthy donors with age ranging from 19 years to 81 years old (median of 54 years) in addition to cancer panels consisting of 1023 subjects with cancer and 997 subjects with related benign diseases were obtained from the following commercial sources: IMPATH-BCP, Inc. (Los Angeles, Calif.), ProMedDx, LLC (Norton, Mass.) and Diagnostic Support Service, Inc., (West Barnstable, Mass.). Additional ovarian cancer samples were obtained from DIAGNOSTIC ONCOLOGY CRO, Inc. (DOCRO). The human serum samples from subjects with stomach cancer were received from University of Pittsburgh, Medical Center. (Seymour, Conn.). All cancer samples were collected prior to treatment, and provided with age, gender, histology and stage information. The benign group included subjects with BPH and prostatitis (n=143) for the prostate cancer analysis; subjects with endometriosis, enlarged ovaries and ovarian cysts (n=146) for the ovarian cancer study; subjects with fibroadenoma, atypical hyperplasia and fibrocystic disease (n=179) for the breast cancer study; subjects with chronic bronchitis, emphysema, asthma, interstitial lung disease and pulmonary hypertension (n=246) in the lung cancer study and subjects with Crohn's disease, diverticulitis, ulcerative colitis and colon polyps (n=283) in the colon cancer study.

Results

The cell line results above indicated that Pro108 is secreted from prostate cancer tissue and possibly from normal prostate and therefore detectable in serum. To test this hypothesis, we screened the sera from healthy subjects and compared the Pro108 concentration with Pro108 values found in subjects with prostate cancer. Since the mRNA profiling also indicated expression in other cancers, we tested also sera of subjects with other forms of cancer as well as subjects with benign diseases. See Table 4 for the summary of all sera samples that were used in our study.

TABLE 7

List of all Serum Samples tested for Pro108 concentration

| Sample Type | Number of Samples |
| --- | --- |
| Normal | 315 (195 Male, 120 Female) |
| Breast Cancer | 235 |
| Breast Benign | 180 |
| Colon Cancer | 125 (56 Male, 69 Female) |
| Colon Benign | 296 (151 Male, 145 Female) |
| Lung Cancer | 298 (210 Male, 88 Female) |
| Lung Benign | 250 (130 Male, 120 Female) |
| Ovarian Cancer | 225 |
| Ovarian Benign | 150 |
| Prostate Cancer | 138 |
| Prostate Benign | 147 |

Pro108 was detected in the sera of female and male subjects with no significant difference between genders. However, the median Pro108 concentration in sera of healthy subjects was significantly lower than the Pro108 concentration of subjects with cancer.

The elevated level of Pro108 in the sera of subjects with cancer confirms the RT-PCR results which showed over-expression of Pro108 in prostate cancer tissue.

FIG. 2 shows Pro108 detection in breast, lung, ovarian, colon and prostate cancer samples in comparison to Pro108 concentration in healthy subjects (female and male). The ELISA plates were coated with 4 ug/ml mAb Pro108.B 12 and after blocking and washing steps, incubated with 20 ul of serum sample. Pro108 was detected with 1 ug/ml biotinylated Pro108.B23 followed by Streptavidin-HRP and pNpp substrate for chromogenic reaction.

In an alternative to the assay described above Pro108.B23 was replaced with Pro108.B10 as the detecting antibody.

Tumor Marker Immunoassays

To compliment and contrast Pro108, Prostate Specific Antigen (PSA), Carcinoembryonic Antigen (CEA), CA15.3, CA19.9 and CA125 levels were measured on the Lumipulse bioanalyzer (Fujirebio, Tokyo, Japan) using commercially available reagents according to the manufacturer's protocol.

Additionally, Regenerative Protein IV (RegIV) levels were measured. PCT application PCT/US2004/016969, which is hereby incorporated by reference in its entirety, discloses the development of mouse monoclonal antibodies (mAbs) to recombinant Reg IV (also know as Cln101) protein and the development of a sequential sandwich ELISA using two Reg IV-specific mAbs. High binding polystyrene plates (Corning Life Sciences (MA) were coated with capture mAb Cln101.A46.1. Twenty uL of serum samples were used in the assay. Calibration was accomplished by using recombinant RegIV standards at concentrations of 10, 5, 1, 0.5, 0.05 and 0 ng/mL. Antigen was detected by biotinylated Cln101.A9.1 mAb, followed by streptavidin-alkaline phosphatase, and pNPP substrate.

Example 5

Detection and ROC Analysis of Pro108 and PSA in Prostate Cancer

The ability of a test to discriminate diseased cases from normal cases is evaluated using Receiver Operating Characteristic (ROC) curve analysis (Metz, 1978; Zweig & Campbell, 1993). ROC curves can also be used to compare the diagnostic performance of two or more laboratory or diagnostic tests (Griner et al., 1981).

ROC curve is generated by plotting sensitivity against specificity for each value. From the plot, the area under the curve (AUC) can be determined. The value for the area under the ROC curve (AUC) can be interpreted as follows: an area of 0.84, for example, means that a randomly selected positive result has a test value larger than that for a randomly chosen negative result 84% of the time (Zweig & Campbell, 1993). When the variable under study can not distinguish between the two result groups, i.e. where there is no difference between the two distributions, the area will be equal to 0.5 (the ROC curve will coincide with the diagonal). When there is a perfect separation of the values of the two groups, i.e. there no overlapping of the distributions, the area under the ROC curve equals 1 (the ROC curve will reach the upper left corner of the plot).

The 95% confidence interval for the area can be used to test the hypothesis that the theoretical area is 0.5. If the confidence interval does not include the 0.5 value, then there is evidence that the laboratory test does have an ability to distinguish between the two groups (Hanley & McNeil, 1982; Zweig & Campbell, 1993).

Detection of Pro1018 in Prostate Cancer

FIG. 3 shows Pro108 detection in subjects with prostate cancer in comparison to healthy subjects (female and male) and subjects with benign prostate diseases (BPH and Prostatitis). The ELISA plates were coated with 8 ug/ml mAb Pro108.B12 and after blocking and washing steps, incubated with 25 ul of serum sample. Pro108 was detected with 1 ug/ml biotinylated mAb Pro108.B23 followed by Streptavidin-HRP and pNpp substrate for chromogenic reaction.

ROC Analysis of Pro108 Alone and in Combination in Prostate Cancer

Analysis of Pro108, Reg IV and PSA levels in blood serum was preformed on normal males, men with prostate benign disease (BPH and prostatitis), and subjects with prostate cancer. The data were analyzed by Receiver Operating Characteristic (ROC) curves to determine and compare the sensitivity and specificity of each marker in detecting cancer as described above. The analyses showed that the levels of Reg IV and Pro108 are elevated in serum samples from subjects with prostate cancer compared to normal control, BPH, and prostatitis samples.

Area Under the Curve (AUC) values from ROC analysis of prostate cancer versus normal and benign samples showed that RegIV and Pro108 have sensitivities and specificities that are comparable to PSA in detecting prostate cancer. Interestingly, in the PSA "grey zone" of 4-10 ng/mL, Pro108 showed significantly higher sensitivity and specificity in detecting prostate cancer than PSA. Furthermore, the increased sensitivity and specificity of RegIV and Pro108 over PSA were even more dramatic in the 2-4 ng/mL PSA range, where RegIV and Pro108 were able to stratify 57% and 33% of prostate cancer samples, respectively, with 90% specificity. Application of multiple markers in "synergistic effect" analyses showed slight improvement in AUC, where the combination of all three markers in the PSA 2-4 ng/mL range showed an AUC=0.823. Tables 8-10 demonstrate various ROC analyses of Pro108 alone or in combination with other markers in prostate cancer. Tables 11-12 demonstrate results from ROC analyses of synergistic effects of Pro108 with other markers in a PSA range of 4-10 ng/ml and 2-4 ng/ml, respectively.

TABLE 8

ROC analysis for Pro108 for differentiation of normal males and males with benign conditions from males with prostate cancer

| Statistic | Pro108 Original N = 406 | Pro108 Current N = 431 |
|---|---|---|
| AUC (95% CI) | 0.681 (0.633-0.726) | 0.701 (0.656-0.744) |
| Cutoff for best combination of Sens/Spec. | 49.2 | 49.2 |
| Sens./Spec. at best cutoff | 61%/74% | 63%/74% |
| Sens. @ 90% Spec. (Cutoff) | 34% | 35% |
| p-value vs. PSA ROC | 0.021 (PSA ROC is higher [0.765]) | Not applicable due to nonequivalent N |

TABLE 9

ROC analysis for Pro108 for differentiation of normal males from males with prostate cancer

| Statistic | Pro108 Original N = 259 | Pro108 Current N = 284 |
|---|---|---|
| AUC (95% CI) | 0.767 (0.711-0.817) | 0.787 (0.734-0.833) |
| Cutoff for best combination of Sens/Spec. | 47.0 | 47.0 |
| Sens./Spec. at best cutoff | 63%/83% | 65%/83% |
| Sens. @ 90% Spec. (Cutoff) | 45% | 45% |
| p-value vs. PSA ROC | 0.292 | Not applicable due to nonequivalent N |

TABLE 10

Logistic regression for differentiation of normal males and males with benign conditions from males with prostate cancer for Pro108, RegIV and PSA.

| Statistics | PSA | RegIV | Pro108 | RegIV + PSA | Pro108 + RegIV | Pro108 + PSA |
|---|---|---|---|---|---|---|
| ROC AUC | 0.762 | 0.741 | 0.686 | 0.800 | 0.768 | 0.814 |
| Sens. @ 90% Spec. | 31% | 36% | 34% | 44% | 37% | 46$ |
| Spec. @ 90% Sens. | 44% | 44% | 20% | 47% | 46% | 55% |

TABLE 11

Analysis of synergistic effects in PSA range of 4-10 ng/ml. Logistic regression for differentiation of normal males and males with benign conditions from males with prostate cancer for Pro108, RegIV and PSA.

| Statistics | PSA | RegIV | Pro108 | RegIV + PSA | Pro108 + RegIV | Pro108 + PSA | Pro108 + RegIV + PSA |
|---|---|---|---|---|---|---|---|
| ROC AUC | 0.522 | 0.657 | 0.652 | 0.657 | 0.698 | 0.657 | 0.699 |
| Sens. @ 90% Spec. | 5% | 25% | 33% | 25% | 35% | 33% | 42% |
| Spec. @ 90% Sens. | 10% | 36% | 14% | 36% | 38% | 18% | 35% |

TABLE 12

Analysis of synergistic effects in PSA range of 2-4 ng/ml. Logistic regression for differentiation of normal males and males with benign conditions from males with prostate cancer for Pro108, RegIV and PSA.

| Statistics | PSA | RegIV | Pro108 | RegIV + PSA | Pro108 + RegIV | Pro108 + PSA | Pro108 + RegIV + PSA |
|---|---|---|---|---|---|---|---|
| ROC AUC | 0.500 | 0.733 | 0.812 | 0.733 | 0.823 | 0.811 | 0.823 |
| Sens. @ 90% Spec. | 2% | 57% | 33% | 52% | 33% | 33% | 33% |
| Spec. @ 90% Sens. | 10% | 40% | 66% | 42% | 67% | 65% | 67% |

From the statistical analysis can be concluded that Pro108 adds sensitivity and specificity to PSA, and can detect cancers missed by PSA. Additionally, RegIV also adds sensitivity and specificity to PSA, and can help detect cancers missed by PSA. Pro108 and RegIV especially increase the detection rate of prostate cancer in the PSA "grey zone", both 2-4 ng/mL and 4-10 ng/mL.

The combinations of Pro108, RegIV and PSA are not significantly better than Pro108 alone in the PSA range of 2-4 ng/ml but in the PSA range of 4-10 ng/ml the combinations of Pro108 and RegIV may improve detection of cancer. Both, Pro108 and RegIV have potential clinical applications in the PSA 2-4 ng/mL and 4-10 ng/ml range.

Example 6

Detection and ROC Analysis of Pro108 and CA125 in Ovarian Cancer

The ability of Pro108 to detect and discriminate ovarian cancer from normal samples and benign ovarian diseases was evaluated using Receiver Operating Characteristic (ROC) curve analysis as described above.
Detection of Pro108 in Ovarian Cancer FIG. 4 shows Pro108 detection in subjects with ovarian cancer in comparison to subjects with benign ovarian diseases (polycystic ovaries, endometriosis or enlarged ovaries=Edema) and healthy subjects (male and female). For the ELISA, plates were coated with 4 ug/ml mAb Pro108.B12 and after blocking and washing steps, incubated with 10 ul of serum sample. Pro108 was detected with 1 ug/ml biotinylated Pro108.B23 followed by Streptavidin-HRP and pNpp substrate for chromogenic reaction.

FIG. 5 shows Pro108 detection in subjects with various forms of ovarian cancer. The median values are compared to median Pro108 values of subjects with endometriosis and to values of healthy women. The ELISA plates were coated with 4 ug/ml mAb Pro108.B12 and after blocking and washing steps, incubated with 10 ul of serum sample. Pro108 was detected with 1 ug/ml biotinylated Pro108.B23 followed by Streptavidin-HRP and pNpp substrate for chromogenic reaction.

The Pro108 concentration in serum from subjects with ovarian cancer was elevated when compared with Pro108 values in healthy women and women with benign ovarian diseases. The median Pro108 concentration was nearly two-fold higher in women with ovarian cancer (54.1 ng/ml) than in healthy women (29.8 ng/ml). Interestingly, the Pro108 serum concentration was elevated in all tested ovarian cancer types. The median Pro108 concentration in serous cancer patients was comparable to values in patients with mucinous cancer. This of special interest since the currently used marker CA125 is up-regulated only in serous cancer. In addition, CA125 can also be elevated in patients with benign conditions as endometriosis, benign ovarian cysts, uterine fibroids, pregnancy, or pelvic inflammatory disease while Pro108 seemed to be present in normal concentration in women with benign ovarian diseases. These results show that Pro108 was detectable in all ovarian cancer patients and distinguish healthy individuals from cancer patients, demonstrating it's usefulness as a ovarian cancer marker.
ROC Analysis of Pro108 Alone and in Combination in Ovarian Cancer Analysis of Pro108 and CA125 levels in blood serum was preformed on normal females, women with benign ovarian disease (endometriosis), and subjects with ovarian cancer. The data were analyzed by Receiver Operating Characteristic (ROC) curves to determine and compare the sensitivity and specificity of each marker in detecting cancer as described above. The analyses showed that the levels Pro108 are elevated in serum samples from subjects with ovarian cancer compared to normal control and benign disease samples.

Area Under the Curve (AUC) values from ROC analysis of ovarian cancer versus normal and benign samples showed that Pro108 sensitivity and specificity is comparable to CA125 in detecting ovarian cancer. Furthermore, the increased sensitivity and specificity of Pro108 over CA125 was even more dramatic in the CA125 negative (<30 U/mL) range, where Pro108 was able to stratify 26% of ovarian cancer samples, with 90% specificity. Application of multiple markers in "synergistic effect" analyses showed improvement in AUC, where the combination of Pro108 and CA125 markers in stage 1 and 2 ovarian cancer showed an AUC=0.837. Tables 13-14 demonstrate various ROC analyses of Pro108 alone or in combination with other markers in ovarian cancer. Table 15 demonstrate results from ROC analyses of the ability to detect cancers that are CA125 negative (<30 U/mL).

TABLE 13

ROC analysis of Pro108 and CA125 to differentiate alone or synergistically normal (n = 31) or benign disease (endometriosis n = 24) subjects from subjects with ovarian cancer (n = 57). (normal + benign disease vs. cancer)

| Statistic | Pro108 | CA125 | Pro108 + CA125 |
|---|---|---|---|
| ROC AUC | 0.659 | 0.772 | 0.816 |
| Sens. @ 90% Spec. | 33% | 67% | 61% |
| Spec. @ 90% Sens. | 8% | 4% | 27% |

TABLE 14

ROC analysis of Pro108 and CA125 to differentiate alone or synergistically normal (n = 31) or benign disease (endometriosis n = 24) subjects from subjects with stage 1 and stage 2 ovarian cancer (n = 28). (normal + benign disease vs. cancer)

| Statistic | Pro108 | CA125 | Pro108 + CA125 |
|---|---|---|---|
| ROC AUC | 0.754 | 0.696 | 0.837 |
| Sens. @ 90% Spec. | 32% | 61% | 64% |
| Spec. @ 90% Sens. | 40% | 4% | 38% |

TABLE 15

ROC analysis of Pro108 to differentiate normal (n = 31) or benign disease (endometriosis n = 16) subjects from subjects with CA125 negative (<30 U/mL) ovarian cancer (n = 19). (normal + benign disease vs. cancer)

| Statistic | Pro108 |
|---|---|
| ROC AUC | 0.61 |
| Sens. @ 90% Spec. | 26% |
| Spec. @ 90% Sens. | 0% |

ROC analysis results for Pro108 in ovarian cancer are at least equal to or better compared to known marker CA125. Pro108 AUC scores are good in subjects with Stage 1 & 2 ovarian cancer. Additionally, Pro108 AUC scores are high even in CA125<30 U/ml. Multivariate (Pro108+CA125) analysis indicates that the use of CA125 and Pro108 in combination improves sensitivity and specificity.

To confirm the performance of Pro108 as a diagnostic for ovarian cancer, Pro108 and CA125 and CEA were measured in a second study using a different sample set from Johns Hopkins (Baltimore, Md.). The study consisted of healthy women (n=50), individuals with benign endometrial and ovarian disease (n=45) and subjects with ovarian cancer (n=50). The ROC analysis (cancer versus normal+benign) resulted in an AUC=0.81 for Pro108 while the AUC for CA125 in this study was 0.89. The combination of Pro108+CA125 improved sensitivity and specificity even further (AUC=0.91).

Pro108 is useful as an early stage ovarian cancer diagnostic. Only 25% of all ovarian cancer is found in stage 1. If ovarian cancer is found in stage 1 surgery is very effective and the 5-year survival rate is 90%.

Example 7

Detection and ROC Analysis of Pro108, CEA and CA19.9 in Colon Cancer

Detection of Pro108 in Colon Cancer

FIG. 6 shows Pro108 detection in the serum of subjects with colon cancer, Crohn's diseases, Diverticulitis, Ulcerative Colitis, colon polyps, in comparison to Pro108 in serum of healthy individuals. The median values are compared to median Pro108 values of healthy individuals (male and female). The ELISA plates were coated with 4 ug/ml mAb Pro108.B12 and after blocking and washing steps, incubated with 10 ul of serum sample. Pro108 was detected with 1 ug/ml biotinylated Pro108.B23 followed by Streptavidin-HRP and pNpp substrate for chromogenic reaction.

ROC Analysis of Pro108 Alone and in Combination in Colon Cancer

Analysis of Pro108, CEA and CA19.9 levels in blood serum was preformed on normal subjects, subjects with benign colon disease (Crohn's diseases, Diverticulitis, etc.), and subjects with colon cancer. The data were analyzed by Receiver Operating Characteristic (ROC) curves to determine and compare the sensitivity and specificity of each marker in detecting cancer as described above. The analyses showed that the levels Pro108 are elevated in serum samples from subjects with colon cancer compared to normal control and benign disease samples.

Area Under the Curve (AUC) values from ROC analysis of colon cancer versus normal and benign samples showed that Pro108 sensitivity and specificity is at least comparable to CEA and CA19.9 in detecting colon cancer. Furthermore, the sensitivity and specificity of Pro108 compared to CEA and CA19.9 was even more dramatic in the stage 1 and stage 2 cancer sample set. Tables 16-17 demonstrate various ROC analyses of Pro108 alone or in combination with other markers in colon cancer.

TABLE 16

ROC analysis of Pro108, CEA and CA19.9 to differentiate normal or benign disease (n = 833) subjects from subjects with colon cancer (n = 142). (normal + benign disease vs. cancer)

| Statistic | Pro108 | CEA | CA19.9 |
|---|---|---|---|
| ROC AUC | 0.77 | 0.65 | 0.58 |
| Sens. @ 90% Spec. | 33% | 17% | 67% |
| Spec. @ 90% Sens. | 8% | 25% | 4% |

To confirm the performance of Pro108 as a diagnostic for colon cancer, Pro108, CA19.9 and CEA were measured in a second study using a different sample set from Johns Hopkins (Baltimore, Md.). The study consisted of healthy individuals (n=99), individuals with benign colon diseases (n=22) and subjects with colon cancer (n=49). The ROC analysis (cancer versus normal+benign) resulted in an AUC=0.78 for Pro108 while the AUC for CA19.9 and CEA in this study were 0.7 and 0.8, respectively.

TABLE 17

ROC analysis of Pro108, CEA and CA19.9 to differentiate normal (n = 99) or benign disease (n = 22) subjects from subjects with colon cancer (n = 49) or from subjects with stage 1 or 2 colon cancer (n = 25). (normal + benign disease vs. cancer)

| Statistic | Sample Set | Pro108 | CEA | CA19.9 |
|---|---|---|---|---|
| ROC AUC | All stages | 0.78 | 0.8 | 0.7 |
| | Stage I + II | 0.65 | 0.7 | 0.58 |

ROC analysis results for Pro108 in colon cancer are at least equal to or better compared to known markers CEA and CA19.9. Pro108 AUC scores are good in subjects with Stage 1 & 2 colon cancer. It is contemplated that multivariate use of Pro108, CEA and/or CA19.9 in combination improves sensitivity and specificity for detection of colon cancer.

Pro108 is useful as an early stage colon cancer diagnostic. It is well known that if colon cancer is found in stage 1 surgery is very effective and the 5-year survival rate increases dramatically.

Example 8

Detection of Pro108 in Stomach Cancer

FIG. 7 shows Pro108 detection in stomach cancer and prostate cancer samples. The median values are compared to median Pro108 values of healthy individuals (male and female). The ELISA plates were coated with 4 ug/ml mAb B 12 and after blocking and washing steps, incubated with 10 ul of serum sample. Pro108 was detected with 1 ug/ml biotinylated Pro108.B23 followed by Streptavidin-HRP and pNpp substrate for chromogenic reaction. The median Pro108 level in subjects with stomach cancer was 3.4 times higher than in healthy individuals. The sensitivity to detect stomach cancer at 95% specificity was 82% in this sample set.

Example 9

Multivariate ROC Analysis of Pro108 and Known Cancer Markers in Various Cancers In addition to increasing sensitivity and specificity for detecting the cancers shown above, ROC analysis, as described above, indicated Pro108 increases sensitivity and specificity for detection of breast and lung cancer alone or in combination with known markers. Detection of Pro108 and other markers was performed as described above. Table 18 below summarizes Receiver Operating Characteristic (ROC) curve analysis for Pro108 alone in a combination with traditional markers for each cancer type. AUC scores are reported for Pro108, each traditional marker and multivariate analysis of Pro108 and a traditional marker.

TABLE 18

Multivariate ROC analysis with Pro108 and traditional markers in various cancers.

| Cancer | Pro108 AUC | Traditional Marker AUC | Multivariate AUC |
|---|---|---|---|
| Breast | 0.62 | 0.58 (CEA) | 0.63 (P108 + CEA) |
| | | 0.6 (CA15.3) | 0.64 (P108 + CA15.3) |
| Colon | 0.77 | 0.65 (CEA) | 0.78 (P108 + CEA) |
| | | 0.58 (CA19.9) | 0.78 (P108 + CA19.9) |
| Lung | 0.69 | 0.61 (CEA) | 0.71 (P108 + CEA) |
| Ovary | 0.72 | 0.48 (CEA) | 0.72 (P108 + CEA) |
| | | 0.81 (CA125) | 0.82 (P108 + CA125) |
| Prostate | 0.73 | 0.78 (PSA) | 0.86 (P108 + PSA) |
| | | 0.7 (% F/T PSA)* | |

*(% F/T PSA) indicates the Percent Free/Total PSA assay.

Example 10

Detection of Pro108 in Tissue by ELISA and IHC

Immunohistochemical (IHC) Staining

Formalin-fixed, paraffin-embedded tissue blocks were sectioned to 5 μm and mounted on charged glass slides (Superfrost Plus, Fisher Scientific, Pittsburgh, Pa.). Endogenous peroxidase activity was blocked with 3.0% hydrogen peroxide for 15 minutes. Antigen retrieval was performed in a citrate buffer (20 mmol/L, pH 6.0) at 120° C. for 10 minutes. Staining was conducted on a DAKO autostainer (DakoCytomation, Carpinteria, Calif.) using an indirect avidin-biotin immunoperoxidase method (Vector Labs, Burlingame, Calif.). Sections were incubated at 25° C. for 60 minutes with the Pro108.B23.1 antibody (1 μg/ml). Negative controls were run on all sections at 1 μg/ml of a subclass-matched $IgG_1$ gamma (BD PharMingen, San Diego, Calif.), generated against unrelated antigens. Pro108 staining was visualized using 3,3'-diaminobenzidine (DakoCytomation, Carpinteria, Calif.). Specificity of Pro108 staining was confirmed by a blocking experiment with preincubation of the Pro108.B23.1 antibody with the full-length Pro108 protein (8 ng/ml) at 25° C. for 60 minutes, prior to immunohistochemical processing.

Results

The ELISA assay described above was used to test cytosolic detergent extracts from somatic tissue and cancer tissue. Results are presented in FIG. 8. Pro108 protein was found in low amounts in several tissues including lung, muscles, small intestines, adrenal and pituitary gland and lymph nodes. These results are in good agreement with data from our mRNA profiling as well as with published northern blot experiments (Manda et al., 1999). The highest amount of Pro108 was found in normal prostate tissue and in cancer tissue. The highest amount of Pro108 (up to 200 ng/mg total protein) was consistently found in prostate cancer tissue. Since Pro108 can be readily detected in sera of healthy female and male persons with no significant difference between genders, the normal level of Pro108 in blood must result from expression in normal somatic tissues other than prostate. This indicates that the high detectable Pro108 concentration in normal prostate tissue may not reflect high protein expression but low secretion efficiency.

The results from the ELISA of tissue extracts were confirmed by IHC experiments. Pro108 was detected in prostate cancer and other cancer but not in most of the normal somatic tissues. In prostate cancer, the Pro108 staining intensity and the percentage of positive tissue increased with tumor grade. In addition, a significant Pro108 staining in prostate cancer tissue indicated a higher relative risk of capsular extension while organ confined tumors showed less significant staining. These results show that Pro108 is useful as diagnostic, staging and prognostic marker in cancer.

Table 19 below summarize IHC staining results for Pro108 in various cancer stages (Gleason Score) and assigns an Index Score for each group based on the intensity of staining and percent of the tissue that was stained. The increase in the Index Score with progression of the cancer Gleanson Score indicates that Pro108 is useful in staging cancer and monitoring progression of cancers. Pro108 is contemplated to be useful as a marker for determining response to a therapy, where a decrease in Pro108 levels is indicative of a reduction of the Gleason Score and effectiveness of the therapy. The target of therapy may be Pro108 or Pro108 may serve as a surrogate marker for various other therapies.

TABLE 19

Summary of IHC staining in Cancer Tissues by Gleason Sum.

| Gleason Score | n | # No Stain (% No stain) | # + Stain (% +) | # ++ Stain (% ++) | # +++ Stain (% +++) | Avg. staining | Avg. % of Ca tissue stained | Index Score* |
|---|---|---|---|---|---|---|---|---|
| 2-4 | 7 | 2 (29) | 2 (29) | 3 (43) | 0 (0) | 1.14 (+) | 38% | 2.7 |
| 5-6 | 88 | 23 (26) | 29 (33) | 30 (34) | 6 (7) | 1.22 (+) | 34.11% | 2.59 (s.d. 1.84) |
| 7-10 | 60 | 7 (12) | 7 (12) | 19 (32) | 27 (45) | 2.12 (+) | 61.92% | 4.27 (s.d. 2.00) |

Predominant stain intensity used for calculations
*Index Score - Composite of tissue staining intensity and % of tissue stained
Score awarded as follows:
+ Stain 1
++ Stain 2
+++ Stain 3
0% of Tissue Stained 0
1-33% of Tissue Stained 1
34-66% of Tissue Stained 2
67-100% of Tissue Stained 3

Table 20 summarizes Pro108 IHC staining in prostate cancers with capsular extension or that are organ confined. Capsular extension in prostate cancer is common indicator of poor prognosis for the disease. Significant staining is defined as ++ or greater staining intensity and greater than 20% of cells are stained. The results below indicate that capsular extension samples showed more significant staining than organ confined samples and more capsular extension samples showed significant staining than not. Furthermore, there is a 1.676 relative risk of capsular extension if significant staining is present in a sample (two-tailed p value=0.002). These results indicate that Pro108 is useful as a prognostic indicator of severity and potentially outcome of prostate cancer.

TABLE 20

Comparison of capsular extension vs. organ confined Pro108 staining in prostate cancer.

| | Capsular Extension Samples | Organ Confined Samples | Total |
|---|---|---|---|
| Significant Staining | 44 | 19 | 63 |
| No Significant Staining | 25 | 35 | 60 |
| Total | 69 | 54 | 123 |

Table 21 summarizes Pro108 IHC staining various cancer and normal somatic tissues. The results indicate that Pro108 is detected in pancreatic, colon, urinary bladder and gastric cancer tissues. No Pro108 was detected in the kidney or lung cancer tissues. Pro108 was not detected in the majority of normal somatic tissues, but was present in samples of adrenal gland and Ileum. These results are in agreement with results above that Pro108 expression is limited in normal tissues and is elevated in cancerous tissues as well as serum in subjects with cancer.

TABLE 21

Pro108 expression in various cancer types and normal somatic tissue.

| | N samples with positive staining | % samples with positive staining |
|---|---|---|
| Cancer Tissues | | |
| Pancreatic Cancer | 5/5 | 100 |
| Colon Cancer | 4/5 | 80 |
| Urinary Bladder Cancer | 2/3 | 67 |
| Gastric Cancer | 1/5 | 20 |
| Kidney Cancer | 0/5 | 0 |
| Lung Cancer | 0/9 | 0 |
| Normal Somatic Tissues | | |
| Adrenal Gland | 1/1 | 100 |
| Bone Marrow | 0/1 | 0 |
| Colon | 0/1 | 0 |
| Esophagus | 0/1 | 0 |
| Gallbladder | 0/1 | 0 |
| Heart | 0/1 | 0 |
| Ileum | 1/1 | 100 |
| Kidney | 0/1 | 0 |
| Liver | 0/1 | 0 |
| Lung | 0/1 | 0 |
| Pancreas | 1/1 | 100 |
| Peritoneum | 0/1 | 0 |
| Spleen | 0/1 | 0 |
| Stomach | 0/1 | 0 |
| Thymus | 0/1 | 0 |
| Thyroid | 0/1 | 0 |
| Urinary Bladder | 0/1 | 0 |

Example 11
Deposits

Deposit of Cell Lines and DNA

Hybridoma cell lines were deposited with the American Type Culture Collection (ATCC) located at 10801 University Boulevard, Manassas, Va. 20110-2209, U.S.A., and accorded accession numbers.

The following hybridoma cell lines were deposited with ATCC, Pro108.B10.1 and Pro108.B12.1. The names of the deposited hybridoma cell lines above may be shortened for convenience of reference. E.g. A01.1 corresponds to Pro108.A01.1. These hybridomas correspond to the clones (with their full names) deposited with the ATCC. Table 22 lists the hybridoma clone deposited with the ATCC, the accorded ATCC accession number, and the date of deposit.

TABLE 22

ATCC deposits

| Hybridoma | ATCC Accession No. | Deposit Date |
| --- | --- | --- |
| Pro108.B10.1 | PTA-5885 | 23 Mar. 2004 |
| Pro108.B12.1 | PTA-5886 | 23 Mar. 2004 |

These deposits were made under the provisions of the Budapest Treaty on the International Recognition of the Deposit of Microorganisms for the Purpose of Patent Procedure and the Regulations there under (Budapest Treaty). This assures maintenance of viable cultures for 30 years from the date of deposit. The organisms will be made available by ATCC under the terms of the Budapest Treaty, and subject to an agreement between diaDexus, Inc. and ATCC, which assures permanent and unrestricted availability of the progeny of the cultures to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the cultures on deposit should die or be lost or destroyed when cultivated under suitable conditions, they will be promptly replaced on notification with a viable specimen of the same culture. Availability of the deposited strains are not to be construed as a license to practice the invention in contravention of the rights granted under the authority of any government in accordance with its patent laws. The making of these deposits is by no means an admission that deposits are required to enable the invention

We claim:

1. A method for assessing risk of ovarian, colon, lung, breast, prostate or stomach cancer in a patient which comprises measuring levels of Pro108 and CA15.3 or Regenerating Protein IV (RegIV) in a sample obtained from the patient to assess the risk of ovarian, colon, lung, breast, prostate or stomach cancer in the patient wherein Pro108 comprises residues 1-331 of SEQ ID NO:1 or SEQ ID NO:2,
wherein an elevated level of Pro108 as compared to a control is indicative of heightened risk for ovarian, colon, lung, breast, prostate or stomach cancer.

2. The method of claim 1 wherein the cancer is selected from the group consisting of ovarian, colon, breast and stomach cancer.

3. The method of claim 1 wherein the cancer is ovarian or colon cancer.

4. The method of claim 1 wherein Pro108 is measured with an antibody selected from:
(i) an isolated antibody or antigen binding fragment specific for Pro108 produced by a hybridoma selected from the group consisting of ATCC Accession Number PTA-5885 and PTA-5886; or
(ii) an isolated antibody or antigen binding fragment which competes for binding to the same epitope of Pro108 recognized by the antibody produced by a hybridoma selected from the group consisting of ATCC Accession Number PTA-5885 and PTA-5886.

5. The method of claim 4, wherein the antibody that competes for binding to the same epitope is a monoclonal antibody, humanized antibody or human antibody.

6. The method of claim 4 wherein the antibody is a labeled antibody.

7. The method of claim 1 wherein the levels of Pro108 and CA15.3 or RegIV are measured in a sample from said patient selected from the group consisting of cells, tissues, blood, serum, plasma, urine, stool, salvia and sputum.

8. The method of claim 1 wherein the levels of Pro108 and CA15.3 are measured to assess the risk of cancer in the patient.

9. The method of claim 1 wherein the levels of Pro108 and RegIV are measured to assess the risk of cancer in the patient.

10. A method for determining if cells in a sample express Pro108 comprising
(a) contacting a sample of cells with a Pro108 antibody under conditions suitable for specific binding of the Pro108 antibody to Pro108 and
(b) determining the level of binding of the antibody to cells in the sample, or the level of Pro108 antibody internalization by cells in said sample,
wherein the Pro108 antibody is selected from:
(i) an isolated antibody or antigen binding fragment specific for Pro108 produced by a hybridoma selected from the group consisting of ATCC Accession Number PTA-5885 and PTA-5886; or
(ii) an isolated antibody or antigen binding fragment which competes for binding to the same epitope of Pro108 recognized by the antibody produced by a hybridoma selected from the group consisting of ATCC Accession Number PTA-5885 and PTA-5886; and
wherein Pro108 antibody binding to cells in the sample or internalization of the Pro108 antibody by cells in the sample indicate cells in the sample express Pro108.

11. The method of claim 10, wherein the antibody that competes for binding to the same epitope is a monoclonal antibody, humanized antibody or human antibody.

12. The method of claim 10 wherein said sample of cells is from a subject who has a cancer, is suspected of having a cancer or who may have a predisposition for developing cancer.

13. The method of claim 12 wherein the cancer is prostate, ovarian, colon, breast or stomach cancer.

14. The method of claim 10 wherein said antibody is a labeled antibody.

15. A method for monitoring a Pro108-expressing cancer in a subject in need thereof comprising,
(a) measuring Pro108 levels over time in a sample from a subject with a Pro108 antibody under conditions suitable for specific binding of the Pro108 antibody to Pro108 in said sample, and
(b) comparing Pro108 levels determined over time to a baseline or normal control,
wherein the Pro108 antibody is selected from:
(i) an isolated antibody or antigen binding fragment specific for Pro108 produced by a hybridoma selected from the group consisting of ATCC Accession Number PTA-5885 and PTA-5886; or
(ii) an isolated antibody or antigen binding fragment which competes for binding to the same epitope of Pro108 recognized by the antibody produced by a hybridoma selected from the group consisting of ATCC Accession Number PTA-5885 and PTA-5886; and
wherein an increase in Pro108 binding over time is indicative of progression of cancer and a decrease in Pro108 binding over time is indicative of regression of cancer.

16. The method of claim 15 wherein the antibody that competes for binding to the same epitope is a polyclonal antibody, monoclonal antibody, humanized antibody or human antibody.

17. The method of claim 15 wherein said sample is selected from the group consisting of cells, tissues, blood, serum, plasma, urine, stool, salvia and sputum.

18. The method of claim 15 wherein the cancer is prostate, ovarian, colon, breast or stomach cancer.

19. The method of claim 15 wherein said antibody is a labeled antibody.

20. A method for detecting Pro108 overexpression in a test cell sample, comprising:
(a) combining a test cell sample with a Pro108 antibody under conditions suitable for specific binding of Pro108 to Pro108 expressed by cells in said test sample
(b) determining the level of binding of the Pro108 antibody to the cells in the test sample, and
(c) comparing the level of Pro108 antibody bound to the cells in step (b) to the level of Pro108 antibody binding to cells in a control cell sample,
wherein the Pro108 antibody is selected from:
(i) an isolated antibody or antigen binding fragment specific for Pro108 produced by a hybridoma selected from the group consisting of ATCC Accession Number PTA-5885 and PTA-5886; or
(ii) an isolated antibody or antigen binding fragment which competes for binding to the same epitope of Pro108 recognized by the antibody produced by a hybridoma selected from the group consisting of ATCC Accession Number PTA-5885 and PTA-5886; and
wherein an increase in the binding of the Pro108 antibody in the test cell sample as compared to the control is indicative of Pro108 overexpression by cells in the test cell sample.

21. The method of claim 20 wherein the test cell sample is a cancer cell sample.

22. The method of claim 21 wherein the cancer cell sample is of a prostate, ovarian, colon, breast or stomach cancer.

23. The method of claim 22 wherein the ovarian cancer is a serous or mucinous adenocarcinoma or metastatic cancer.

24. The method of claim 20 wherein the control is a sample of adjacent normal tissue.

25. The method of claim 20, wherein the antibody that competes for binding to the same epitope is a monoclonal antibody, humanized antibody or human antibody.

26. The method of claim 20 wherein said antibody is a labeled antibody.

27. A method for detecting Pro108 overexpression in a subject in need thereof comprising,
(a) combining a sample of a subject with a Pro108 antibody under conditions suitable for specific binding of the Pro108 antibody to Pro108 in said sample
(b) determining the level of Pro108 in the sample, and
(c) comparing the level of Pro108 determined in step (b) to the level of Pro108 in a control,
wherein the Pro108 antibody is selected from:
(i) an isolated antibody or antigen binding fragment specific for Pro108 produced by a hybridoma selected from the group consisting of ATCC Accession Number PTA-5885 and PTA-5886; or
(ii) an isolated antibody or antigen binding fragment which competes for binding to the same epitope of Pro108 recognized by the antibody produced by a hybridoma selected from the group consisting of ATCC Accession Number PTA-5885 and PTA-5886; and
wherein an increase in the level of Pro108 in the sample from the subject as compared to the control is indicative of Pro108 overexpression in the subject.

28. The method of claim 27 wherein the subject has cancer.

29. The method of claim 28 wherein the subject has prostate, ovarian, colon, breast or stomach cancer.

30. The method of claim 29 wherein the ovarian cancer is a serous or mucinous adenocarcinoma or metastatic cancer.

31. The method of claim 27 wherein the control is a serum sample from a subject without a cancer overexpressing Pro108.

32. The method of claim 27 wherein said sample is selected from the group consisting of cells, tissues, blood, serum, plasma, urine, stool, salvia and sputum.

33. The method of claim 27, wherein the antibody that competes for binding to the same epitope is a monoclonal antibody, humanized antibody or human antibody.

34. The method of claim 27 wherein said antibody is a labeled antibody.

35. A method for assessing risk of prostate cancer in a patient which comprises measuring levels of Pro108 and Prostate Specific Antigen (PSA) in a sample obtained from the patient to assess the risk of prostate cancer in the patient wherein Pro108 is measured with an antibody selected from:
(i) an isolated antibody or antigen binding fragment specific for Pro108 produced by a hybridoma selected from the group consisting of ATCC Accession Number PTA-5885 and PTA-5886; or
(ii) an isolated antibody or antigen binding fragment which competes for binding to the same epitope of Pro108 recognized by the antibody produced by a hybridoma selected from the group consisting of ATCC Accession Number PTA-5885 and PTA-5886, and
wherein an elevated level of Pro108 as compared to a control is indicative of heightened risk of prostate cancer.

36. The method of claim 35, wherein the antibody that competes for binding to the same epitope is a monoclonal antibody, humanized antibody or human antibody.

37. The method of claim 35 wherein the antibody is a labeled antibody.

38. The method of claim 35 wherein the levels of Pro108 and PSA are measured in a sample from said patient selected from the group consisting of cells, tissues, blood, serum, plasma, urine, stool, salvia and sputum.

39. A method for assessing risk of ovarian or colon cancer in a patient which comprises measuring levels of Pro108 and Carcinoembryonic Antigen (CEA) in a sample obtained from the patient to assess the risk of ovarian or colon cancer in the patient wherein Pro108 is measured with an antibody selected from:
(i) an isolated antibody or antigen binding fragment specific for Pro108 produced by a hybridoma selected from the group consisting of ATCC Accession Number PTA-5885 and PTA-5886; or
(ii) an isolated antibody or antigen binding fragment which competes for binding to the same epitope of Pro108 recognized by the antibody produced by a hybridoma selected from the group consisting of ATCC Accession Number PTA-5885 and PTA-5886, and
wherein an elevated level of Pro108 as compared to a control is indicative of heightened risk of ovarian or colon cancer.

40. The method of claim 39, wherein the antibody that competes for binding to the same epitope is a monoclonal antibody, humanized antibody or human antibody.

41. The method of claim 39 wherein the antibody is a labeled antibody.

42. The method of claim 39 wherein the levels of Pro108 and CEA are measured in a sample from said patient selected from the group consisting of cells, tissues, blood, serum, plasma, urine, stool, salvia and sputum.

43. A method for assessing risk of colon cancer in a patient which comprises measuring levels of Pro108 and CA19.9 in a sample obtained from the patient to assess the risk of colon cancer in the patient wherein Pro108 comprises residues 1-331 of SEQ ID NO:1 or SEQ ID NO:2, wherein an elevated level of Pro108 as compared to a control is indicative of heightened risk for colon cancer.

44. A method for assessing risk of ovarian, lung or colon cancer in a patient which comprises measuring levels of Pro108 and CA19.9 in a sample obtained from the patient to assess the risk of ovarian, lung, or colon cancer in the patient wherein Pro108 is measured with an antibody selected from:
   (i) an isolated antibody or antigen binding fragment specific for Pro108 produced by a hybridoma selected from the group consisting of ATCC Accession Number PTA-5885 and PTA-5886; or
   (ii) an isolated antibody or antigen binding fragment which competes for binding to the same epitope of Pro108 recognized by the antibody produced by a hybridoma selected from the group consisting of ATCC Accession Number PTA-5885 and PTA-5886, and
   wherein an elevated level of Pro108 as compared to a control is indicative of heightened risk of ovarian, lung or colon cancer.

45. The method of claim 44, wherein the antibody that competes for binding to the same epitope is a monoclonal antibody, humanized antibody or human antibody.

46. The method of claim 44 wherein the antibody is a labeled antibody.

47. The method of claim 44 wherein the levels of Pro108 and CA19.9 are measured in a sample from said patient selected from the group consisting of cells, tissues, blood, serum, plasma, urine, stool, salvia and sputum.

48. A method for assessing risk of ovarian cancer in a patient which comprises measuring levels of Pro108 and CA125 in a sample obtained from the patient to assess the risk of ovarian cancer in the patient wherein Pro108 is measured with an antibody selected from:
   (i) an isolated antibody or antigen binding fragment specific for Pro108 produced by a hybridoma selected from the group consisting of ATCC Accession Number PTA-5885 and PTA-5886; or
   (ii) an isolated antibody or antigen binding fragment which competes for binding to the same epitope of Pro108 recognized by the antibody produced by a hybridoma selected from the group consisting of ATCC Accession Number PTA-5885 and PTA-5886, and
   wherein an elevated level of Pro108 as compared to a control is indicative of heightened risk of ovarian cancer.

49. The method of claim 48, wherein the antibody that competes for binding to the same epitope is a monoclonal antibody, humanized antibody or human antibody.

50. The method of claim 48 wherein the antibody is a labeled antibody.

51. The method of claim 48 wherein the levels of Pro108 and CA125 are measured in a sample from said patient selected from the group consisting of cells, tissues, blood, serum, plasma, urine, stool, salvia and sputum.

* * * * *